(12) United States Patent
Varchi et al.

(10) Patent No.: US 8,741,951 B2
(45) Date of Patent: Jun. 3, 2014

(54) NON-STEROIDAL COMPOUNDS FOR ANDROGEN RECEPTOR MODULATION

(75) Inventors: Greta Varchi, Bologna (IT); Andrea Guerrini, Bologna (IT); Anna Tesei, Meldola (IT); Giovanni Brigliadori, Meldola (IT)

(73) Assignees: CNR—Consiglio Nazionale delle Ricerche, Rome (IT); Istituto Scientifico Romagnolo per lo Studio e la Cura dei Tumori (I.R.S.T.) S.r.l., Meldola (FC) (IT)

( * ) Notice: Subject to any disclaimer, the term of this patent is extended or adjusted under 35 U.S.C. 154(b) by 16 days.

(21) Appl. No.: 13/263,616

(22) PCT Filed: Apr. 12, 2010

(86) PCT No.: PCT/IB2010/051548
§ 371 (c)(1),
(2), (4) Date: Nov. 2, 2011

(87) PCT Pub. No.: WO2010/116342
PCT Pub. Date: Oct. 14, 2010

(65) Prior Publication Data
US 2012/0041046 A1    Feb. 16, 2012

(30) Foreign Application Priority Data

Apr. 10, 2009  (IT) ............ BO2009A000235
Apr. 10, 2009  (IT) ............ BO2009A000236

(51) Int. Cl.
*A61K 31/277*  (2006.01)
*A61K 31/381*  (2006.01)
*C07C 255/60*  (2006.01)
*C07D 333/24*  (2006.01)

(52) U.S. Cl.
USPC ............. 514/522; 558/413; 558/414; 549/77; 514/438

(58) Field of Classification Search
CPC .. C07D 333/24; C07D 231/14; C07D 235/16; C07D 235/38; C07D 255/60; A61K 31/167; A61K 31/277; A61K 31/381
USPC .................. 514/486, 438, 522; 558/413, 414; 549/77
See application file for complete search history.

(56) References Cited

U.S. PATENT DOCUMENTS 4,636,505 A  1/1987 Tucker
6,583,306 B1  6/2003 Ekwuribe

FOREIGN PATENT DOCUMENTS

JP    2008239490 A  * 10/2008
WO    98/53826 A1    12/1998
WO    2008/011072 A2  1/2008

OTHER PUBLICATIONS

Sani, Monica; Viani, Fiorenza; Binda, Mara; Zaffaroni, Nadia; Zanda, Matteo, Synthesis and in vitro anti-proliferative activity of racemic trifluoro-Casodex (bicalutamide), Letters in Organic Chemistry (2005), 2(5), 447-449.*

He, Y., et al.: "Novel nonsteroidal ligands with high binding affinity and potent functional activity for the androgen receptor", European Journal of Medicinal Chemistry, Editions Scientifique Elsevier, Paris, FR LNKD-DOI:10.1016/S0223-5234(02)01335-1, vol. 37, No. 8, Aug. 1, 2002, pp. 619-634, XP004381320, ISSN: 0223-5234.

Tucker, H., et al.: "Nonsteroidal Anti androgens. Synthesis and structure-activity relationships of 3-substituted derivatives of 2-hydroxypropionanilides", Journal of Medicinal Chemistry, American Chemical Society, Washington, US LNKDDOI: 10.1021/JM00400A011, vol. 31, No. 5, Jan. 1, 1988, pp. 954-959, XP002489997, ISSN: 0022-2623.

Seebach, D., et al.: "Alpha-alkylation of alpha-heterosubstituted carboxylic acids without racemization epc-syntheses of tertiary alcohols and thiols", Tetrahedron, Elsevier Science Publishers, Amsterdam, NL, vol. 40, No. 8, Jan. 1, 1984, pp. 1313-1324, XP001093789, ISSN: 0040-4020.

Hof, R. P., et al.: "Synthesis and lipase-catalysed resolution of 5-(hydroxymethyl)-1,3-dioxolan-4-ones: masked glycerol analogues as potential building blocks for pharmaceuticals", Journal of Organic Chemistry, American Chemical Society, Easton.; US, vol. 61, No. 10, May 17, 1996, pp. 3423-3427, XP002163350, ISSN: 0022-3263.

Huang, Y., et al.: "A concise synthesis of (R)- and (S)-alpha-alkyl isoserines from d- and l-malic acids", Tetrahedron Asymmetry, Pergamon Press LTD, Oxford, GB, vol. 17, No. 22, Nov. 27, 2006, pp. 3152-3157, XP024962297, ISSN: 0957-4166, [retrieved on Nov. 27, 2006].

Leipen, R.,: "Uber einige Verbindungen der Athylidenmilchsiure", Monatshefte Fur Chemie, Springer Verlag Wien, At, vol. 9, No. 1, Dec. 1, 1888, pp. 45-51, XP009126525, ISSN: 0026-9247.

Kirkovsky, L., et al.: "Chiral nonsteroidal affinity ligands for the androgen receptor 1. Bicalutamide analogues bearing electrophilic groups in the B aromatic ring", Journal of Medicinal Chemistry, American Chemical Society, Washington, US, vol. 43, No. 4, Feb. 24, 2000, pp. 581-590, XP002207426, ISSN: 0022-2623.

* cited by examiner

*Primary Examiner* — Kendra D Carter
*Assistant Examiner* — Jason A Deck
(74) *Attorney, Agent, or Firm* — Lucas & Mercanti LLP

(57) ABSTRACT

The present invention concerns compounds of general Formula (I): method of preparation and uses thereof.

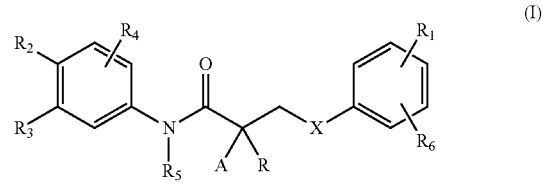

15 Claims, 32 Drawing Sheets

(R)-XXIII-5

LNCaP

Figure 1:
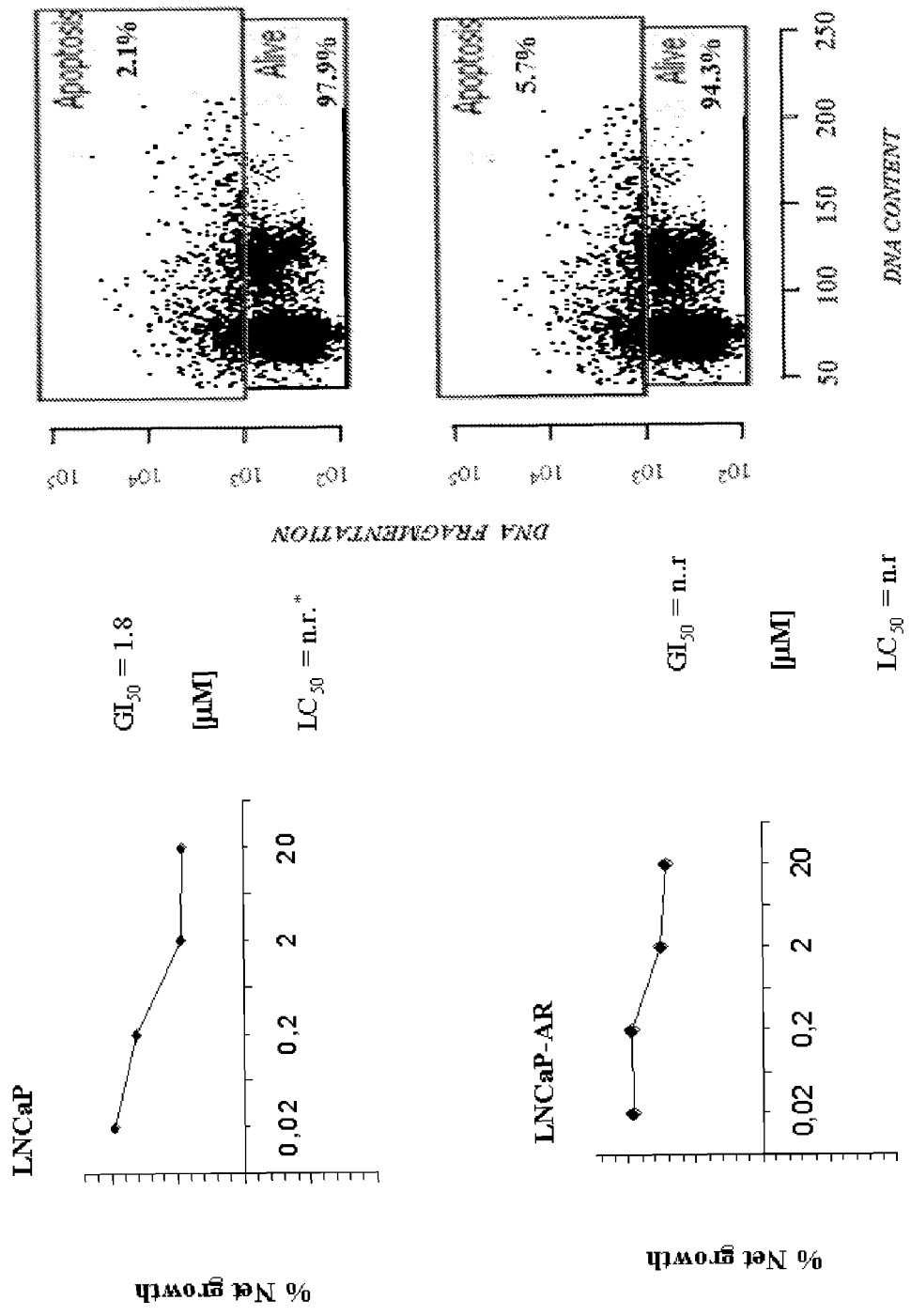
Figure 2:
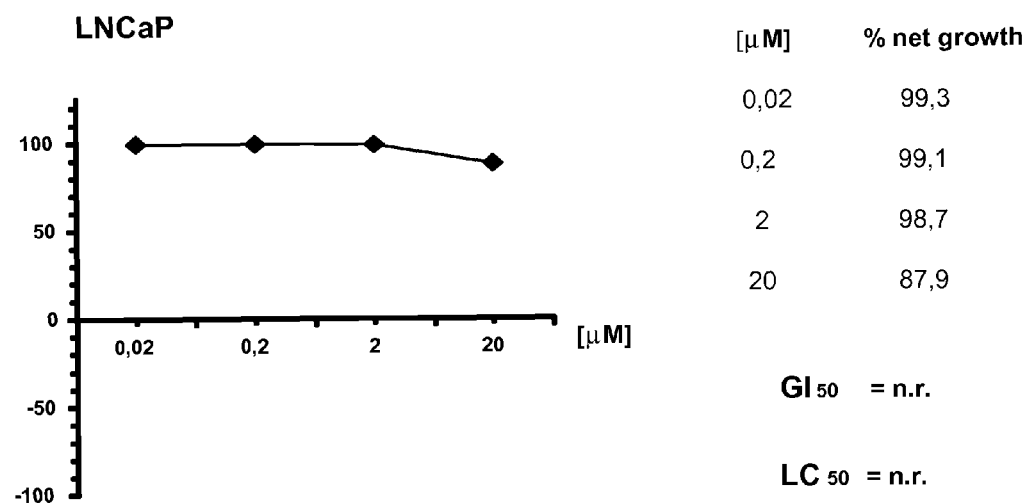
Figure 2:
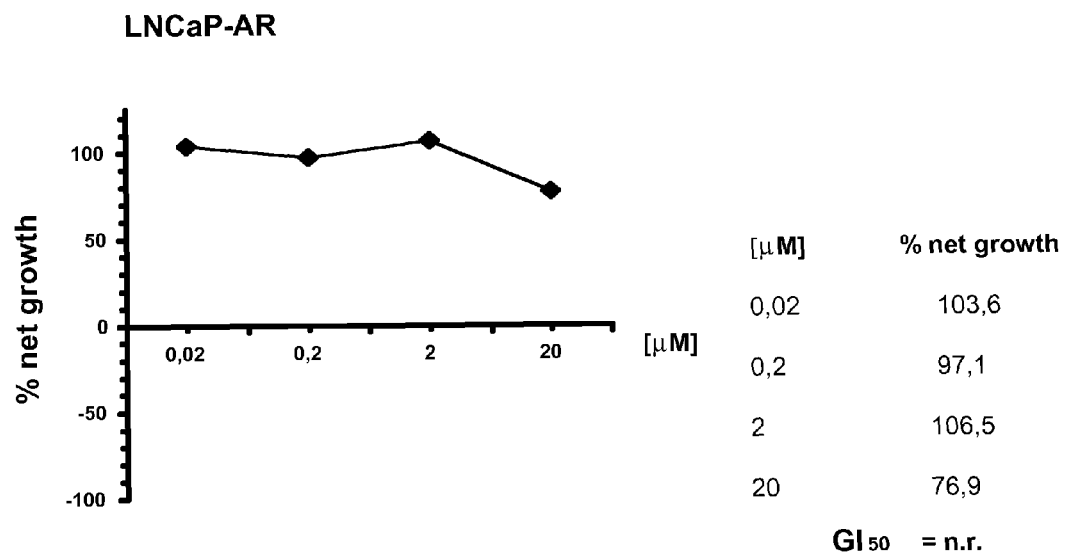
Figure 3:
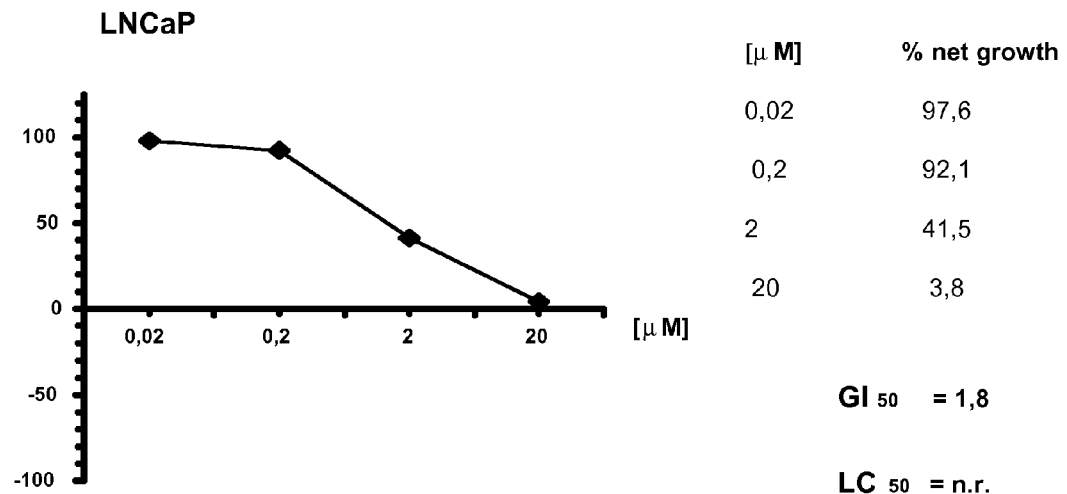
Figure 3:
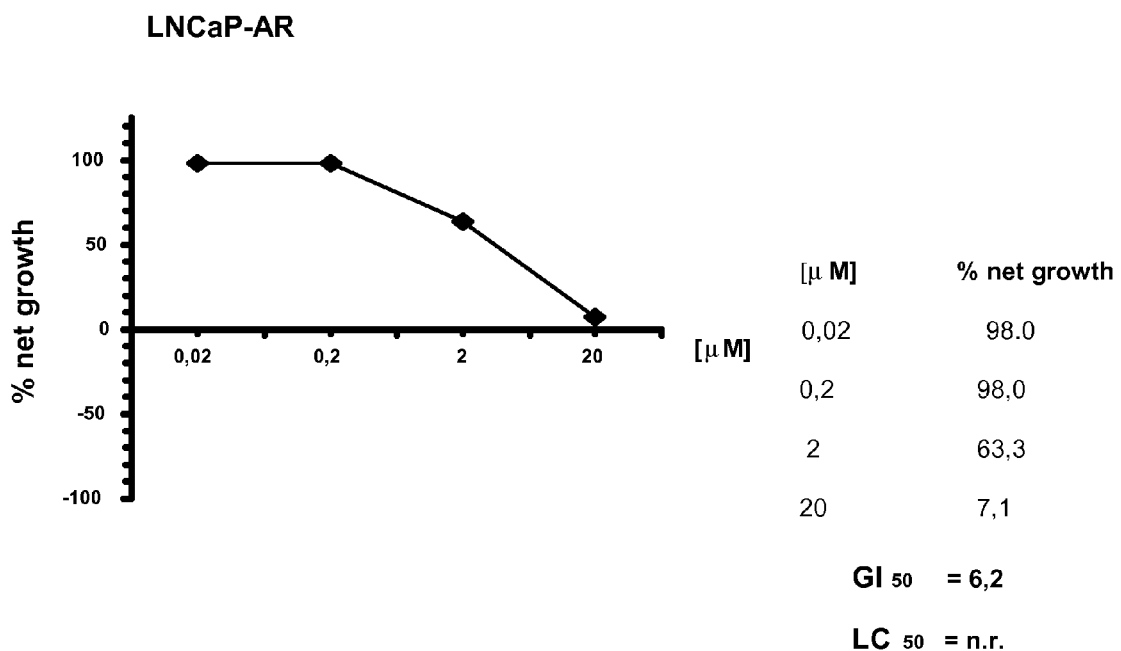
Figure 4:
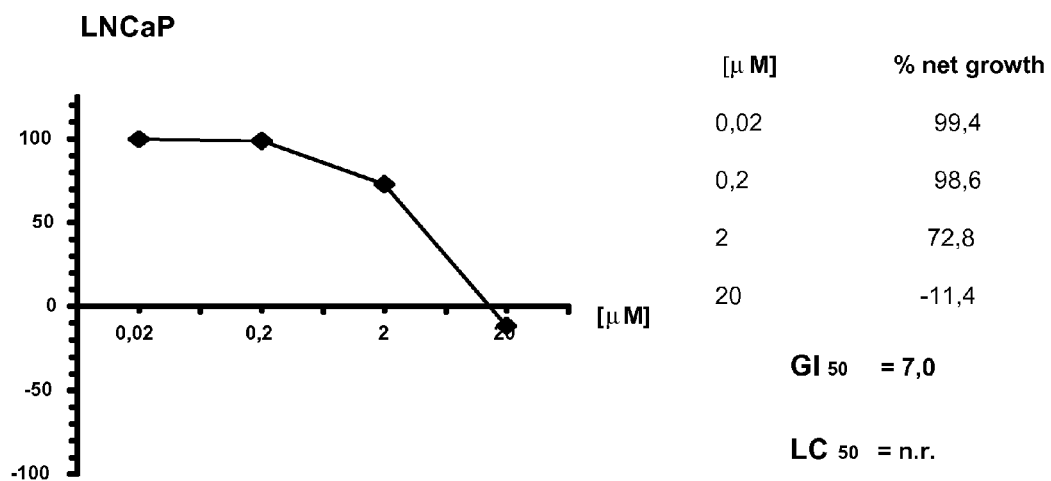
Figure 4:
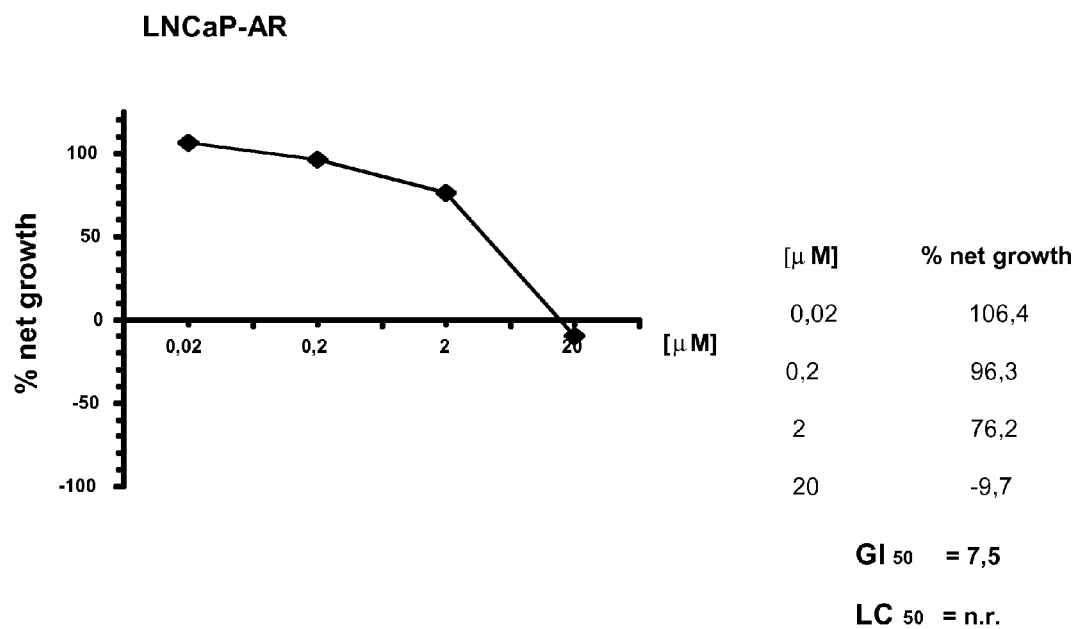
Figure 5:
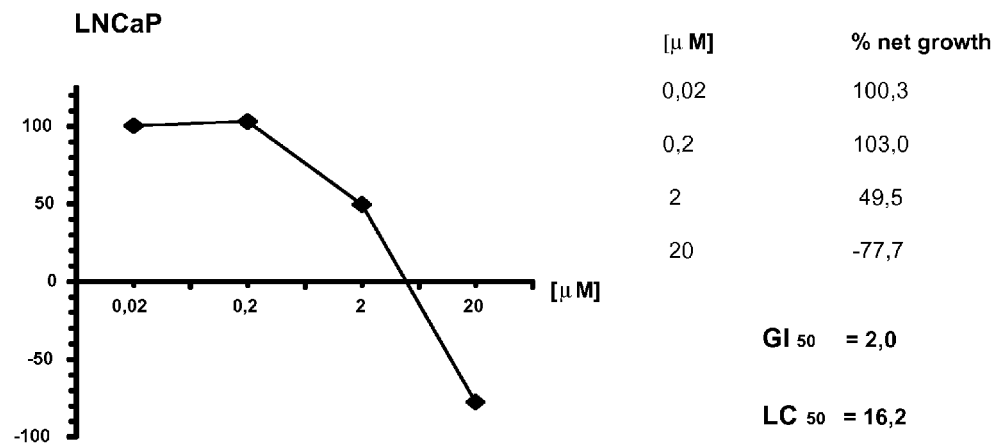
Figure 5:
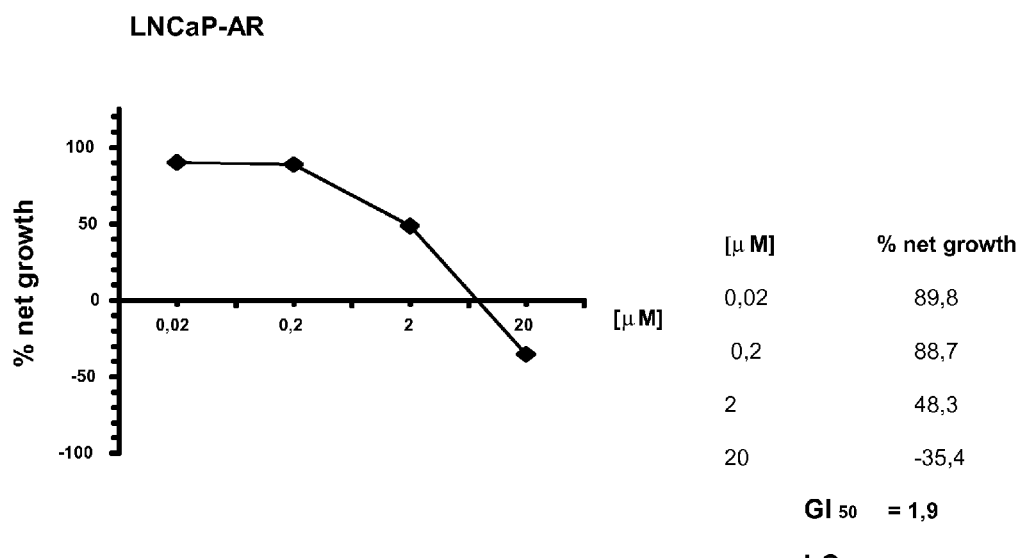
Figure 6:
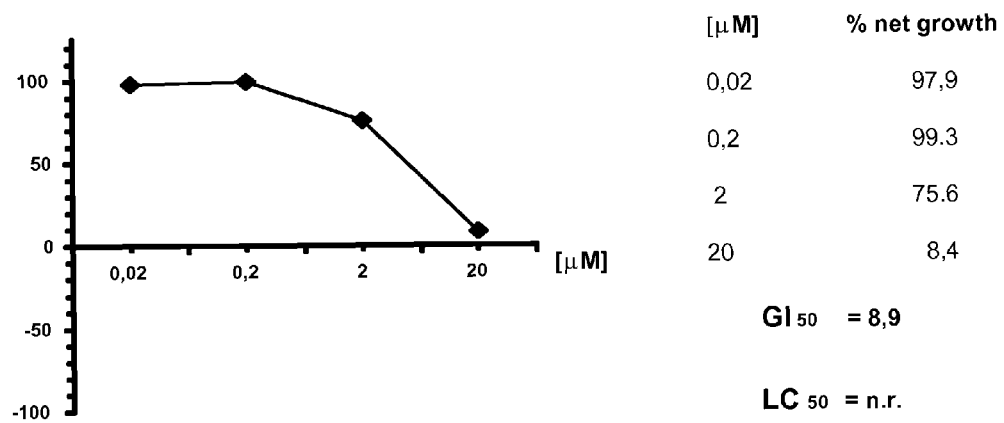
Figure 6:
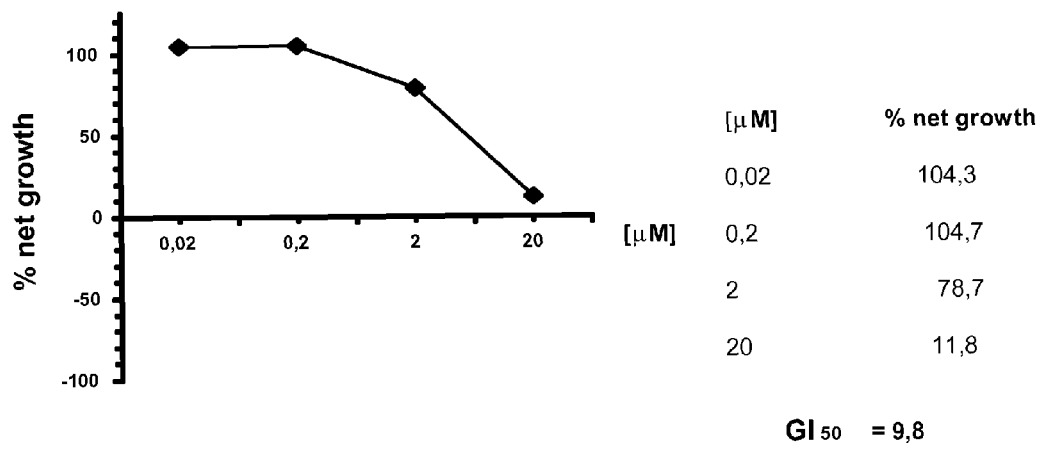
Figure 7:
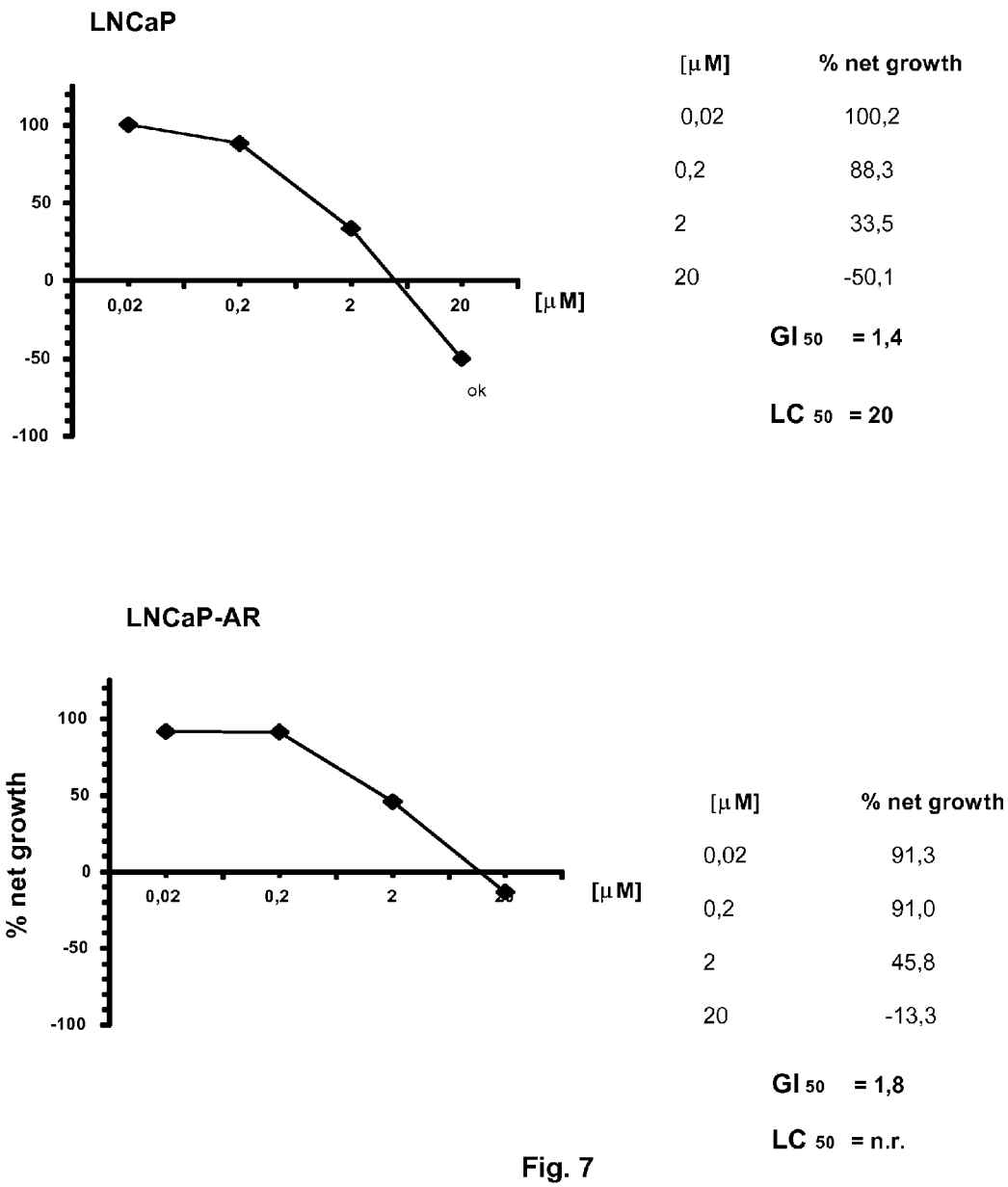
Figure 8:
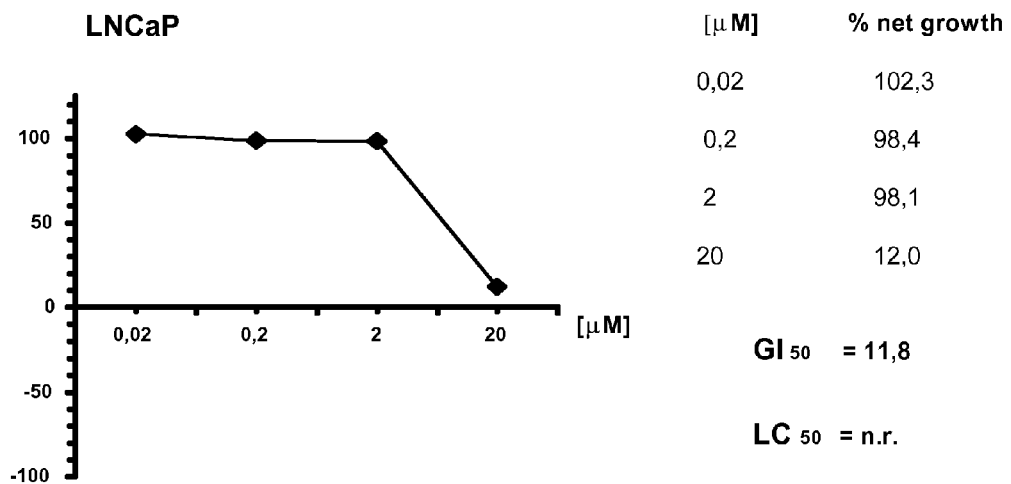
Figure 8:
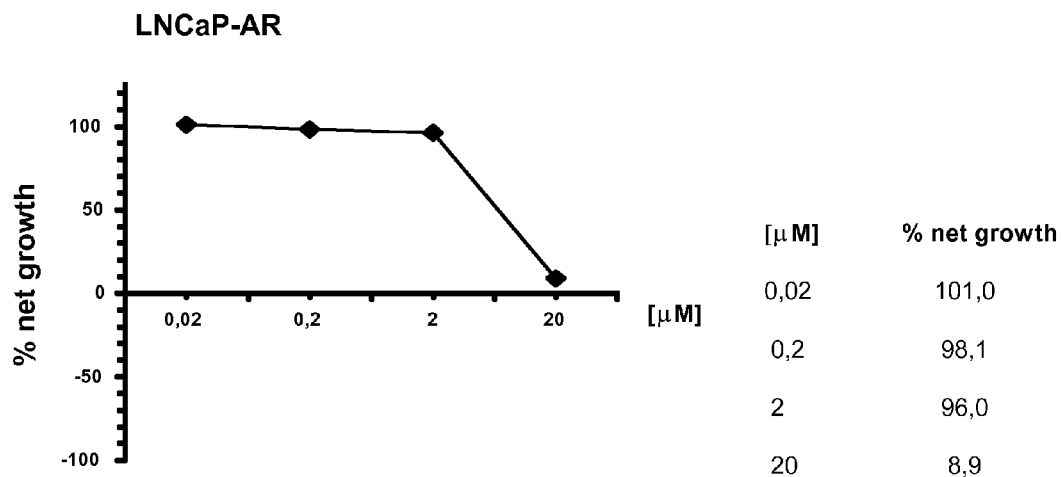
Figure 9:
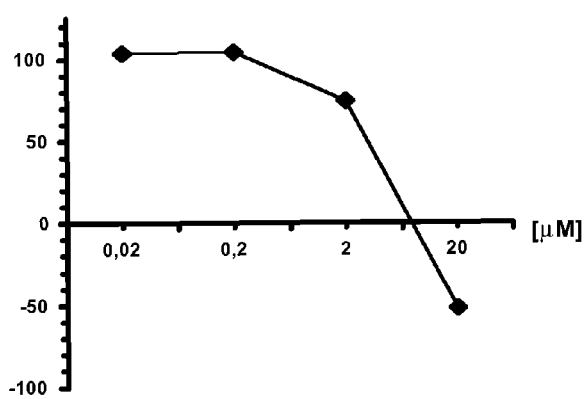
Figure 9:
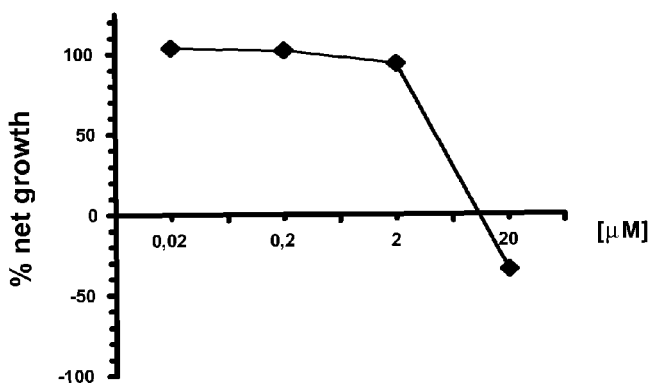
Figure 10:
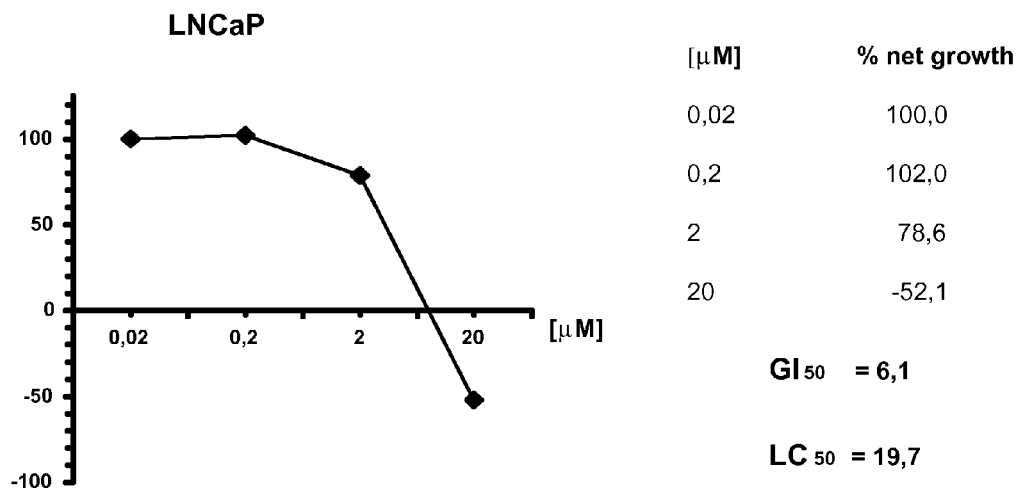
Figure 10:
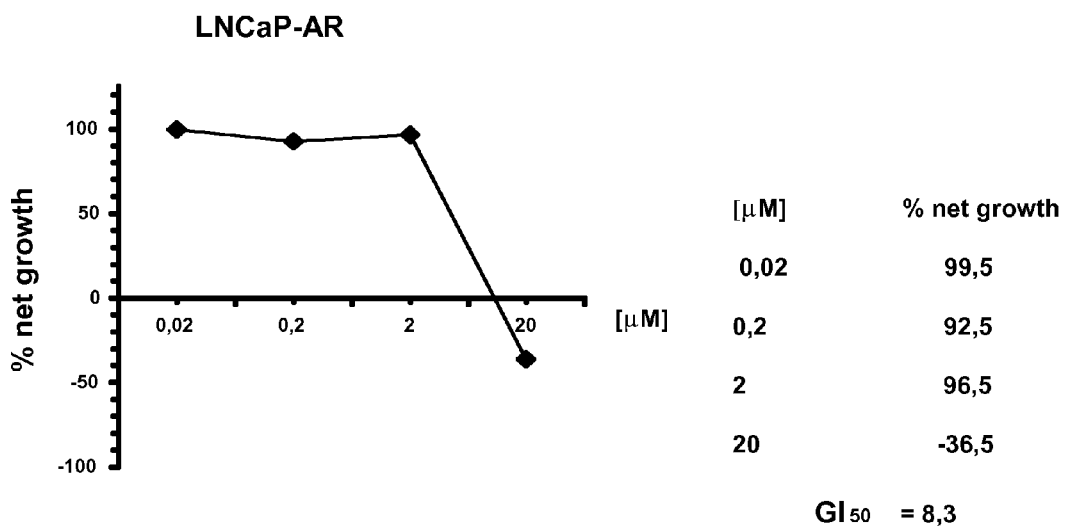
Figure 11:
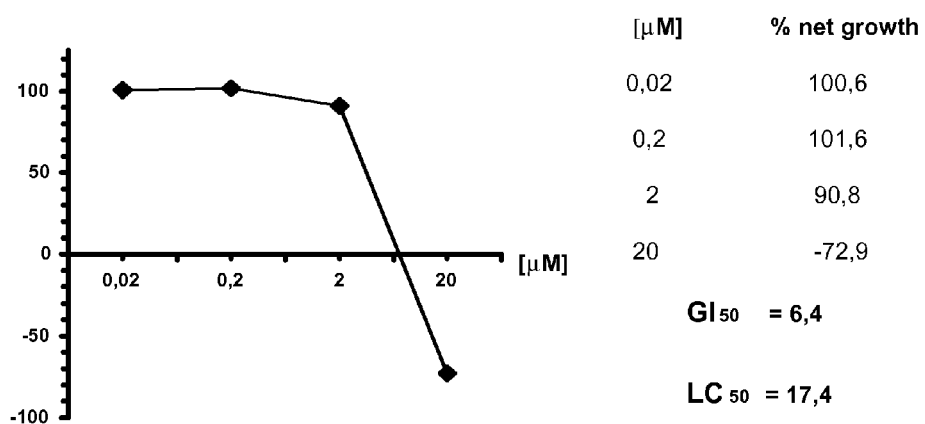
Figure 11:
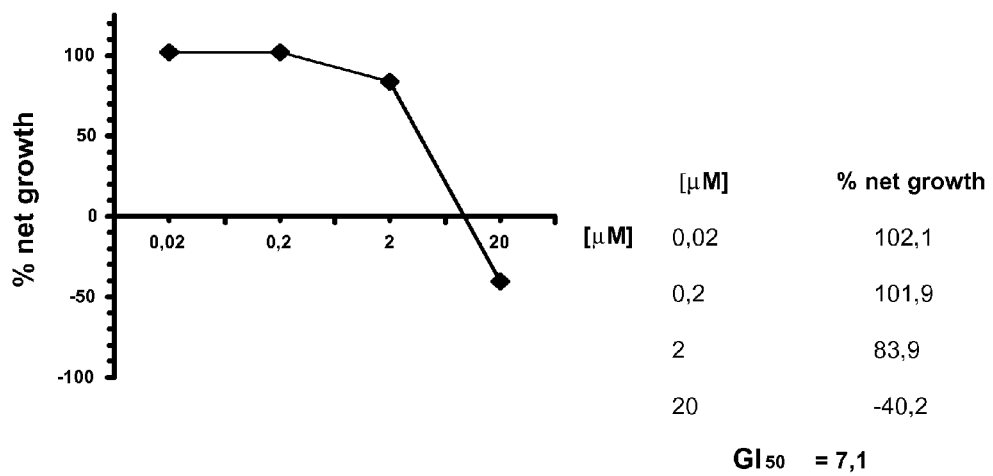

| [μM] | % net growth |
|------|--------------|
| 0,02 | 100,3 |
| 0,2 | 103,0 |
| 2 | 49,5 |
| 20 | -77,7 |

GI$_{50}$ = 2,0

LC$_{50}$ = 16,2

LNCaP-AR

| [μM] | % net growth |
|------|--------------|
| 0,02 | 89,8 |
| 0,2 | 88,7 |
| 2 | 48,3 |
| 20 | -35,4 |

GI$_{50}$ = 1,9

LC$_{50}$ = n.r.

(R) -XXIII-6

(R)-XXIII-9

LNCaP

| [μM] | % net growth |
|---|---|
| 0,02 | 103,7 |
| 0,2 | 104,4 |
| 2 | 74,4 |
| 20 | -52,1 |

GI$_{50}$ = 5,7

LC$_{50}$ = 19,7

LNCaP-AR

| [μM] | % net growth |
|---|---|
| 0,02 | 103,4 |
| 0,2 | 101,8 |
| 2 | 93,8 |
| 20 | -34,2 |

GI$_{50}$ = 8,2

LC$_{50}$ = n.r.

(R)-XXIV-9

LNCaP

| [μM] | % net growth |
|------|--------------|
| 0,02 | 100,6 |
| 0,2  | 101,6 |
| 2    | 90,8 |
| 20   | -72,9 |

GI$_{50}$ = 6,4

LC$_{50}$ = 17,4

LNCaP-AR

| [μM] | % net growth |
|------|--------------|
| 0,02 | 102,1 |
| 0,2  | 101,9 |
| 2    | 83,9 |
| 20   | -40,2 |

GI$_{50}$ = 7,1

LC$_{50}$ = n.r.

(R) -XXIII-3

PC-3

| [μM] | % net growth |
|---|---|
| 0,02 | 98,6 |
| 0,2 | 99,1 |
| 2 | 96,9 |
| 20 | 27,8 |

GI$_{50}$ = 14,1

LC$_{50}$ = n.r.

DU-145

| [μM] | % net growth |
|---|---|
| 0,02 | 99,3 |
| 0,2 | 98,3 |
| 2 | 97,9 |
| 20 | 38,4 |

GI$_{50}$ = 16,5

LC$_{50}$ = n.r.

(R)-XXIII-8

(R) -XXIII-9

PC-3

| [μM] | % net growth |
|---|---|
| 0,02 | 99,5 |
| 0,2 | 98,3 |
| 2 | 99,2 |
| 20 | -60,6 |

GI$_{50}$ = 7,5

LC$_{50}$ = 18,7

DU-145

| [μM] | % net growth |
|---|---|
| 0,02 | 98,9 |
| 0,2 | 99,6 |
| 2 | 93,9 |
| 20 | -75,2 |

GI$_{50}$ = 6,6

LC$_{50}$ = 17,2

(R)-XXIII-10

PC-3

| [μM] | % net growth |
|---|---|
| 0,02 | 99,5 |
| 0,2 | 99,6 |
| 2 | 99,2 |
| 20 | -53,4 |

GI$_{50}$ = 7,8

LC$_{50}$ = 19,6

DU-145

| [μM] | % net growth |
|---|---|
| 0,02 | 98,3 |
| 0,2 | 93,9 |
| 2 | 98,9 |
| 20 | -80,1 |

GI$_{50}$ = 6,9

LC$_{50}$ = 17,0

(R)-XXIV-9

| [μM] | % net growth |
|---|---|
| 0,02 | 99,4 |
| 0,2 | 99,2 |
| 2 | 98,9 |
| 20 | -15,3 |

$GI_{50}$ = 9,7

$LC_{50}$ = n.r.

| [μM] | % net growth |
|---|---|
| 0,02 | 99,3 |
| 0,2 | 98,9 |
| 2 | 90,4 |
| 20 | -58,2 |

$GI_{50}$ = 6,9

$LC_{50}$ = 19,1

NON-STEROIDAL COMPOUNDS FOR ANDROGEN RECEPTOR MODULATION

CROSS-REFERENCE TO RELATED APPLICATIONS

This application is a 371 of PCT/IB2010/051548, filed on Apr. 12, 2010, which claims the benefit of Italian Patent Application Nos. BO2009A000235, filed on Apr. 10, 2009, and BO2009A000236, filed on Apr. 10, 2009, the contents of each of which are incorporated herein by reference.

FIELD OF THE INVENTION

The present invention provides nuclear hormone receptor binding compounds and pharmaceutically acceptable salts and esters thereof useful in the treatment of nuclear receptor, especially steroid receptor, and in particular androgen receptor (AR) dependent conditions. In particular, the invention discloses novel non-steroidal propionanilide and hydantoine structured compounds having utility as tissue-selective androgen receptor modulators (SARM). The compounds of the invention, which possess AR antagonist activity, are useful in prostate cancer therapy, especially in treatment of hormone-refractory prostate cancer.

BACKGROUND OF THE INVENTION

Androgen receptor (AR), a member of the steroid receptor super-family, is a ligand-dependent transcription factor that mediates androgen action in cells. The AR is widely distributed among cardiac muscle, skeletal and smooth muscle, gastrointestinal vesicular thyroid follicular cells, adrenal cortex, liver, pineal, and numerous brain cortical and subcortical regions, including spinal motor neurons. AR is composed of three major domains: an $NH_2$-terminal transcriptional activation domain, a central DNA-binding domain, and a COOH-terminal ligand-binding domain. After binding to androgens, AR translocates to the nucleus and regulates expression of AR target reproductive and non-reproductive tissues, including the prostate and seminal vesicles, male and female external genitalia, skin, testis, ovary, cartilage, sebaceous glands, hair follicles, sweat glands, genes. [Gelmann E. P. *J Clin Oncol* 2002, 20, 3001-15; Heinlein, C. A.; Chang, C. *Endocr Rev* 2004, 25, 276-308] AR hypersensitivity, as a result of AR gene mutation and/or amplification, overexpression of coactivators, often occurs and plays crucial roles in prostate cancer development, progression, and androgen-independent growth. [Heinlein, C. A.; Chang, C. *Endocr Rev* 2004, 25, 276-308; Chen, C. D.; Welsbie. D.-S.; Tran, C., Baek, S. H.; Chen, R.; Vessella, R.; Rosenfeld, M. G.; Sawyers, C. L. *Nat. Med.*, 2004; 10, 33-9; Isaacs, J. T.; Isaacs, W. B. Nat. Med. 2004; 10, 26-7] Therefore, in most cases advanced prostate cancer, one of the leading cause of cancer death in men after lung cancer, it has been directly linked to the androgen receptor (AR). Most prostatic tumors are stimulated to grow by androgens, and consequently androgen withdrawal is a well-established therapy for prostate cancer treatment. Androgen deprivation therapies consist of surgical castration, through orchidectomy or medical castration by administration of a luteinising hormone-releasing hormone analogue (LHRH-A), such as goserelin [Kirby, R. S. Crit. *J Clin Pract* 1996; 50, 88-93] (Zoladex™, AstraZenaca). However, although castration removes androgen release from the testes, androgen biosynthesis in the adrenals (8±10% of total circulating androgens) is not affected. [Geller J. The role of adrenal androgens in prostate cancer. In: Pasqualini J. R., Katzenellenbogen, B. S. (eds). *Hormone-Dependent Cancer*. Marcel Dekker: New York, 1996, 289-305] Because of this, a widely used management strategy for advanced prostate cancer is a combination of surgical or chemical castration and administration of antiandrogens. [Labrie, F.; Dupont, A.; Belanger, A.; Cusan, L.; Lacourciere, Y.; Monfette, G.; Laberge, J. G.; Emond, J. P; Fazekas Ata, Raynaud, J. P.; Husson, J. M. *Clin Invest Med* 1982; 5, 267-275]

Antiandrogens bind to the AR and inhibit all androgens at the target cell level. In particular, antiandrogens compete with endogenous androgens for binding sites of the androgen receptors in the prostate cell nucleus, thereby promoting apoptosis and inhibiting prostate cancer growth. By contrast with androgens, however, the receptor-antiandrogen complex is unstable so that gene transcription and protein synthesis are not stimulated. [Gaillard-Moguilewsky, M. *Urology* 1991, 37 (Suppl), 5-12]

Ideally, an antiandrogen should possess high specificity and affinity for the androgen receptor, being devoid of other hormonal or anti-hormonal activity. Antiandrogens act by two primary mechanisms: inhibition of ligand (androgen) binding to the AR, and inhibition of androgen-independent activation of the receptor. It is more accurate to refer to these compounds as androgen-receptor antagonists, since they inhibit activation, whether this is androgen-mediated or not. There are two structurally distinct types of antiandrogen, i.e. steroidal and nonsteroidal. One steroidal and three non-steroidal antiandrogens are in common use for the treatment of prostate cancer. However, the use of the steroidal agent cyproterone acetate (CPA), a synthetic derivative of hydroxyprogesterone, is limited since, in addition to blocking androgen receptors, has progestational and antigonadotrophic properties. [Furr, B. J. A.; Kaisary, A. V. Treatment: hormonal manipulation: Antiandrogens. In Kaisary, A. V.; Murphy, G. P.; Denis, L.; Griffiths, K. eds. *Textbook of Prostate Cancer: Pathology, Diagnosis and Treatment*. London: Martin Dunitz, 1999: 277-90]

CPA therefore inhibits the release of LH, decreasing serum testosterone levels, and causing a severe suppression of libido and loss of erectile potency. The nonsteroidal antiandrogens, bicalutamide, flutamide and nilutamide are pure antiandrogens, which exert their effects through competitive inhibition of the binding of testosterone, and its metabolite 5-α dihydrotestosterone (5α-DHT), to the nuclear androgen receptor. As testosterone levels are not blocked by nonsteroidal antiandrogens, [Gaillard-Moguilewsky, M. *Urology* 1991, 37 (Suppl), 5-12] these drugs offer the possibility of maintaining sexual interest and potency. Within the class of non-steroidal anti-androgens, there is variation in the degree to which ligand-independent activation is inhibited. Preclinical data suggest that non-steroidal antiandrogen bicalutamide may be a more effective drug in the treatment of prostate cancer with respect to flutamide and nilutamide. [Tucker, H.; J. W. Crook, J. W.; Chesterson J. *J. Med. Chem.*, 1988, 31, 954-959].

Bicalutamide (IUPAC name: N-[4-cyano-3-(trifluoromethyl)phenyl]-3-[(4-fluorophenyl)sulfonyl]-2-hydroxy-2-methyl-propanamide], is currently owned and sold by ASTRA ZENECA pharmaceuticals as Casodex®. Bicalutamide acts by lowering prostate testosterone level, without affecting the regulatory activity of the hypothalamus.

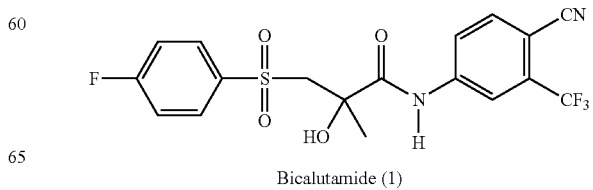

Bicalutamide (1)

-continued

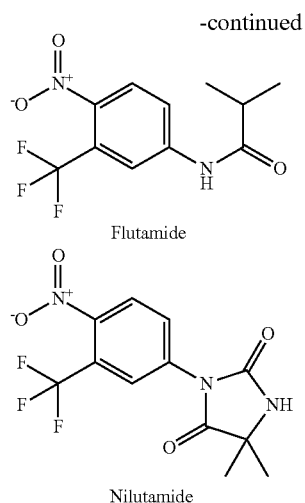

Flutamide

Nilutamide

The endocrine therapy using non-steroidal antiandrogens and LHRH analogs is initially very effective but is time-limited. Nearly half of all patients with these tumors develop resistance to this therapy after several years, suggesting the development of androgen-independent prostate cancer cells or the ability of adrenal androgens to support tumor growth. This leads to serious clinical inconveniences. [Oh, W. K.; Kantoff, P. W. *J Urol* 1998, 160, 1220-1229]

Surprisingly, clinical benefit has been observed following the withdrawal of anti-androgens (Anti-Androgen Withdrawal Response, AAWR) in a subset of prostate cancer patients with therapy-resistant disease. [Scher, H. I.; Kolvenbag, G. J. *Eur Urol.*, 1997, 31, 3-7] The anti-androgen withdrawal event indicate that there may be clinically relevant changes in AR expression and function during long-term androgen ablation which can be in part attributed to mutant ARs detected in prostatic carcinomas. For example, bicalutamide that acts as a pure antagonist in parental LNCaP cells, showed agonistic effects on AR transactivation activity in LNCaP-abl cells and was not able to block the effects of androgen in these cells. [Culig, Z.; Hoffmann, J.; Erdel, M.; Ederl, I. E.; Hobischl, A.; A Hittmair, A.; Bartschl, G.; G Utermann, G.; M R Schneider, M. R.; Parczyk, K.; Klocker, H. *British J. of Cancer* 1999, 81, 242-251] However, alternative mechanisms may also be considered. In fact, it has been found that non-steroidal antiandrogens act as AF-1 agonists under conditions of high AR protein expression. This partial antagonistic property of antiandrogens may be a molecular mechanism by which prostate cancer develops resistance to these drugs. [Fuse, H.; Korenaga, S.; Sakari, M.; Hiyama, T.; Ito, T. Kimura, K.; Kato, S. *The Prostate,* 2007, 67, 630-637] These findings may have repercussions on the natural course of prostate cancer with androgen deprivation and on strategies of therapeutic intervention. For this reason, secondary treatment to block androgen receptors in a primary, secondary or tertiary manner has been developed. Secondary hormonal manipulations for affected patients include antiandrogen withdrawal, second-line antiandrogens, [Kojima, S.; Suzuki, H.; Akakura, K.; Shimbo, M., Ichikawa T.; Ito, H. *J Urol.* 2004, 171, 679-683] direct adrenal androgen inhibitors (aminoglutethimide, ketoconazole), [Mahler, C.; Verhelst, J.; Denis, *Cancer,* 1993, 71, 1068; Sartor, O.; Cooper, M.; Weinberger, M.; Headlee, D., Thibault, A; Tompkins, A.; Steinberg, S.; Figg, W. D.; Linehan, W. M.; Myers, C. E. *J. Natl. Cancer Inst.* 1944, 86, 222] corticosteroids (eg: mitoxantone), [Tannock, I. F.; Osoba, D.; Stockier, M. R.; Emst, D. S.; Neville, A. J.; Moore, M. J.; Armitage, G. R.; Wilson, J. J.; Venner, P. M.; Coppin, C. M.; Murphy, K. C.: *J. Clin. Oncol.* 1996, 14, 1756] estrogens [Ferro, M. A.; Gillatt, D., Symes, M. O.; Smith, P. *J. Urology* 1989, 34: 134] and progestins.

More recently, new classes of antiandrogens have been investigated. These compounds have not yet clinically been evaluated, but demonstrate potent antiandrogenic activity in in vitro and preclinical models. Selected examples are: a) Bicyclic-[1]H-isoindole-1,3-(2H)-dione analogues which can be considered as tructurally modified of nilutamide analogues. [Salvati, M. E.; Balog, A.; Wei, D. D.; Pickering, D.; Attar, R. M.; Geng, J.; Rizzo, C. A.; Hunt, J. T.; Gottardis, M. M.; Weinmann, R.; Martinez, R. *Bioorg. Med. Chem. Lett.* 2005, 15, 389] b) quinolone derivatives with a linear tricyclic pharmacophore, 2(1H)-piperidino [3,2-g]quinolinone. [Hamann, L. G.; Higuchi, R. I.; Zhi, L.; Edwards, J. P.; Wang, X. N.; Marschke, K. B.; Kong, J. W.; Farmer, L. J.; Jones, T. K. *J. Med. Chem.* 1998, 41, 623] c) androgen receptor antagonists containing a carborane moiety as a hydrophobic skeletal structure. These compounds bind to AR and show anti-androgenic activity towards androgen-dependent SC-3 cells with almost the same potency as the known anti-androgen hydroxyflutamide. [Fujii, S.; Hashimoto, Y.; Suzuki, T.; Ohta, S.; Endo, Y. *Bioorg. Med. Chem. Lett.* 2005, 15, 227-230] d) β-Alkylthio indolyl carbinols [Lanter, J. C.; Fiordeliso, J. J.; Alford, V. C.; Zhang, X.; Wells, K. M.; Russell, R. K.; Allana, G. F.; Laia, M.-T.; Lintona, O.; Lundeena, S.; Sui, Z. *Bioorg. Med. Chem. Lett.* 2007, 17, 2545-2548] e) Phenotiazine derivatives. [Bisson, W. H.; Cheltsov, A. V.; Bruey-Sedano, N.; Lin, B.; Chen, J.; Goldberger, N.; May, L. T.; Christopoulos, A.; J. T. Dalton, J. T.; P. M. Sexton, P. M.; X.-K. Zhang, X.-K.; and R. Abagyan R. *PNAS,* 2007, 104, 11927-11932] Although these nonsteroidal antiandrogens exhibit high specificity for AR and are orally available, they do not possess tissue selectivity. Along with the blockade of AR action in the prostate, antiandrogens also block AR actions in other target tissues, including anabolic tissues (e.g., skeletal muscle and bone) and the hypothalamus-pituitary-testis axis. In the past several years, a new class of non-steroid molecules targeting the androgen receptors has emerged. [Zhi, L.; Martinborough, E. *Annu. Rep. Med. Chem.* 2001, 36, 169; Negro-Vilar, A. *J. Clin. Endocrinol. Metab.* 1999, 84, 3459] For these molecules the term of selective androgen receptor modulators (SARMs) has been chosen after the discovery of similar molecules, the selective estrogen receptor modulators (SARMs), which targets the estrogen receptors. SARMs selectively bind and modulate ARs depending on tissue type. The goal of research in this area is to allow a customized response, namely, tissues that are the target of the therapy will respond as they would to testosterone; other tissues, where undesirable side effects are produced, will not. For an ideal selective androgen receptor modulator, the antagonist or weak agonist activity in the prostate will not stimulate nascent or undetected prostate cancer; while the strong agonist activity can be exploited to stimulate testosterone's beneficial action in bone, muscle and brain, either cross or not cross into the central nervous system to affect lipids. Because of these properties, SARMs could be developed to treat a range of medical conditions and physiological functions. Potential indications are: andropause conditions of aging [Tenover, J. L. *J Androl* 1997, 18, 103-106] (hypogonadism, sarcopenia, osteoporosis, high cholesterol); disorders of the nervous central system (low libido, depression and mood); male reproduction [Wu, F. C. *Baillieres Clin. Endocrinol. Metab.* 1992, 6, 373-403] (infertility, male contraception, erectile disfunction); wasting conditions associated with disease and trauma (cancer, AIDS); end stage of renal disease; severe burns;

prostate disorders (BPH, prostate cancer) and other conditions (anemia, obesity, high cholesterol, hair loss). Structural modifications of bicalutamide led to the discovery of selective androgen receptor modulators. Lead compounds (S)-3-(4-acetylphenoxy)-2-hydroxy-2-methyl-N-[4-nitro-3-(trifluoromethyl)phenyl]-propanamide and (S)-2-hydroxy-2-methyl-N-[4-nitro-3-(trifluoromethyl)phenyl]-3-(4-propionylphenoxy)propanamide, which not only bind AR with high affinity, but also demonstrate tissue selectivity in animal models. [Yin, D.; Gao, W.; Kearbey, J. D.; Xu, H.; Chung, K.; He, Y.; Marhefka, C. A.; Veverka, K. A.; Miller, D. D.; Dalton, J. T. *J. Pharmacol. Exp. Ther.* 2003, 304, 1334-1340; Gao, W.; Kearbey, J. D.; Nair, V. A.; Chung, K.; Parlow, A. F.; Miller, D. D.; Dalton, J. T. *Endocrinology* 2004, 145, 5420-5428].

Quite interestingly, in intact male rats, (S)-3-(4-acetylphenoxy)-2-hydroxy-2-methyl-N-[4-nitro-3-(trifluoromethyl) phenyl]-propanamide and (S)-2-hydroxy-2-methyl-N-[4-nitro-3-(trifluoromethyl)-phenyl]-3-(4-propionylphenoxy) propanamide behaved as antagonists in the prostate without reducing the anabolic effects of androgens, thus suggesting that selective androgen receptor modulators with low intrinsic activity in the prostate, might serve as an alternative therapy for benign prostate hyperplasia (BPH) or even prostate cancer. For this reason, the AR binding ability and in vitro functional activity and the structure-activity relationships (SARs) of a series of nonsteroidal compounds derived from bicalutamide was examined. [He, Y., Yin, D.; Perera, M.; Kirkovsky, L.; Stourman, N.; Li, W.; Dalton, J. T.; Miller, D. D. *Eur. J. Med. Chem.* 2002, 37, 619-634; Yin, D.; He, Y.; Perera, M. A.; Hong, S. S.; Marhefka, C.; Stourman, N.; Kirkovsky, L.; Miller, D. D.; Dalton, J. T. *Mol. Pharmacol.* 2003, 63, 211-223] These studies demonstrated that nonsteroidal ligands can be structurally modified from known nonsteroidal antiandrogens to generate ligands capable of activating AR-mediated transcriptional activation. The conclusion was that the overall effect on AR binding affinities, as well as, their abilities to stimulate AR-mediated transcriptional activation is determined by a delicate balance of factors, including nature, size, and position of the substituent.

There is a need of new compounds having desirable pharmacological properties, and synthetic pathways for preparing them. Because activities are very sensitive to small structural changes, one compound may be effective in treating prostate cancer, whereas a second compound may be effective in treating other AR related pathologies, such as: male contraception, treatment of a variety of hormone-related conditions, for example conditions associated with Androgen Decline an Aging Male (ADAM), such as fatigue, depression, decreased libido, sexual dysfunction, hypogonodism, ospeoporosis, hair loss, anemia, erectile dysfunctions, obesity, sarcopenia, osteopenia, benign prostate hyperplasia, alterations in mood and cognition; treatment of conditions associated with AIDF, such as sexual dysfunctio, decreased sexual libido, hypogonadism, arcopenia, osteopenia, osteoporosis, alterations in cognition and mood, depression, anemia, hair loss, obesity, endometriosis, breast cancer, uterine cancer and ovarian cancer; treatment and/or prevention of chronic muscular wasting or sarcopenia.

Therefore, the aim of the present invention is to provide compounds, their synthesis and their pharmaceutically acceptable preparations, which are useful in the treatment of the above indicated pathologies.

From a structural point of view, bicalutamide is characterized by a central core bearing a quaternary carbon. Thus, bicalutamide exists in two enantiomeric isomers, (US 2007149800 A1); even though the racemic mixture is the only commercialized form. It has been demonstrated that the active biologically form is the (R) enantiomer, which has shown an affinity for the AR 30 fold higher than the (S) enantiomer. (Tyagi, Om Dutt; Chauhan, Yogendra Kumar; Atmaram, Chavan Yuvraj; Dasdaji, Pawar Yogesh. An improved process for the purification of bicalutamide. Indian Pat. Appl. (2007), 15 pp. CODEN: INXXBQ IN 2005KO00778 A 20070525 CAN 147:433448 AN 2007:607391).

Moreover, these compounds are metabolized by liver, [Yuvraj Atmaram; Pawar, Yogesh Dadaji. An improved process for the preparation of bicalutamide. Indian Pat. Appl. (2007), 21 pp. CODEN: INXXBQ IN 2005KO00740 A 20070525 CAN 148:426541 AN 2007:607364] and it has been demonstrated that the (S) form is metabolized much faster than the (R), thus producing an overloading of the liver. A part from these aspects, it has to be considered that the administration of the pure (R) enantiomer would allow much lower dosages.

Consequently, an industrial procedure able to provide the pure (R) enantiomer is highly needed.

A process for the synthesis of (R)-bicalutamide and its analogs has been reported by Ekwuribe (U.S. Pat. No. 6,583, 306 B1). It is worth noting that the synthesis reported by Ekwuribe (U.S. Pat. No. 6,583,306 B1) is performed using (S)-citamallic acid as the starting material, which is too expansive to be used on an industrial scale. Another asymmetric synthesis to produce pure (R)-bicalutamide is made starting from (R)-proline, (WO2006103689) which is again too expansive to be used on an industrial scale.

A third example of (R)-bicalutamide synthesis is an enzymatic hydrolysis of the epoxide 2-methyl glycol benzyl ether (US 2006183934; EP1669347) followed by a complex series of synthetic steps, which are expansive and low yielding.

So far, none of the known processes for the asymmetric synthesis of (R)-bicalutamide is affordable from an industrial point of view, either for the too expansive starting materials or for the too complex synthetic steps. Thus, aim of the present invention is to provide a process for the synthesis of pure (R)-bicalutamide, which is able overcome or partially overcome the drawbacks of state of the art.

SUMMARY OF THE INVENTION

The present invention relates to a synthetic process for the preparation of a novel class of androgen receptor targeting agents, which demonstate antiandrogenic and androgenic activity of a nonsteroidal ligand for androgen receptor. The new compounds are useful for: a) treatment of a variety of hormone-related conditions, b) treatment and/or prevention of chronic muscular wasting. In addition, the process of the present invention is suitable for large-scale preparation of a novel class of androgen receptor targeting agents.

It is therefore an object of the present invention a compound of general formula I:

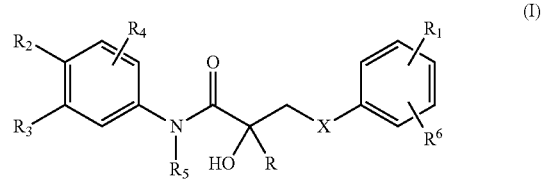

Wherein R is aryl, optionally substituted aryl, heteroaryl, optionally substituted heteroaryl, straight or branched $C_{2-10}$ alkyl, substituted straight or branched $C_{1-12}$ alkyl, straight or branched $C_{2-10}$ heteroalkyl, substituted straight or branched $C_{2-10}$ heteroalkyl, $C_1$-$C_4$-arylalkyl, substituted $C_1$-$C_4$-arylalkyl, $C_{1-4}$ heteroarylalkyl, substituted $C_{1-4}$ heteroarylalkyl;

X is oxygen, sulfur, sulfinyl (—SO—), sulfonyl (—SO$_2$—), alkylimino (—NR″—), (—PR″—), —Se—, where R″ is H, $C_1$-$C_4$ alkyl;

$R^1$ and $R^6$ are the same or different and each independently H, $C_{1-4}$ alkyl or an electron-withdrawing group (defined below).

$R^5$ is H, $C_1$-$C_4$-alkyl;

$R^4$ is H, F, Cl, I or Br;

$R^2$ and $R^3$ are the same or different and each independently H, $C_{1-4}$ alkyl or an electron-withdrawing group. Preferably R is selected in the group consisting of: aryl, optionally substituted aryl, heteroaryl, optionally substituted heteroaryl, straight or branched $C_{2-10}$ alkyl, substituted straight or branched $C_{1-12}$ alkyl, straight or branched $C_{2-10}$ heteroalkyl, substituted straight or branched $C_{2-10}$ heteroalkyl, $C_1$-$C_4$-arylalkyl, substituted $C_1$-$C_4$-arylalkyl, $C_{1-4}$ heteroarylalkyl, substituted $C_{1-4}$ heteroarylalkyl;

X is oxygen, sulfur, sulfinyl (—SO—), sulfonyl (—SO$_2$—), alkylimino (—NR″—), (—PR″—), —Se—, where R″ is H, $C_1$-$C_4$ alkyl;

$R^1$ and $R^6$ are the same or different and each independently are H, $C_{1-4}$ alkyl, halogen, —NO$_2$, —CN, —SiRi$_3$, —NHCOCF$_3$, —NHCOR$^i$, —NHCONHR$^i$, —NHCOOR$^i$, —OCONHR$^i$, —CONHR$^i$, —NHCSCF$_3$, —NHCSR$^i$, —NHSO$_2$R$^i$, —NCS—OR$^i$, —COR$^i$, —COOR$^i$, —OSO$_2$R$^i$, —SO$_2$R$^i$, —S—R$^i$, —R$^{ii}$, —R$^{iii}$, wherein $R^i$ is H, $C_{1-4}$ alkyl, $C_{1-4}$ haloalkyl, $C_{1-4}$ di-haloalkyl, $C_{1-4}$ tri-haloalkyl, $C_{1-4}$ perfluoro-alkyl, aryl, halogen, $C_{1-4}$ alkenyl;

$R^{ii}$ is a fused ring with the phenyl residue selected in the group of:

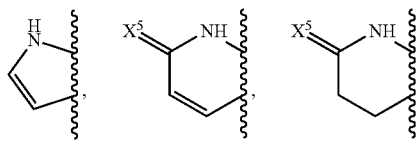

$X^5$ is S, SO$_2$, SO, O.

$R^{iii}$ is ($C_1$-$C_4$)-halo alkyl, $C_{1-4}$ di-haloalkyl, ($C_1$-$C_4$)-tri-haloalkyl, ($C_1$-$C_4$)-perfluoro-alkyl, CF$_2$CF$_3$.

$R^5$ is H, $C_1$-$C_4$-alkyl;

$R^4$ is H, F, Cl, I or Br;

$R^2$ and $R^3$ are the same or different and each independently H, $C_{1-4}$ alkyl, —CN, carbamoyl methyl, —NO$_2$, halogen, $C_{1-4}$ alkoxy, $C_{1-4}$ alkanoyl, $C_{1-4}$ thio-alkyl, $C_{1-4}$ alkyl-sulphinyl, $C_{1-4}$ alkyl-sulphonyl, $C_{1-4}$ perfluoro-alkyl, $C_{1-4}$ perfluoro-thio-alkyl, $C_{1-4}$ perfluoro-alkyl-sulphinyl, $C_{1-4}$ perfluoro-alkyl-sulphonyl, with the condition that the $C_{1-4}$ alkyl, the $C_{1-4}$ alkoxy, the $C_{1-4}$ alkanoyl, the $C_{1-4}$ thio-alkyl, the $C_{1-4}$ alkyl-sulphinyl, the $C_{1-4}$ alkyl-sulphonyl, the $C_{1-4}$ perfluoro-alkyl, the $C_{1-4}$ perfluoro-thio-alkyl, the $C_{1-4}$ perfluoro-alkyl-sulphinyl, the $C_{1-4}$ perfluoro-alkyl-sulphonyl are optionally and each bound to a $C_{1-4}$ alkyl, a phenyl, a thio-phenyl, a sulphinyl-phenil, a sulphunyl-phenyl.

Preferably R is selected in the group consisting of: aryl, optionally substituted aryl, heteroaryl, optionally substituted heteroaryl, straight or branched $C_{2-10}$ alkyl, substituted straight or branched $C_{1-12}$ alkyl, straight or branched $C_{2-10}$ heteroalkyl, substituted straight or branched $C_{2-10}$ heteroalkyl, $C_1$-$C_4$-arylalkyl, substituted $C_1$-$C_4$-arylalkyl, $C_{1-4}$ heteroarylalkyl, substituted $C_{1-4}$ heteroarylalkyl;

X is oxygen (—O—), sulfur (—S—), sulfinyl (—SO—), sulfonyl (—SO$_2$—);

$R^1$ and $R^6$ are the same or different and each independently are H, $C_{1-4}$ alkyl, halogen, —NO$_2$, —CN, —SiRi$_3$, —NHCOCF$_3$, —NHCOR$^i$, —NHCONHR$^i$, —NHCOOR$^i$, —OCONHR$^i$, —CONHR$^i$, —NHCSCF$_3$, —NHCSR$^i$, —NHSO$_2$R$^i$, —NCS—OR$^i$, —COR$^i$, —COOR$^i$, —OSO$_2$R$^i$, —SO$_2$R$^i$, —S—R$^i$, —R$^{ii}$, —R$^{iii}$, wherein $R^i$ is H, $C_{1-4}$ alkyl, $C_{1-4}$ haloalkyl, $C_{1-4}$ di-haloalkyl, $C_{1-4}$ tri-haloalkyl, $C_{1-4}$ perfluoro-alkyl, aryl, halogen, $C_{1-4}$ alkenyl;

$R^{ii}$ a fused ring with the phenyl residue selected in the group of:

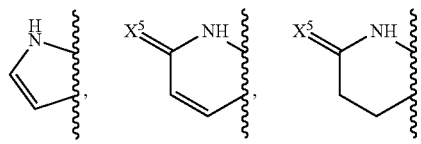

$X^5$ is S, SO$_2$, SO, O.

$R^{iii}$ is ($C_1$-$C_4$)-halo alkyl, $C_{1-4}$ di-haloalkyl, ($C_1$-$C_4$)-tri-haloalkyl, ($C_1$-$C_4$)-perfluoro-alkyl, CF$_2$CF$_3$.

Preferably R is selected in the group consisting of: aryl, optionally substituted aryl, heteroaryl, optionally substituted heteroaryl, straight or branched $C_{2-10}$ alkyl, substituted straight or branched $C_{1-12}$ alkyl, straight or branched $C_{2-10}$ heteroalkyl, substituted straight or branched $C_{2-10}$ heteroalkyl, $C_1$-$C_4$-arylalkyl, substituted $C_1$-$C_4$-arylalkyl, heteroarylalkyl, substituted $C_{1-4}$ heteroarylalkyl;

X is oxygen (—O—), sulfur (—S—), sulfinyl (—SO—), sulfonyl (—SO$_2$—);

$R^1$ and $R^6$ are the same or different and each independently are H, $C_{1-4}$ alkyl, halogen, —NO$_2$, —CN, —SiRi$_3$, —NHCOCF$_3$, —NHCOR$^i$, —NHCONHR$^i$, —NHCOOR$^i$, —OCONHR$^i$, —CONHR$^i$, —NHCSCF$_3$, —NHCSR$^i$, —NHSO$_2$R$^i$, —NCS—OR$^i$, —COR$^i$, —COOR$^i$, —OSO$_2$R$^i$, —SO$_2$R$^i$, —S—R$^i$, —R$^{ii}$, —R$^{iii}$, wherein $R^i$ is H, $C_{1-4}$ alkyl, $C_{1-4}$ haloalkyl, $C_{1-4}$ di-haloalkyl, $C_{1-4}$ tri-haloalkyl, $C_{1-4}$ perfluoro-alkyl, aryl, halogen, $C_{1-4}$ alkenyl;

$R^{ii}$ a fused ring with the phenyl residue selected in the group of:

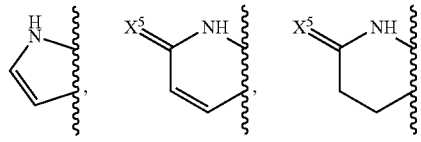

$X^5$ is S, SO$_2$, SO, O.

$R^{iii}$ is ($C_1$-$C_4$)-halo alkyl, $C_{1-4}$ di-haloalkyl, ($C_1$-$C_4$)-tri-haloalkyl, ($C_1$-$C_4$)-perfluoro-alkyl, CF$_2$CF$_3$.

$R^2$ and $R^3$ are the same or different and each independently H, $C_{1-4}$ alkyl, —CN, carbamoyl methyl, —NO$_2$, halogen, $C_{1-4}$ alkoxy, $C_{1-4}$ alkanoyl, $C_{1-4}$ thio-alkyl, $C_{1-4}$ alkyl-sulphinyl, $C_{1-4}$ alkyl-sulphonyl, $C_{1-4}$ perfluoro-alkyl, $C_{1-4}$ perfluoro-thio-alkyl, $C_{1-4}$ perfluoro-alkyl-sulphinyl, $C_{1-4}$ perfluoro-alkyl-sulphonyl.

Preferably R is selected in the group consisting of: aryl, optionally substituted aryl, heteroaryl, optionally substituted heteroaryl, straight or branched $C_{2-10}$ alkyl, substituted straight or branched $C_{1-12}$ alkyl, straight or branched $C_2$-$C_{10}$ heteroalkyl, substituted straight or branched $C_{2-10}$ heteroalkyl, $C_1$-$C_4$-arylalkyl, substituted $C_1$-$C_4$-arylalkyl, $C_{1-4}$ heteroarylalkyl, substituted $C_{1-4}$ heteroarylalkyl;

$R^5$ is H, $C_1$-$C_4$-alkyl;
$R^4$ is H, F, Cl, I or Br;
$R^2$ and $R^3$ are the same or different and each independently —CN, —$NO_2$, halogen, $C_{1-4}$ alkoxy, $C_{1-4}$ thio-alkyl, $C_{1-4}$ perfluoro-alkyl.

Preferably R is selected in the group consisting of: $C_{2-4}$ alkyl, aryl, $C_1$-$C_4$-arylalkyl, substituted $C_1$-$C_4$-arylalkyl, $C_{1-4}$ heteroarylalkyl, substituted $C_{1-4}$ heteroarylalkyl;

$R^1$ and $R^6$ are the same or different and each independently are halogen, —$NO_2$, —CN, —$R^{iii}$, wherein $R^{iii}$ is $(C_1$-$C_4)$-halo alkyl, $C_{1-4}$ di-haloalkyl, $(C_1$-$C_4)$-tri-haloalkyl, $CF_2CF_3$.

Preferably R is selected in the group consisting of: $C_{2-4}$ alkyl, aryl, $C_1$-$C_4$-arylalkyl, substituted $C_1$-$C_4$-arylalkyl, $C_{1-4}$ heteroarylalkyl, substituted $C_{1-4}$ heteroarylalkyl;

$R^1$ is halogen, —$NO_2$, —CN, —$R^{iii}$, wherein $R^{iii}$ is $(C_1$-$C_4)$-halo alkyl, $C_{1-4}$ di-haloalkyl, $(C_1$-$C_4)$-tri-haloalkyl, $CF_2CF_3$.

$R^6$ is H.

Preferably R is selected in the group consisting of: $C_{2-4}$ alkyl, aryl, $C_1$-$C_4$-arylalkyl, substituted $C_1$-$C_4$-arylalkyl, $C_{1-4}$ heteroarylalkyl;

$R^1$ is halogen, —$NO_2$, —CN;
$R^5$ is H, $C_1$-$C_4$-alkyl;
$R^2$ is —CN, —$NO_2$, halogen, $C_{1-2}$ perfluoro-alkyl.
$R^3$ is —CN, —$NO_2$, halogen, $C_{1-2}$ perfluoro-alkyl.

Preferably R is selected in the group consisting of: $C_{2-4}$ alkyl, phenyl, $C_1$-$C_2$-arylalkyl, substituted $C_1$-$C_2$-arylalkyl, $C_{1-2}$ heteroarylalkyl;

X is —S—, —$SO_2$—, —O—;
$R^1$ is halogen, —CN;
$R^5$ is H;
$R^4$ is H;
$R^2$ is —CN, —$NO_2$, halogen, $C_{1-2}$ perfluoro-alkyl.
$R^3$ is —CN, —$NO_2$, halogen, $C_{1-2}$ perfluoro-alkyl.

Preferably R is selected in the group consisting of: $C_{2-4}$ alkyl, phenyl, $C_1$-$C_2$-arylalkyl, substituted $C_1$-$C_2$-arylalkyl, $C_{1-2}$ heteroarylalkyl;

$R^1$ is in para position with respect to X;
$R^2$ is —CN, —$NO_2$;
$R^3$ is halogen, $C_{1-2}$ perfluoro-alkyl;

Preferably the compound is represented by the following stereoisomer structure:

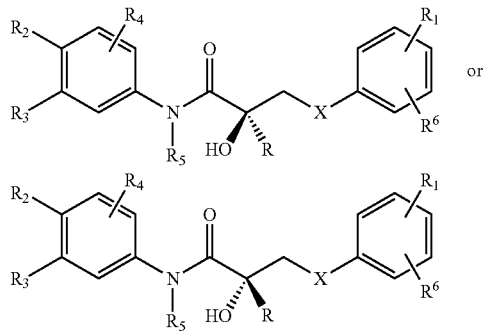

wherein the substituents are defined as in claim 1.
Preferably the compound has the formula III or IV:

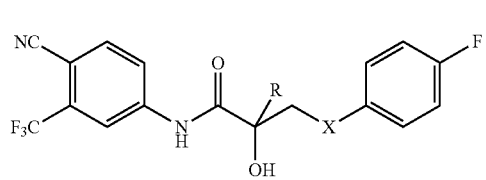

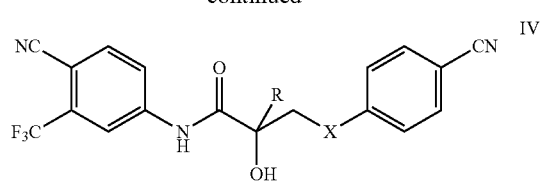

Wherein R is H or aryl, optionally substituted aryl, heteroaryl, optionally substituted heteroaryl, straight or branched $C_{1-10}$ alkyl, substituted straight or branched $C_{1-12}$ alkyl, straight or branched $C_{1-10}$ heteroalkyl, substituted straight or branched $C_{1-12}$ heteroalkyl, $C_1$-$C_4$-arylalkyl, substituted $C_1$-$C_4$-arylalkyl, $C_{1-4}$ heteroarylalkyl, substituted $C_{1-4}$ heteroarylalkyl.

X is oxygen, sulfur, sulfinyl (—SO—), sulfonyl (—$SO_2$—) imino (—NH—) or alkylimino (—NR''—), (—PR''—), —Se—, where R'' is H, $C_1$-$C_4$ alkyl.

Preferably the compound is selected from the following structures:

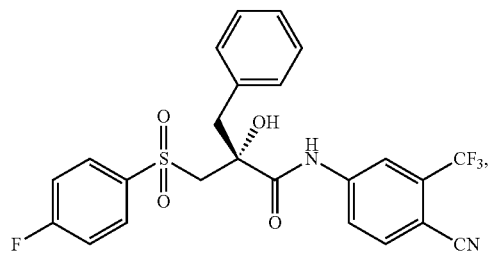

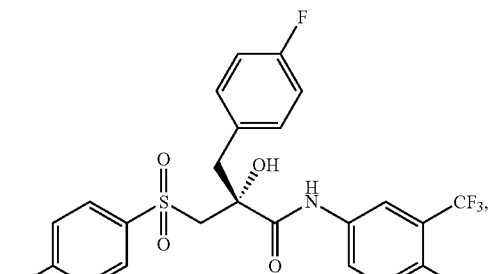

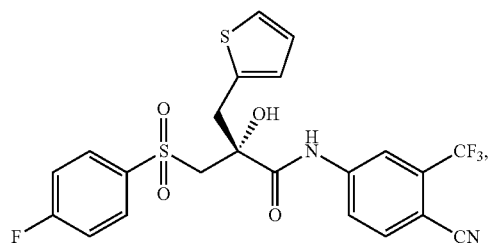

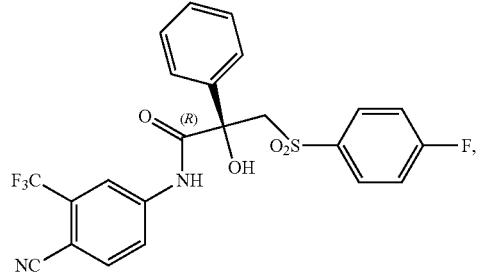

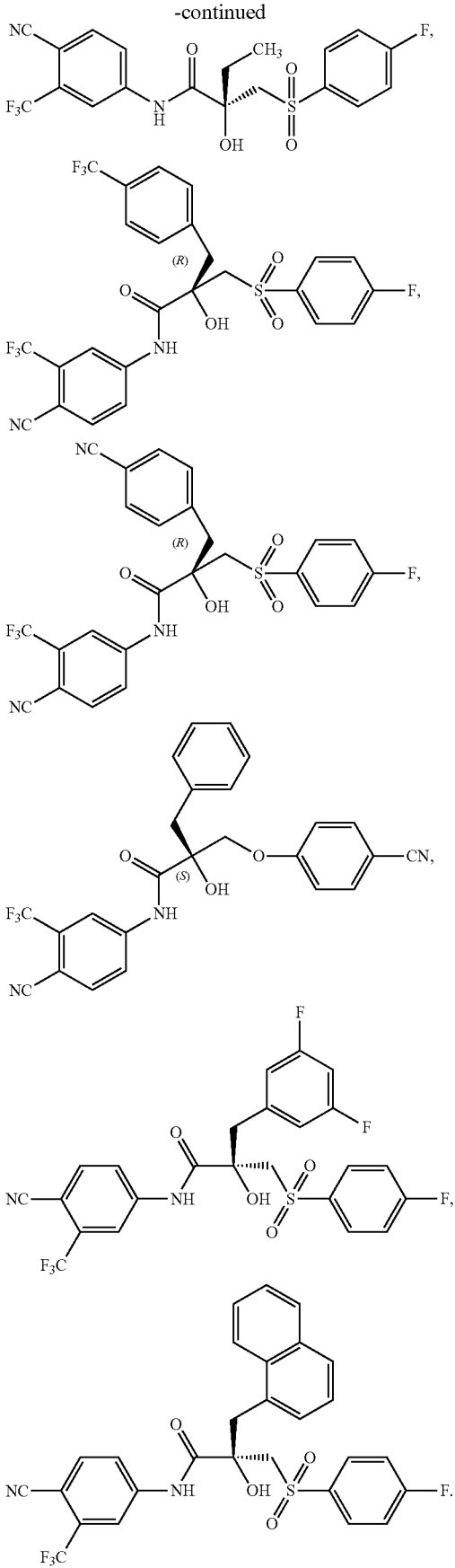

Preferably the compound is a selective androgen receptor modulator (SARM).

Preferably the compound is for medical use.

Preferably for use as an anti-tumoral agent.

Preferably for use as an anti-tumoral agent for prostate cancer.

It is a further object of the invention a pharmaceutical composition comprising the compound of the invention and/or its isomer, pharmaceutically acceptable salts, crystal or N-oxide, hydrate or any combination thereof.

It is a further object of the invention a method for the preparation of a compound of the invention comprising:

a protecting step during which the compound of general formula XXXV (XXXV)

wherein $R^{35}$ is R or $CH_2COOH$, is reacted with a compound of general formula XXXVI (XXXVI)

wherein $R^7$ and $R^8$ can be the same or different and both can be independently form each other H, $C_1$-$C_6$ alkyl, in order to obtain a compound of general formula XXXVII (XXXVII)

an electrophilic substitution step, where the compound of general formula XXXVII is reacted, under basic conditions, with a reactant whose synthetic equivalent has the general formula XXXVIII $R^{36(+)}$ (XXXVIII)

the reaction provides an intermediate of general formula IXC (IXC)

wherein, $R^{36}$ is R, $CH_2$—$X^3$, wherein $X^3$ is halogen, —OH, —$OR^{iv}$, wherein $R^{iv}$ is $SO_2CH_3$, $SO_2$-p-$CH_3$-—$C_6H_5$, $C_1$-$C_4$-alkyl, $C_1$-$C_4$-arylalkyl, —$COR^v$, —$COOR^v$, wherein $R^v$ is $C_1$-$C_4$-alkyl;

a deprotection step, during with the fragment XXXVI is removed;

a nucleophylic substitution step, during which —$X^3$ is substituted with the fragment

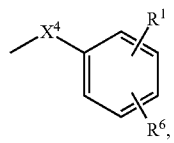

wherein $X^4$ is —S—, —$SO_2$—, —SO—, —O—, —NR″, —Se—, —PR″ a coupling step with an amine of general formula XC which is reacted with the free carboxylic acid or its ester.

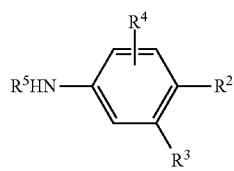

(XC)

Wherein when $X^4$ is —S—, the process comprises an oxidation so that X will be —SO— or —$SO_2$—.

According to one embodiment, when $R^{35}$ is R and $R^{36}$ is $CH_2$—$X_3$, compound of general formula IXC, presents the general formula VIII

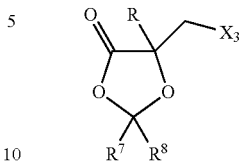

(VIII)

According to a specific embodiment, $X^3$ is halogen and in particular is Br.

Preferably when $R^{35}$ is $CH_2COOH$, $R^{36}$ is R and the intermediate of formula IXC is reacted under halogen-decarboxilative conditions, the compound of formula VIII is obtained

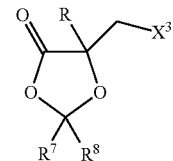

(VIII)

Preferably the method is according to Scheme 1:

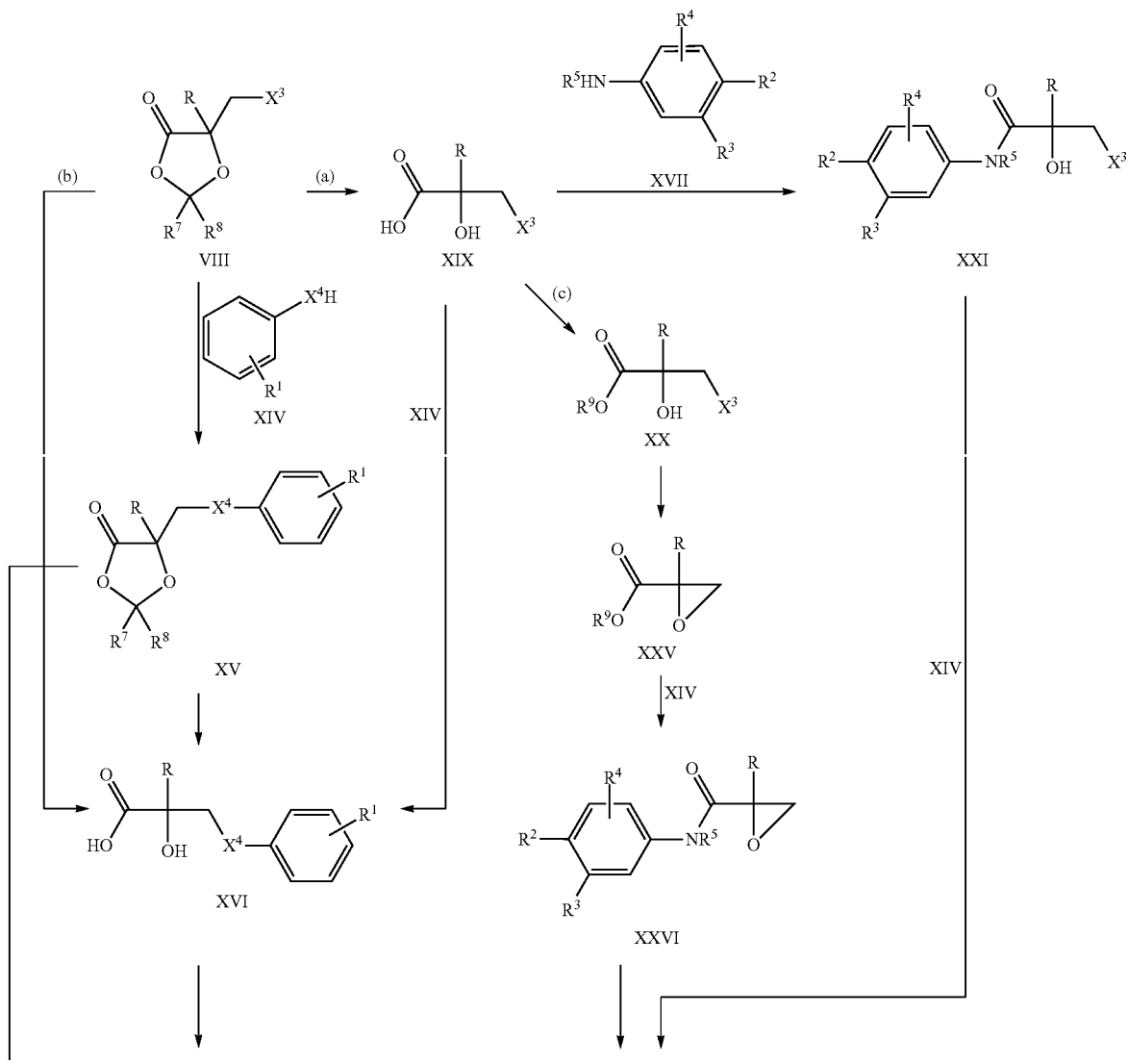

-continued

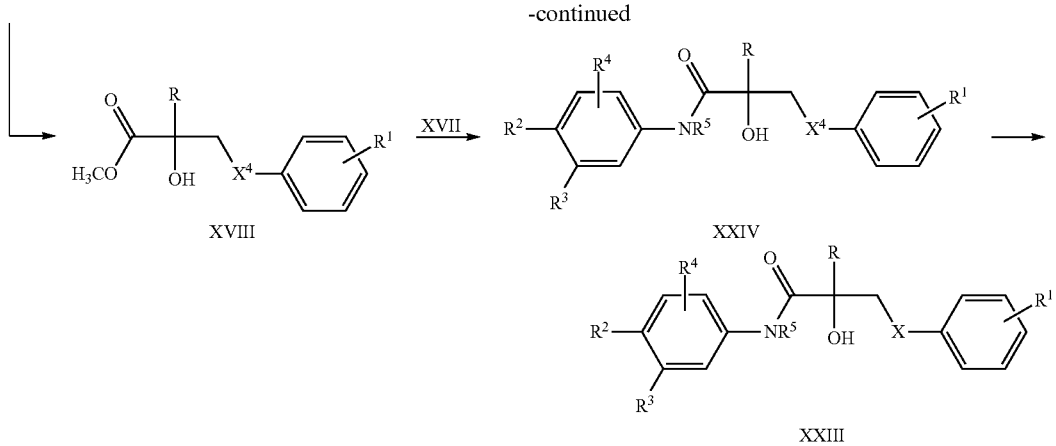

Wherein the compounds of general formula VIII can be obtained according to the following reaction scheme 2:

LG is a leaving group and is halogen, —OR$^{vi}$. R$^{vi}$ is —SO$_2$CH$_3$ or —SO$_2$-p-CH$_3$—C$_6$H$_5$.

Scheme 2

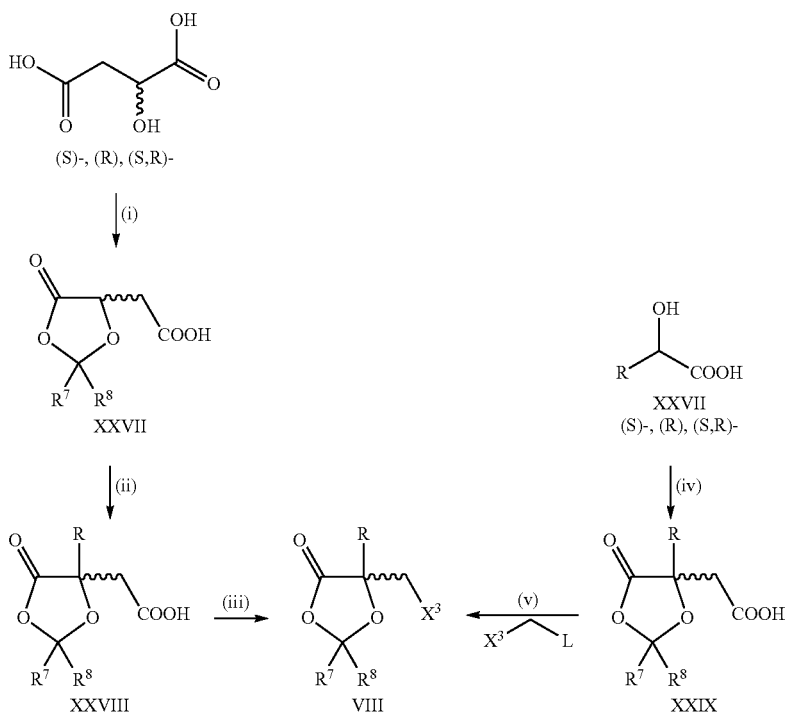

wherein,

R$^7$ and R$^8$ are, one independently from the other, H, C$_1$-C$_6$-alkyl. According to specific embodiments, R$^6$ is H and R$^7$ is tert-butyl; according to specific embodiments, R$^6$ is H and R$^7$ is iso-butyl.

X$^3$ is a leaving group. According to specific embodiments, X$^3$ is halogen, —OH, —OR$^{iv}$; R$^{iv}$ is —SO$_2$CH$_3$, —SO$_2$-p-CH$_3$—C$_6$H$_5$, C$_1$-C$_4$-alkyl, C$_1$-C$_4$-arylalkyl, —COR$^v$, —CO-OR$^v$, wherein R$^v$ is C$_1$-C$_4$-alkyl;

Wherein in Scheme 2: steps (i) and (iv) are either protection reactions or introduction of chiral auxiliaries; steps (ii) and (v) are alkylations, while step (iii) is a decarboxylative halogenation reaction.

Preferably wherein R$^{35}$ is —CH$_2$COOH, R$^{36}$ is R, and the second protected intermediate IXC is reacted under decarboxylative halogenation; X$^3$ is an halogen.

Preferably R$^{35}$ is R, R$^{36}$ is CH$_2$—X$^3$; the electrophilyc substitution step leads directly to the cyclic intermediate VIII.

Preferably the protection steps occur under acid catalysis; R$^7$ è —H and R$^8$ is a C$_1$-C$_4$ alkyl; the reactant whose synthetic equivalent has formula XXXVIII, has formula

LG-R$^{36}$ wherein LG is a leaving group;
wherein the deprotection step occurs in presence of acidic water;

wherein during the nucleophylic substitution a compound of general formula XIV is reacted

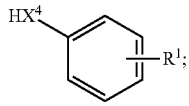

(XIV)

Wherein the amine coupling step consists of a preliminary activation step, during which, before the reaction with the amine XC, the substrate is treated with $SOCl_2$; $X^3$ is an halogen.

Preferably $R^7$ is H and $R^8$ is tert-butyl, iso-butyl;

LG is halogen, —$OR^{vi}$, wherein $R^{vi}$ is mesyl (—$SO_2CH_3$), tosyl (—$SO_2$-$pCH_3$—$C_5H_6$);

wherein the nucleophylic substitution step occur under basic conditions.

In one embodiment, this invention provides a method of delaying the progression of prostate cancer in a subject suffering from prostate cancer, comprising the step of administering to said subject a compound of formula (I) and/or its isomer, pharmaceutically acceptable salt, pharmaceutical product, crystal, N-oxide, hydrate or any combination thereof, or a composition comprising the same in an amount effective to delay the progression of prostate cancer in the subject.

In one embodiment, this invention provides a method for treating a hyperproliferative disorder comprising administering such a pharmaceutical composition to a subject in need of such treatment, thereby treating the hyperproliferative disorder. The hyperproliferative disorder may be hormone refractory prostate cancer.

In one embodiment, the present invention provides a composition comprising a compound of formula (I) and/or its isomer, pharmaceutically acceptable salts, pharmaceutical product, crystal or N-oxide, hydrate or any combination thereof. In one embodiment, the compound is a selective androgen receptor modulator (SARM).

In one embodiment, the SARM is a partial antagonist. In one embodiment, the SARM is a partial agonist, or in some embodiments, a tissue-selective agonist.

In one embodiment, this invention provides a method of contraception in a male subject, comprising the step of administering to the subject a compound of formula (I) and/or its isomer, pharmaceutically acceptable salt, pharmaceutical product, crystal, N-oxide, hydrate or any combination thereof, or a composition comprising the same, in an amount effective to suppress sperm production in the subject, thereby effecting contraception in the subject.

In one embodiment, this invention provides a method of hormone therapy comprising the step of contacting an androgen receptor of a subject with a compound of formula (I) and/or its isomer, pharmaceutically acceptable salt, pharmaceutical product, crystal, N-oxide, hydrate or any combination thereof, or a composition comprising the same, in an amount effective to effect a change in an androgen-dependent condition.

In one embodiment, this invention provides a method of treating a bone-related disorder in a subject, or increasing a bone mass in a subject, promoting bone formation in a subject, administering an effective amount of a compound of formula (I) and/or its isomer, pharmaceutically acceptable salt, pharmaceutical product, crystal, N-oxide, hydrate or any combination thereof, or a composition comprising the same, in an amount effective to treat said bone-related disorder.

According to this aspect, and in one embodiment, the subject suffers from osteoporosis, osteopenia, bone fracture, bone frailty, loss of bone mineral density (HMD), or any combination thereof. In one embodiment, the method increases the strength of a bone of said subject. In one embodiment, the compound stimulates or enhances osmioblasiogenesis, or in another embodiment the compound inhibits osteoclast proliferation.

In one embodiment, this invention provides a method of treating, reducing the incidence of, delaying progression of, reducing the severity of or alleviating symptoms associated with a muscle wasting disorder in a subject, comprising the step of administering to said subject a compound of formula (I) and/or its isomer, pharmaceutically acceptable sail, pharmaceutical product, crystal, N-oxide, hydrate or any combination thereof, or a composition comprising the same, in an amount effective to treat the muscle wasting disorder in said subject.

According to this aspect, and in one embodiment, the muscle wasting disorder is due a pathology, illness, disease or condition. In one embodiment, the pathology, illness, disease or condition is neurological, infectious, chronic or genetic. In one embodiment, the pathology, illness, disease or condition is a muscular dystrophy, a muscular atrophy. X-linked spinal-bulbar muscular atrophy (SBMA), a Cachexia, malnutrition, leprosy, diabetes, renal disease, chronic obstructive pulmonary disease (COPD), cancer, end stage renal failure, sarcopenia, emphysema, osteomalacia, HIV infection. AIDS, or cardiomyopathy.

In one embodiment, the muscle wasting disorder is an age-associated muscle wasting disorder; a disuse deconditioning-associated muscle wasting disorder; or the muscle wasting disorder is due to chronic lower back pain; burns; central nervous system (CNS) injury or damage; peripheral nerve injury or damage; spinal cord injury or damage; chemical injury or damage or alcoholism.

In one embodiment, this invention provides a method of treating, reducing the severity of reducing the incidence of delaying the onset of or reducing pathogenesis of diabetes in a human subject, comprising administering an effective amount of a compound of formula (I) and/or its isomer, pharmaceutically acceptable salt, pharmaceutical product, crystal, N-oxide, hydrate or any combination thereof, to said subject.

In one embodiment, this invention provides, a method of treating, reducing the severity of, reducing the incidence of, delaying the onset of, or reducing pathogenesis of glucose intolerance in a human subject, comprising the step of administering an effective amount of a compound of formula (I) and/or its isomer, pharmaceutically acceptable salt, pharmaceutical product, crystal, N-oxide, hydrate or any combination thereof, to said subject.

In one embodiment, this invention provides a method of treating, reducing the severity of, reducing the incidence of, delaying the onset of, or reducing pathogenesis of hyperinsulinemia in a human subject, comprising the step of administering an effective amount of a compound of formula (I) and/or its isomer, pharmaceutically acceptable salt, pharmaceutical product, crystal, N-oxide, hydrate or any combination thereof, to said subject.

In one embodiment, this invention provides a method of treating, reducing the severity of, reducing the incidence of, delaying the onset of or reducing pathogenesis of insulin resistance in a human subject, comprising the step of administering an effective amount of a compound of formula (I)

and/or its isomer, pharmaceutically acceptable salt, pharmaceutical product, crystal, N-oxide, hydrate or any combination thereof, to said subject.

In one embodiment, this invention provides a method of treating, reducing the severity of, reducing the incidence of delaying the onset of, or reducing pathogenesis of diseases associated with diabetes comprising the step of administering an effective amount of a compound of formula (I) and/or its isomer, pharmaceutically acceptable salt, pharmaceutical product, crystal, N-oxide, hydrate or any combination thereof, to said subject.

In one embodiment, this invention provides a method of treating, reducing the severity of, reducing the incidence of, delaying the onset of, or reducing pathogenesis of fatty liver conditions in a human subject, comprising the step of administering an effective amount of a compound of formula (I) and/or its isomer, pharmaceutically acceptable sail, pharmaceutical product, crystal, N-oxide, hydrate or any combination thereof, to said subject In one embodiment, this invention provides a method of treating, reducing the severity of, reducing the incidence of, delaying the onset of, or reducing the pathogenesis of cardiovascular disease in a human subject, comprising the step of administering an effective amount of a compound of formula (I) and/or its isomer, pharmaceutically acceptable salt, pharmaceutical product, crystal, N-oxide, hydrate or any combination thereof to said subject.

In one embodiment, this invention provides a method of treating, reducing the severity of, reducing the incidence of, delaying the onset of, or reducing the pathogenesis of cachexia in a subject, comprising the step of administering an effective amount of a compound of formula (I) and/or its isomer, pharmaceutically acceptable salt, pharmaceutical product crystal, TV-oxide, hydrate or any combination thereof to said subject.

In one embodiment this invention provides a method of treating a disease or condition of the eye of a subject, comprising the step of administering an effective amount of a compound of formula (I) and/or its isomer, pharmaceutically acceptable salt, pharmaceutical product, crystal, A/-oxide, hydrate or any combination thereof, to the subject. In one embodiment, the disease or condition of the eye comprises Sjogren's syndrome, or xerophthalmia.

In one embodiment, the present invention provides a method of reducing a fat mass in a subject comprising the step of administering an effective amount of a compound of formula (1) and/or its isomer, pharmaceutically acceptable salt, pharmaceutical product, crystal, TV-oxide, hydrate or any combination thereof, to the subject.

In one embodiment the present invention provides a method of increasing a lean mass in a subject comprising the step of administering an effective amount of a compound of formula (1) and/or its isomer, pharmaceutically acceptable salt, pharmaceutical product, crystal, N-oxide, hydrate or any combination thereof, to the subject.

In another embodiment, this invention provides a method of treating reducing the severity of, reducing the incidence of, delaying the onset of, or reducing pathogenesis of cachexia in a subject, comprising the step of administering to said subject a compound of formula (I) and/or its isomer, pharmaceutically acceptable salt pharmaceutical product, crystal, N-oxide, hydrate or any combination thereof, to the subject.

In embodiment the cachexia is associated with cancer in said subject.

In another embodiment, this invention provides a method of treating reducing the severity of reducing the incidence of, delaying the onset of, or reducing pathogenesis of rheumatoid arthritis in a subject, comprising the step of administering to said subject a compound of formula (I) and/or its isomer pharmaceutically acceptable salt, pharmaceutical product, crystal, N-oxide, hydrate or any combination thereof, to the subject.

In another embodiment this invention provides a method of treating reducing the severity of reducing the incidence of delaying the onset of or reducing pathogenesis of chronic kidney disease in a subject, comprising the step of administering to said subject a compound of formula (I) and/or its isomer, pharmaceutically acceptable salt, pharmaceutical product crystal, N-oxide, hydrate or any combination thereof, to the subject.

In another embodiment this invention provides a method of treating reducing the severity of reducing die incidence of delaying the onset of or reducing pathogenesis of end stage renal disease in a subject comprising the step of administering to said subject a compound of formula (I) and/or its isomer, pharmaceutically acceptable salt, pharmaceutical product crystal, N-oxide, hydrate or any combination thereof, to the subject.

In another embodiment, this invention provides a method of treating reducing the severity of reducing the incidence of, delaying the onset of, or reducing pathogenesis of frailty in a subject comprising the step of administering to said subject a compound of formula (I) and/or its isomer, pharmaceutically acceptable sail, pharmaceutical product crystal, N-oxide, hydrate or any combination thereof, 10 the subject.

In another embodiment this invention provides a method of treating reducing the severity of reducing the incidence of, delaying the onset of, or reducing pathogenesis of hypogonadism in a subject, comprising the step of administering to said subject a compound of formula (I) and/or its isomer, pharmaceutically acceptable salt, pharmaceutical product, crystal, N-oxide, hydrate or any combination thereof, 10 the subject.

In another embodiment this invention provides a method of treating reducing the severity of reducing the incidence of delaying the onset of or reducing pathogenesis of age-related functional decline in a subject comprising the step of administering to said subject a compound of formula (I) and/or its isomer, pharmaceutically acceptable salt, pharmaceutical product, crystal, N-oxide, hydrate or any combination thereof, to the subject In another embodiment, this invention provides a method of suppressing spermatogenesis; contraception in a male; hormone therapy; treating prostate cancer; delaying the progression of prostate cancer; treating a bone-related disorder in a subject, or increasing a bone mass in a subject and/or promoting bone formation in a subject; treating, reducing the incidence of, delaying progression of, reducing the severity of, or alleviating symptoms associated with a muscle wasting disorder; treating, reducing the severity of, reducing the incidence of, delaying the onset of, or reducing pathogenesis of diabetes; treating, reducing the severity of, reducing the incidence of, delaying the onset of, or reducing pathogenesis of glucose intolerance; treating, reducing the severity of, reducing the incidence of, delaying the onset of, or reducing pathogenesis of hyperinsulinemia; treating, reducing the severity of, reducing the incidence of, delaying the onset of, or reducing pathogenesis of insulin resistance; treating, reducing the severity of, reducing the incidence of, delaying the onset of, or reducing pathogenesis of diseases associated with diabetes; treating, reducing the severity of, reducing the incidence of, delaying the onset of, or reducing pathogenesis of fatty liver conditions: treating, reducing the severity of, reducing the incidence of, delaying the onset of, or reducing pathogenesis of cardiovascular disease; treating reducing the severity of, reducing the incidence of, delaying the onset of, or reducing pathogenesis of cachexia; treating a disease or condition of the eye; reducing a fat mass; or increasing a lean mass in a subject, comprising the step of administering an effective amount of a compound of formula and/or its isomer, pharmaceutically acceptable salt pharmaceutical product, crystal, N-oxide, hydrate or any combination thereof, to the subject as herein described. Compounds belonging to formula I can be formulated in a known fashion, for parenteral administration, for injection or for continue administration. The injection preparation can be kept in mono-dose vials, or in multi vials case with additives.

The pharmaceutical composition can be as a suspension, an aqueous liquid on oil. All these formulation can contain dispersion additives or stabilizers. Alternatively, the compound can be a solid to be dissolved just before the use. The compounds of general formula I can be also formulated for rectal administration as suppositories or enemas, In this case formulations can contain known additives such as cocoa butter or other glycosides.

The compounds of general formula I can also be formulated in a know fashion for long release treatment. These long release formulations can be administered by an under-skin or intra-muscular implantation. Thus, compounds of formula I can be formulated in a known fashion with polymers, ionic-exchange resins or as low soluble salts. For intra-nose administration, compounds of general formula I can be formulated in a know fashion as powder together with a right transporter.

Dosages of compounds of formula I will depend also on patients age and on their general clinical conditions, thus the right dosage will be decided, case by case, from the doctor. The dosage will also depend on the compound used and on the administration manner. Commonly used dosages are comprised form 0.1 mg/Kg and 400 mg/Kg day.

Compounds of general formula I can be administered together with other known compounds.

The terms employed herein have the following meanings:

The term "pharmaceutically acceptable salts" as used herein include the acid addition salts (formed with the free amino groups of the starting compound) which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium potassium, ammonium, calcium, or ferric hydroxides, and such organic bases as isopropylamine, triethylamine, 2-ethylamoni ethanol, and the like.

The term "prodrug" as used herein is referred to a compound which is converted in vivo to the corresponding active ingredient.

The term "halo" or "halogen" as employed herein as such or as a part of another group, refers to chlorine, bromine, fluorine or iodine.

The term "$(C_x\text{-}C_y)$alkyl", as employed herein as such or as a part of another group, refers to a straight, branched or cyclized chain radical having x to y carbon atoms. Representative example for $(C_x\text{-}C_y)$alkyl include, but are not limited to, methyl, ethlyl, n-propyl, n-butyl, n-propyl, isobutyl, sec-butyl, tert-butyl, n-pentyl, isopentyl neopentil, n-hexyl, cyclopentyl, cyclohexyl and the like.

The term "$(C_x\text{-}C_y)$heteroalkyl", as employed herein as such or as a part of another group, refers to a straight, branched or cyclized chain radical having x to y atoms where at least one is an heteroatom such as —N—, —O—, —S—, —NR$^g$, —SO$_2$— where R$^g$ is H or $(C_1\text{-}C_4)$alkyl as defined herein.

The term "$(C_x\text{-}C_y)$alkenyl", as employed herein as such or as a part of another group, refers to a straight, branched or cyclized chain radical having x to y carbon atoms, containing (a) double bond(s).

The term "hydroxy", as employed herein as such or as a part of another group, refers to an —OH group.

The term "hydroxy$(C_x\text{-}C_y)$alkyl", as employed herein, refers to at least one hydroxy group as defined herein, appended to the parent molecular moiety though an $(C_1\text{-}C_7)$ alkyl group, as defined herein. Representative examples of hydroxy$(C_x\text{-}C_y)$alkyl include, but are not limited to, hydroxymethyl, 2,2-dihydroxyethyl, 1-hydroxyethyl, 3-hydroxypropyl, 1-methyl-1-hydroxypropyl, and the like.

The term "cyano", as employed herein as such or as a part of another group, refers to an —CN group.

The term "amino", as employed herein as such or as a part of another group, refers to an —NH$_2$ group.

The term "nitro", as employed herein as such or as a part of another group, refers to an —NO$_2$ group.

The term "carbamoyl methyl", as employed herein as such or as a part of another group, refers to a —CH$_2$—CONH$_2$ group.

The term "per-fluoro", as employed herein refers to a group bearing a $(C_x\text{-}C_y)$alkyl, which will be completely substituted with fluorine atoms. Representative, but not exclusive examples of per-fluorinated compounds are —CF$_3$ or —S—CF$_2$—CF$_3$.

The term "alkyl-thio", as employed herein refers to a —SR$^m$ group, where R$^m$ is an alkyl group as defined herein.

The term "alkyl-sulfinyl", as employed herein refers to a —SOR$^m$ group, where R$^m$ is an alkyl group as defined herein.

The term "alkyl-sulfonyl", as employed herein refers to a —SO$_2$R$^m$ group, where R$^m$ is an alkyl group as defined herein.

The term "mono- or di(Ci-C7)alkyl amino", as employed herein as such or as part of another group, refers to one or two $(C_1\text{-}C_7)$alkyl group(s), as defined herein, appended to the parent molecular moiety through an amino group, as defined herein. Representative examples of mono- or di$(C_1\text{-}C_7)$alkyl amino include, but are not limited to methylamino, ethylamino, propylamino, butylamino, dimethylamino, diethylamino, and the like.

The term "$(C_1\text{-}C_7)$alkoxy", as employed herein as such or as part of another group, refers to —O—$(C_1\text{-}C_7)$alkyl, wherein —$(C_1\text{-}C_7)$alkyl is as defined herein. Representative examples of $(C_1\text{-}C_7)$alkoxy include, but are not limited to methoxy, ethoxy, propoxy, butoxy, isobutoxy, sec-butoxy, tert-butoxy, and the like.

The term "$(C_1\text{-}C_7)$alkoxy$(C_1\text{-}C_7)$alkyl", as employed herein, refers to at least one $(C_1\text{-}C_7)$alkoxy group, as defined herein, appended to the parent molecular moiety through an (C1-C7)alkyl group, as defined herein. Representative examples of (Ci-C7)alkoxy(Ci-C7)alkyl include, but are not limited to methoxymethyl, ethoxymethyl, 2-methoxyethyl, 2-ethoxyethyl, 3,3-dimethoxypropyl, 2,4-dimethoxybutyl and the like.

The term "$(C_2\text{-}C_7)$acyl" as employed herein by itself or as part of another group refers to alkylcarbonyl or alkenylcarbonyl group having 2 to 7 carbon atoms, and examples thereof include acetyl, propanoyl, isopropanoyl, butanoyl, sec-butanoyl, tert-butanoyl and pentanoyl.

The term "$(C_2\text{-}C_7)$acyl amino" as employed herein by itself or as part of another group refers to a group having formula —NCO—$(C_2\text{-}C_7)$acyl.

The term "silane" as employed herein by itself or as part of another group refers to a group having formula —SiR$^d$R$^e$R$^f$, where $R^d$, $R^e$ and $R^f$ are chosen, one independently from the other, among H, phenyl or $(C_1-C_4)$alkyl.

The term "aryl" as employed herein as such or as a part of another group, refers to an aromatic carbocyclic ring system having a single radical containing 6 or more carbon atoms. An aryl group may be a fused or polycyclic ring system. Representative, but not exclusive examples of aryl groups include phenyl and napthyl.

The term "heteroaryl" as employed herein as such or as a part of another group, refers to an aromatic monocyclic or fused or polycyclic ring system having at least five ring atoms in which one or more of the atoms in the ring system is other than carbon, for example, nitrogen (including N-oxide), oxygen or sulfur. In a bicyclic aromatic radical only one ring, containing a heteroatom, need to be aromatic. Representative but not exclusive examples of heteroaryl include pyridyl, pyrrolyl, pyrazolyl, imidazolyl, thienyl, furanyl, indolyl, indolizinyl, azaindolizinyl, quinolyl, pyrazinyl, pyrimidinyl, pyridazinyl, oxazolyl, isoxazolyl, benzoxazolyl, benzisoxazolyl, benzothiazolyl, isoquinolinyl, benzimidazolyl, benztriazolyl, benzofuranyl, benzothienyl, benzopyranyl, imidazo[2,1-b]thiazolyl, imidazo [1,2-a]pyridyl, imidazo [1,2-a]-pyrimidinyl, pyrazolo [1,5-a]pyridyl, imidazolyl, triazolyl, thiadiazolyl, oxadiazolyl, triazolyl, triazolopyrimidinyl, pyrazolopyrimidinyl, thienopyridinyl, pyrrolopyridinyl 4,5,6,7-tetrahydrobenzisoxazolyl, indazolyl, 4,5,6,7-tetrahydroindazolyl, and 4,5,6,7-tetrahydrobenzothienyl.

The term "arylalkyl" as employed herein as such or as a part of another group, refers to a $(C_x-C_y)$alkyl group substituted with an optionally substituted aryl group, wherein the terms alkyl and aryl have been previously defined. Representative examples of aralkyl groups include benzyl, phenethyl, alpha-methylbenzyl, picolyl, and the like, and may be optionally substituted. "Optionally substituted" is intended to include both substituted and unsubstituted.

The term "heteroarylalkyl" as employed herein as such or as a part of another group, refers to an alkyl group substituted with an with an optionally substituted heteroarylaryl group, wherein the terms alkyl and heteroaryl has been previously described.

The term "substituted" as used herein in connection with various residues refers to halogen substituents, such as fluorine, chlorine, bromine, iodine, or $(C_1-C_7)$alkyl, halo$(C_1-C_7)$alkyl, hydroxy, amino, $(C1-C_7)$alkoxy, $(C_2-C_7)$acyl, $(C_1-C7)$alkylamino, amino$(C1-C_7)$alkyl, nitro, cyano, thiol carbamoylmethyl, $(C_1-C_7)$hydroxy, amino, trifluoromethyl, N-methylsulfonylamino, substituents. The "substituted" groups may contain 1 to 3, preferably 1 or 2, most 5 preferably 1 of the above mentioned substituents.

The term "leaving group" as used herein is a molecular fragment that departs with a pair of electrons in heterolytic bond cleavage. Representative, but not exclusive leaving groups can be anions or neutral molecules. Common anionic leaving groups are halides such as $Cl^-$, $Br^-$, and $I^-$, and sulfonate esters, such as para-toluenesulfonate or "tosylate" ($TsO^-$). Common neutral molecule leaving groups are water ($H_2O$), ammonia ($NH_3$), and alcohols (ROH).

The term "electron withdrawing group" as used herein refers to a chemical fragments able to draw electrons away from a reaction center. Representative but not exclusive examples of electron withdrawing groups are halogens, nitro, cyano, silanes, $-SiR^i_3$, $-NHCOCF_3$, $-NHCOR^i$, $-NH-CONHR^i$, $-NHCOOR^i$, $-OCONHR^i$, $-CONHR^i$, $-NHCSCF_3$, $-NHCSR^i$, $-NHSO_2R^i$, $-NCS$, $-OR^i$, $-COR^i$, $-COOR^i$, $-OSO_2R^i$, $-SO_2R^i$, $-S-R^i$, $-OH$, $-R^{ii}$, $-R^{iii}$.

$R^i$ is H, $(C_1-C_4)$-alkyl, $(C_1-C_4)$-halo alkyl, $(C_1-C_4)$-di-haloalkyl, $(C_1-C_4)$-tri-haloalkyl, $(C_1-C_4)$-perfluoro-alkyl, aryl, halogen, $(C_1-C_4)$alkenyl.

$R^{ii}$ is a fused ring with the phenyl residue selected in the group of:

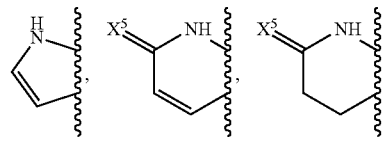

$X^5$ is S, $SO_2$, SO, O.

$R^{iii}$ is $(C_1-C_4)$-halo alkyl, $(C_1-C_4)$-tri-haloalkyl, $(C_1-C_4)$-perfluoro-alkyl.

The present invention will now be described by means of non limiting examples referring to the following figures:

FIG. 1: cytotoxic effect and apoptotic activity of (R)-bicalutamide on LNCaP and LNCaP-AR cell lines. The figure reports the dose-effect curves, with the relative $GI_{50}$ and $LC_{50}$ values, and the dot plots showing the apoptotic fraction induced by bicalutamide in LNCaP and LNCaP-AR cells.n.r=not reached.

FIGS. 2-11: cytotoxic activity of compounds (R)-XXIII-2, (R)-XXIII-3, (R)-XXIII-4, (R)-XXIII-5, (R)-XXIII-6, (R)-XXIII-7, (R)-XXIII-8, (R)-XXIII-9, (R)-XXIII-10, (R)-XXIV-9, at different concentration (0.02, 0.2, 2, 20 µM) after 144 h exposure on LNCaP and LNCaP-AR cell lines. On the x-axis is reported the concentration, while on the y-axis is reported the inhibition of the net growth (% net growth). n.r=not reached.

Figure 12:
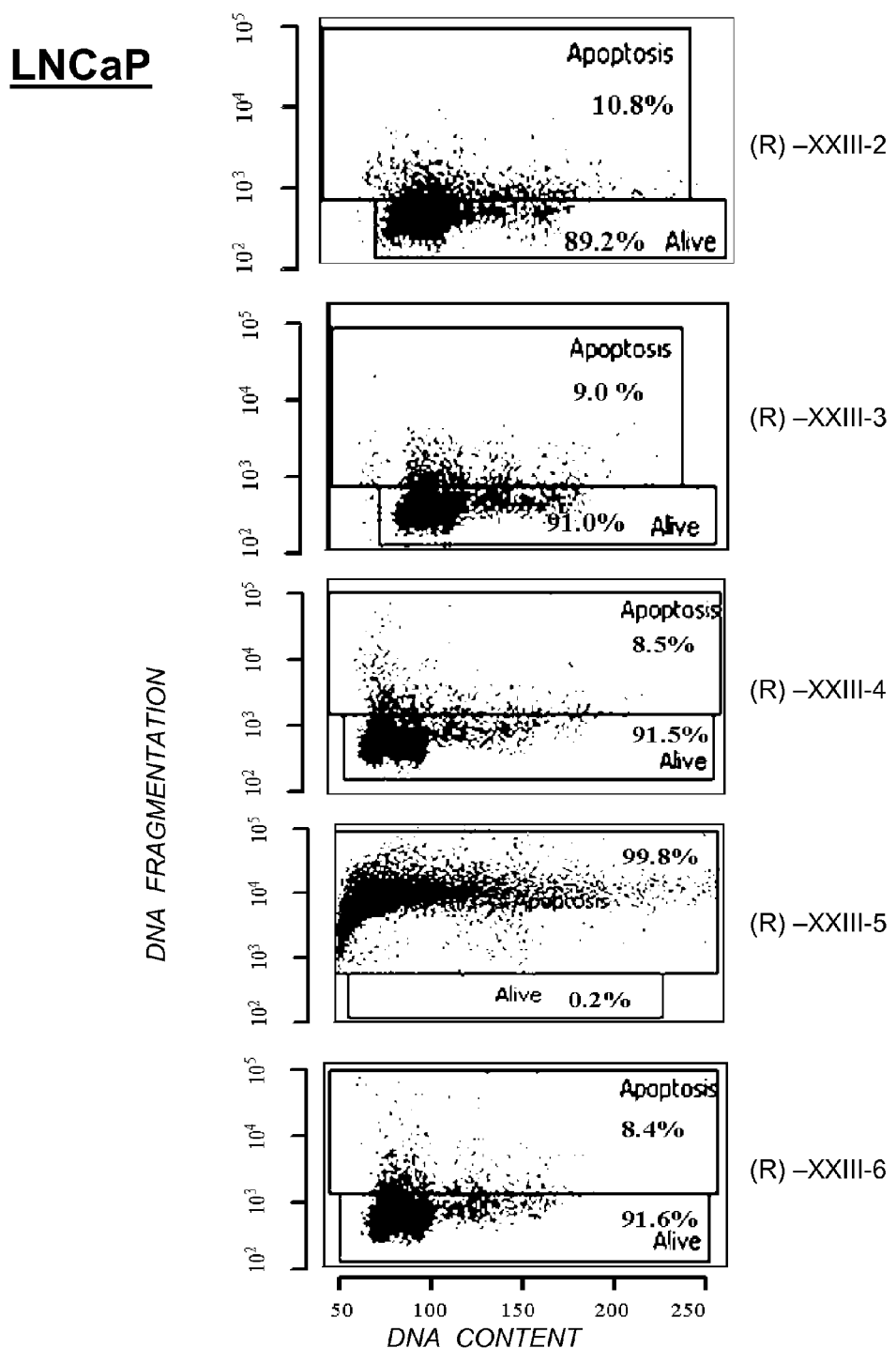

FIG. 12: apoptotic activity of the bicalutamide derivatives (R)-XXIII-2, (R)-XXIII-3, (R)-XXIII-4, (R)-XXIII-5, (R)-XXIII-6 on the LNCaP cell line.

Figure 13:
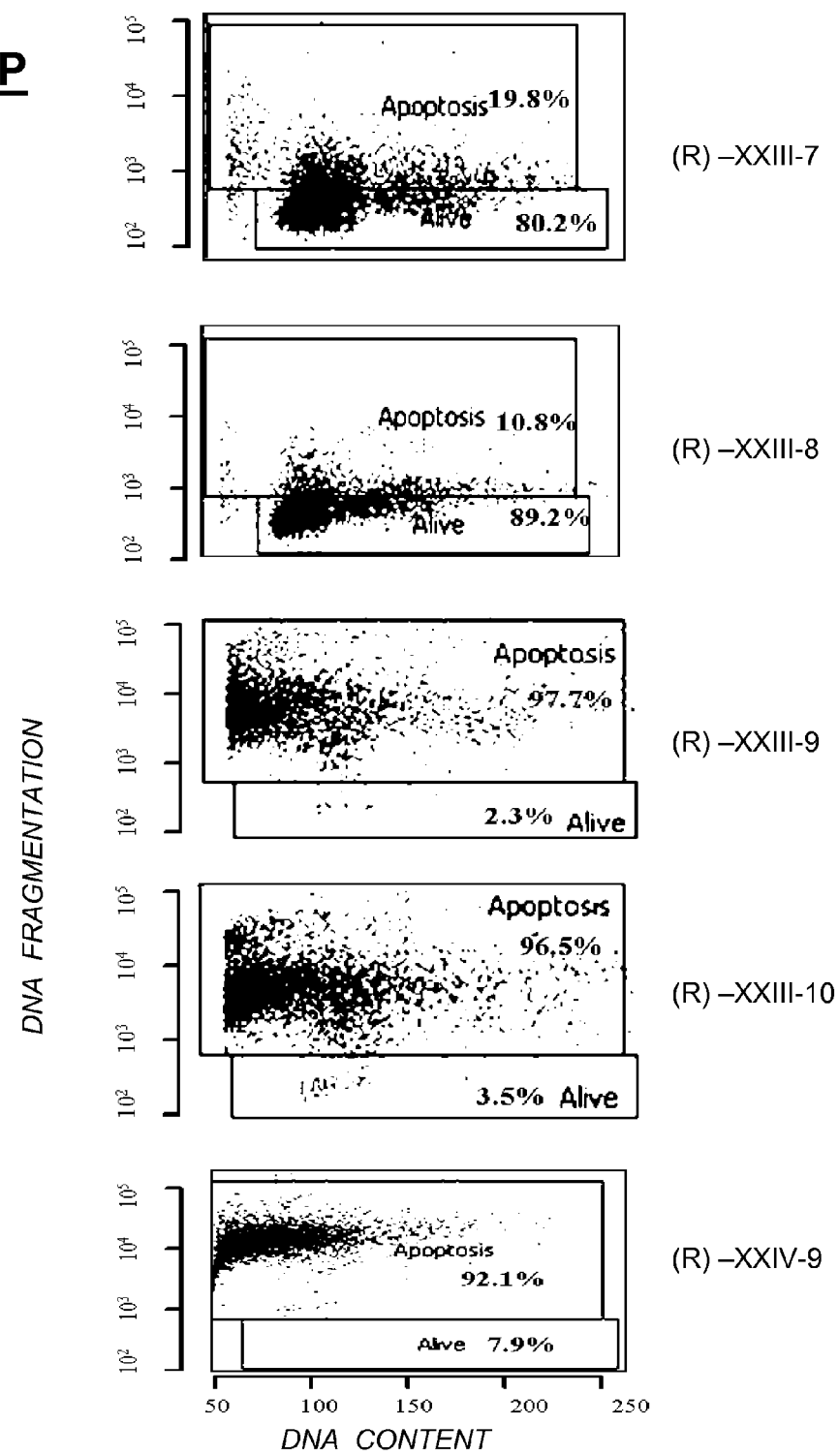

FIG. 13: apoptotic activity of the bicalutamide derivatives (R)-XXIII-7, (R)-XXIII-8, (R)-XXIII-9, (R)-XXIII-10, (R)-XXIV-9 on the LNCaP cell line.

Figure 14:
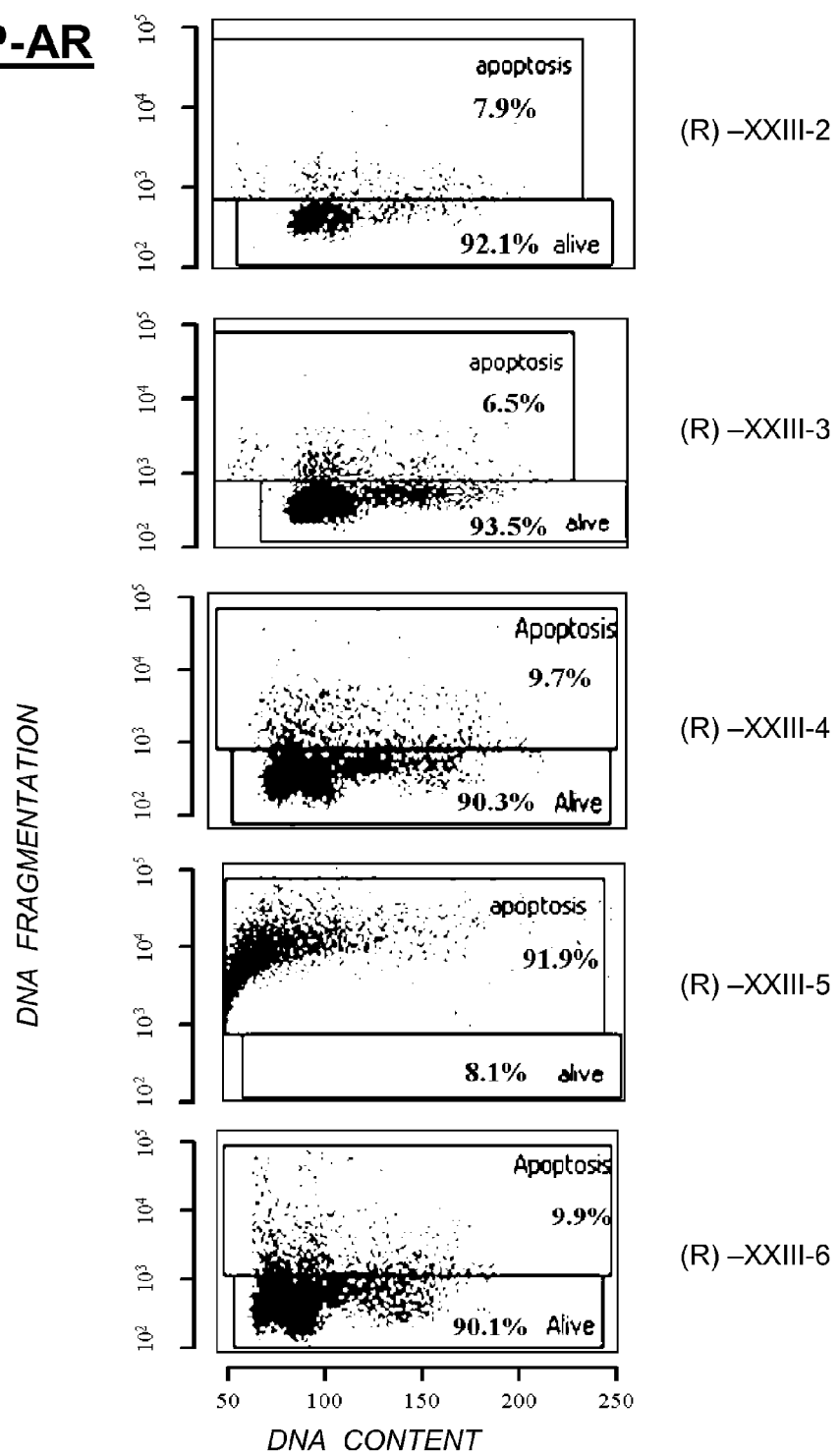

FIG. 14: apoptotic activity of the bicalutamide derivatives (R)-XXIII-2, (R)-XXIII-3, (R)-XXIII-4, (R)-XXIII-5, (R)-XXIII-6 on the LNCaP-AR cell line.

Figure 15:
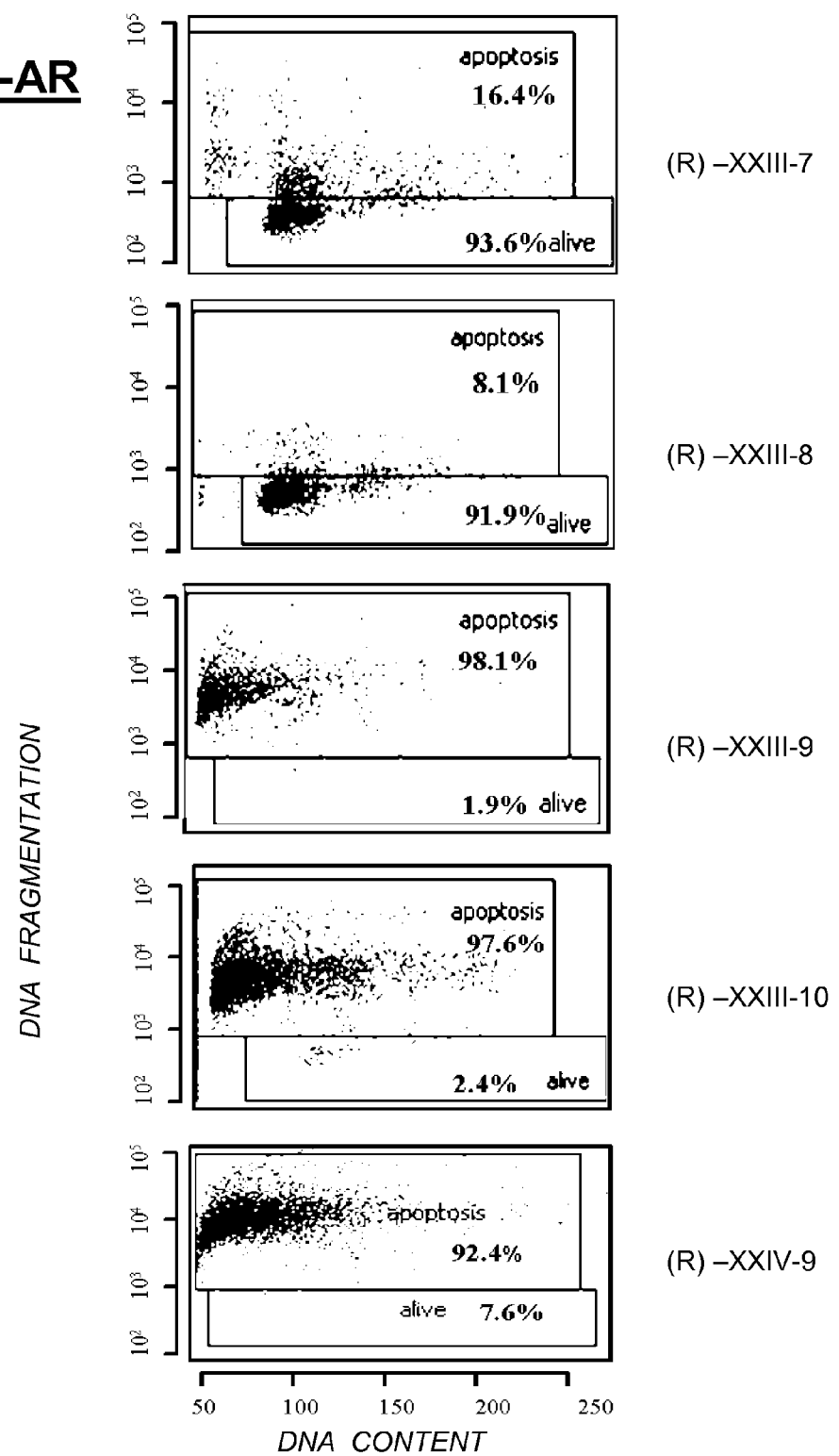
Figure 16:
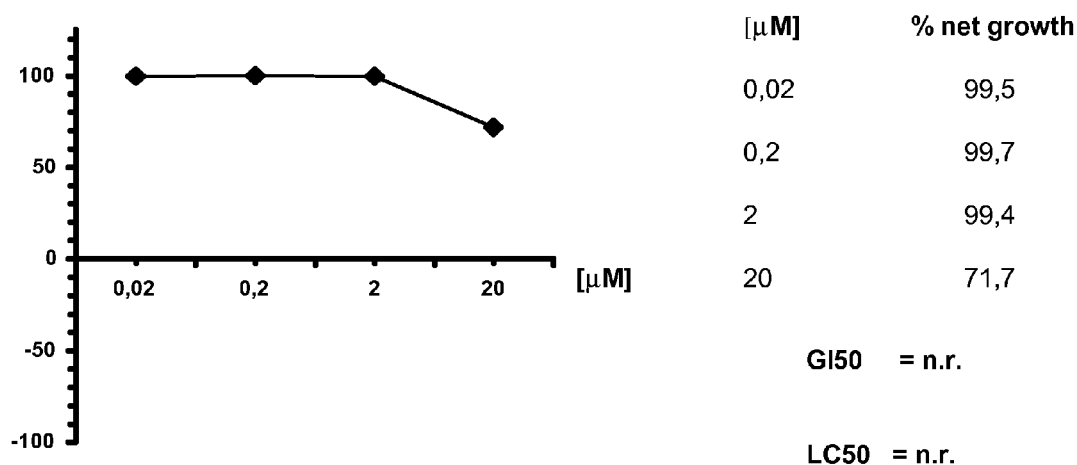
Figure 16:
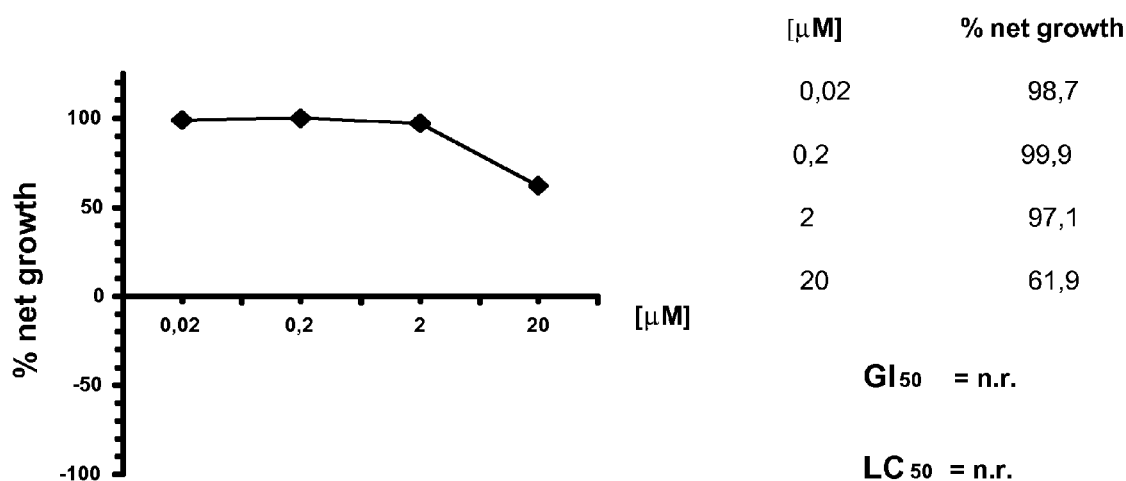
Figure 17:
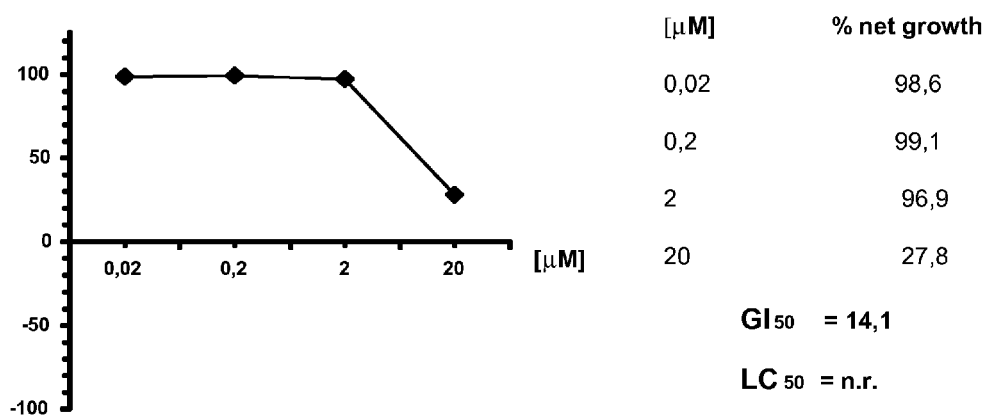
Figure 17:
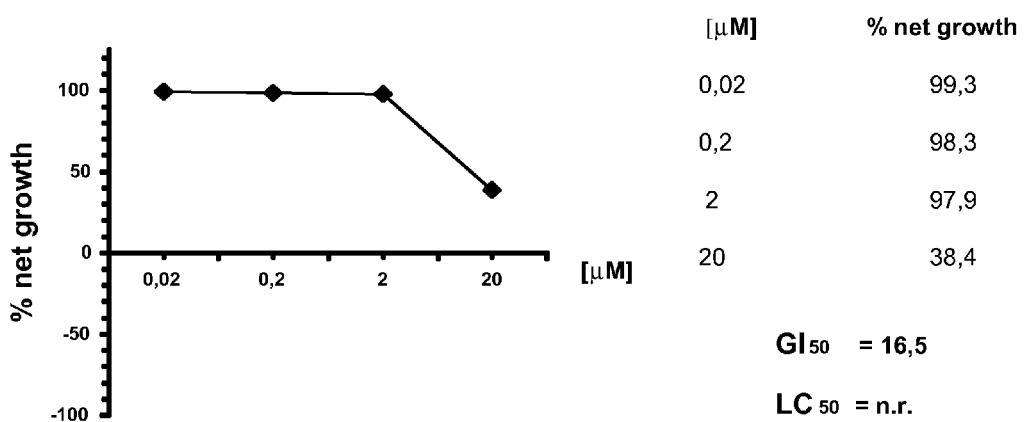
Figure 18:
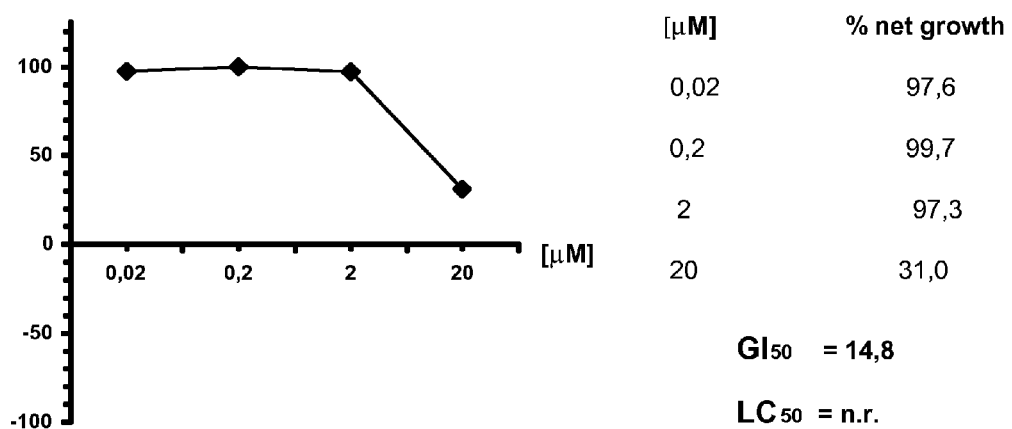
Figure 18:
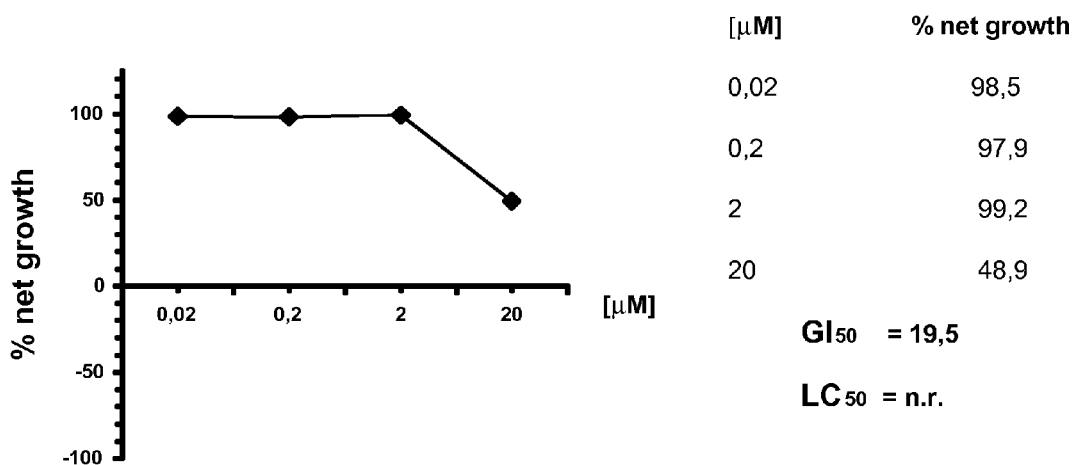
Figure 19:
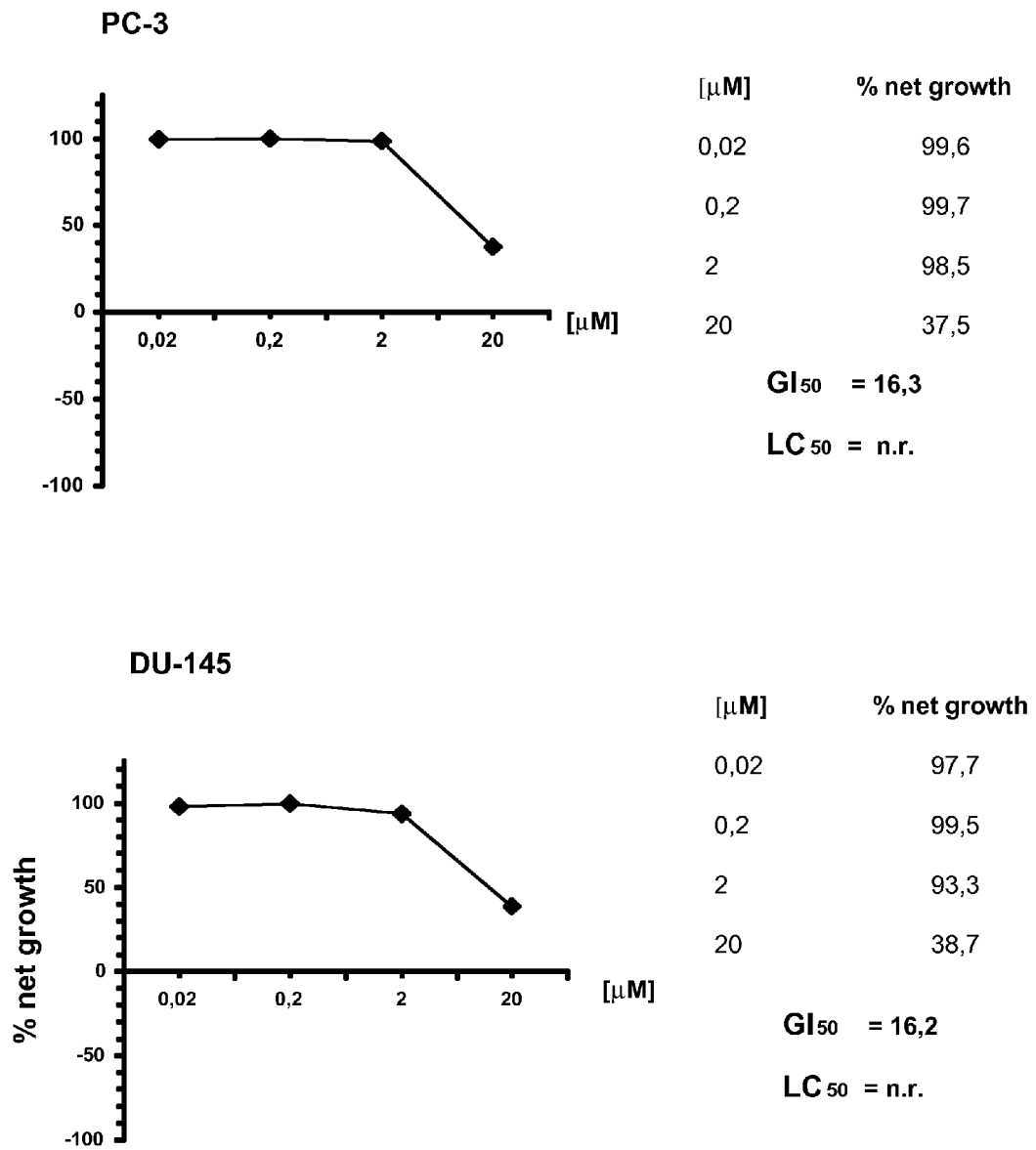
Figure 20:
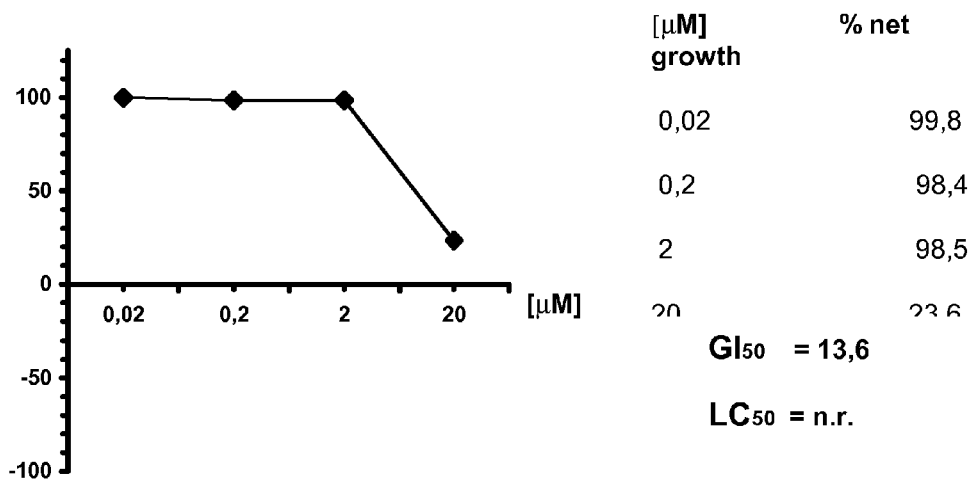
Figure 20:
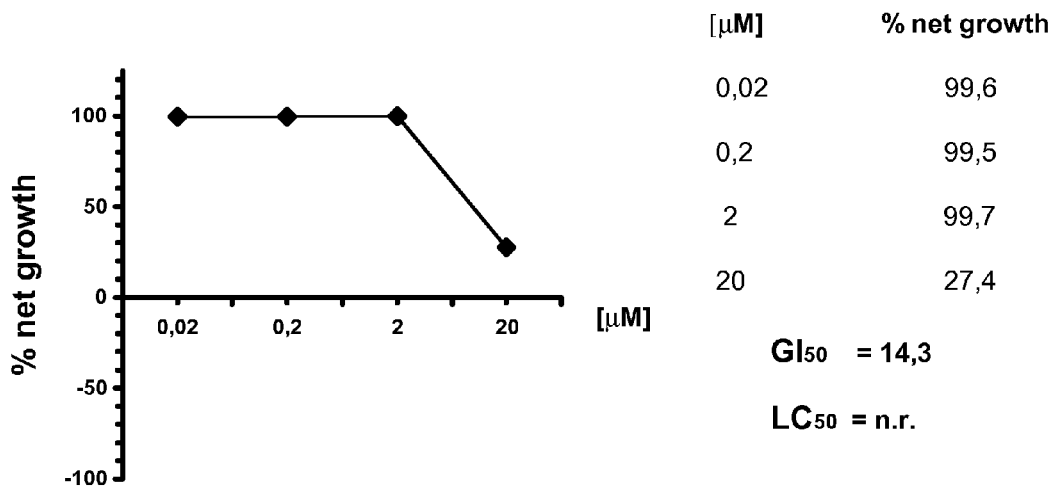
Figure 21:
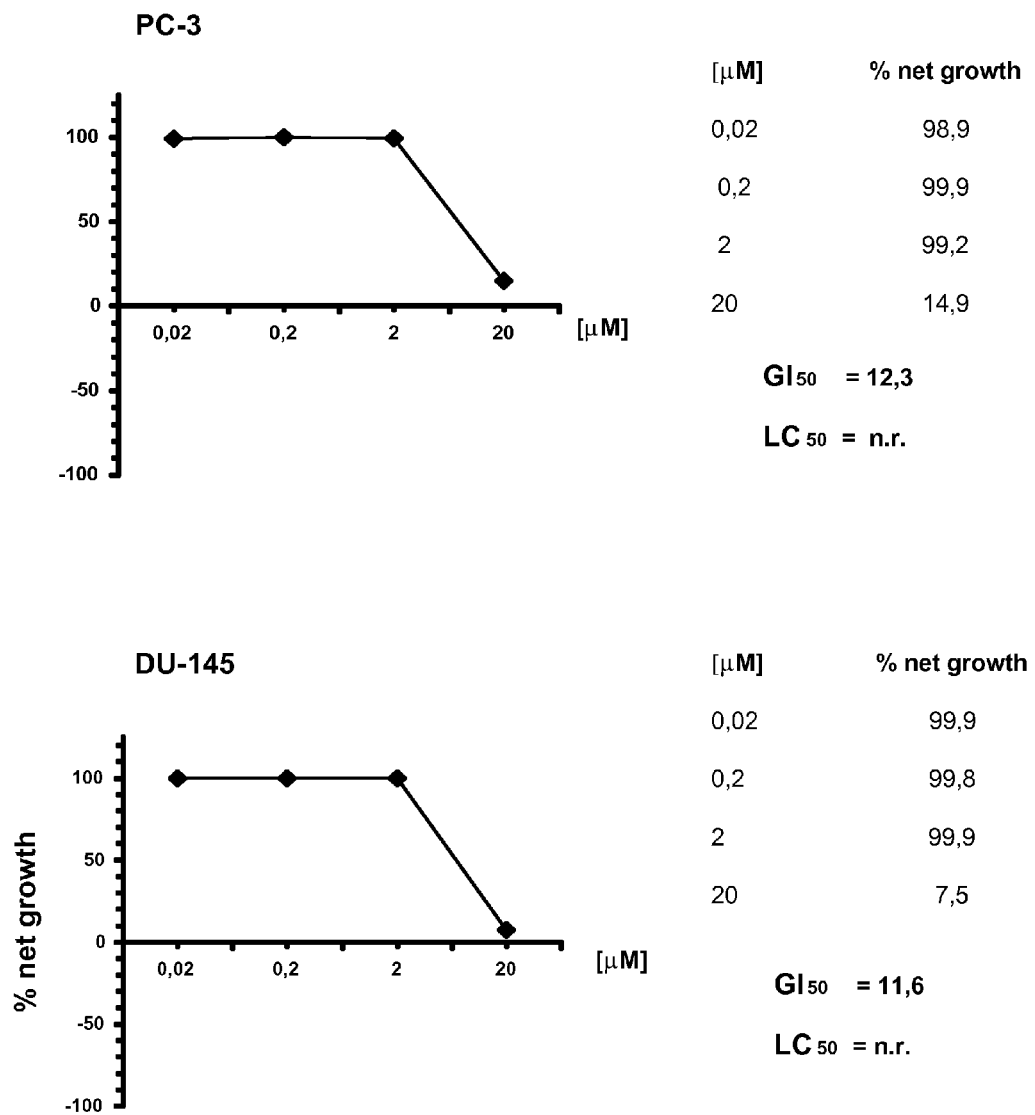
Figure 22:
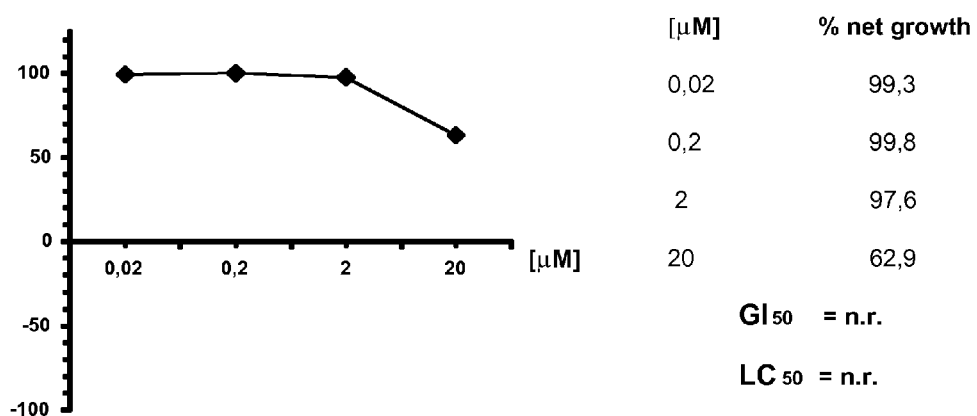
Figure 22:
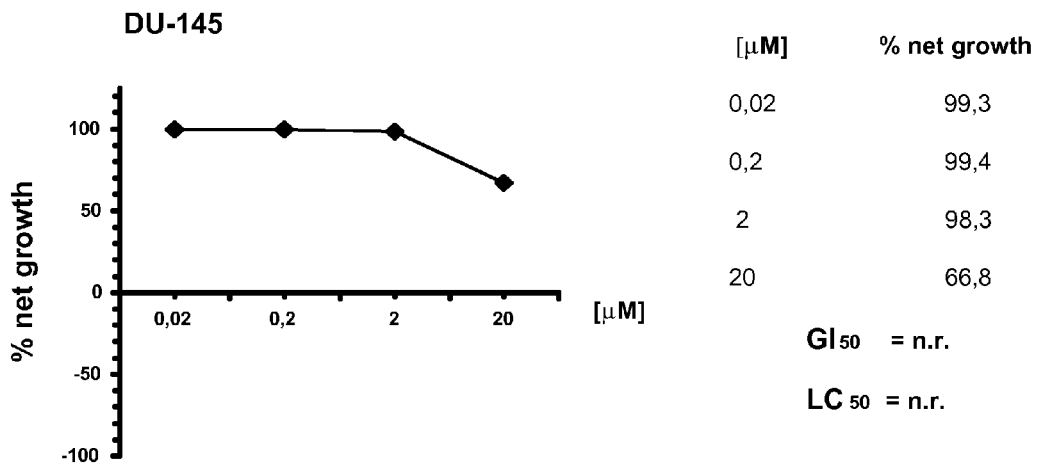
Figure 23:
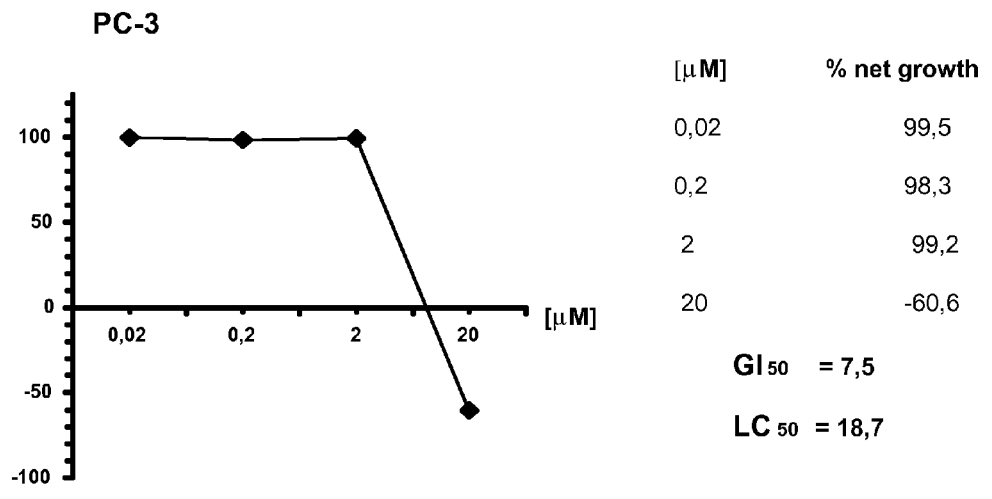
Figure 23:
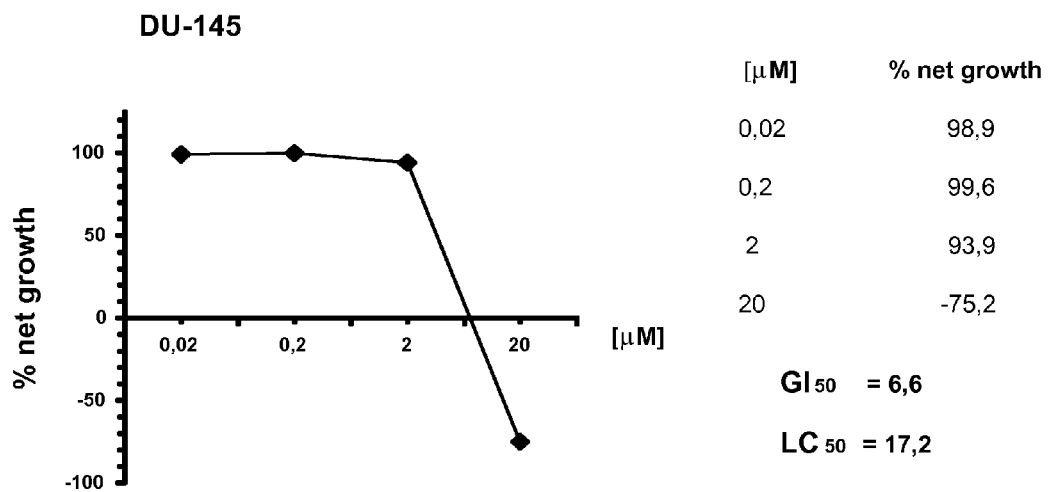
Figure 24:
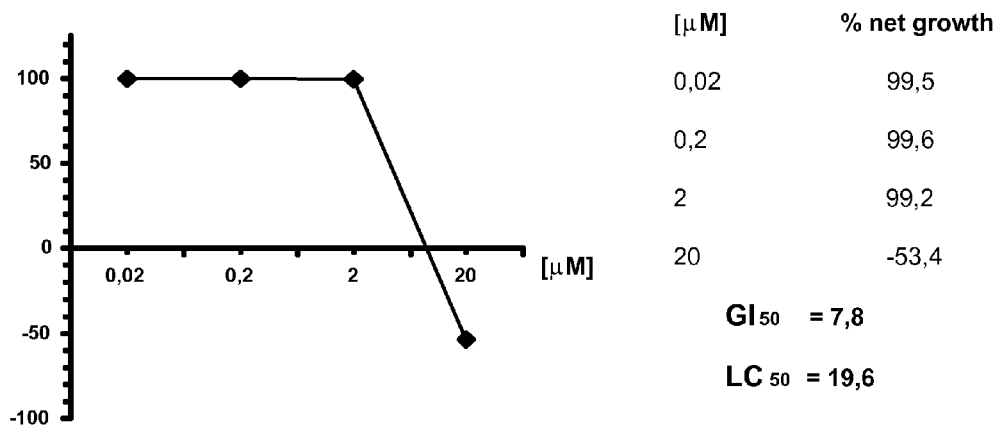
Figure 24:
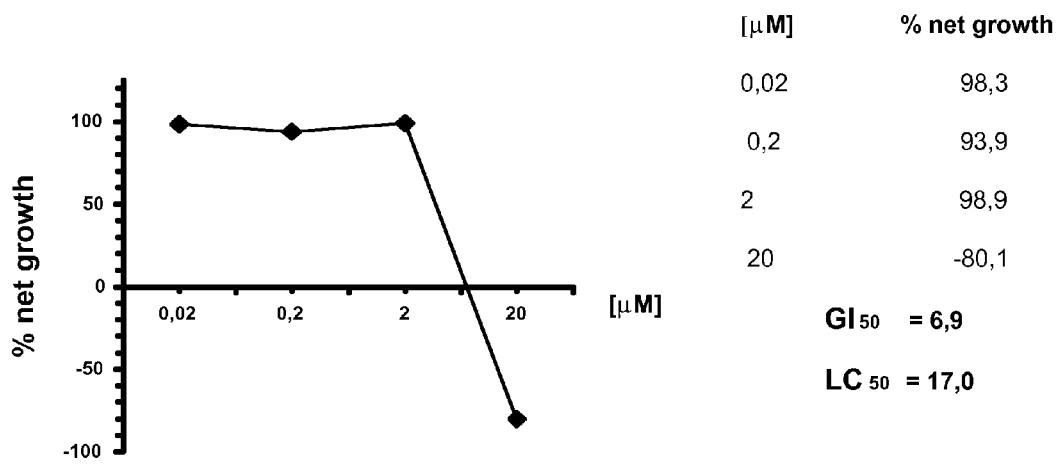
Figure 25:
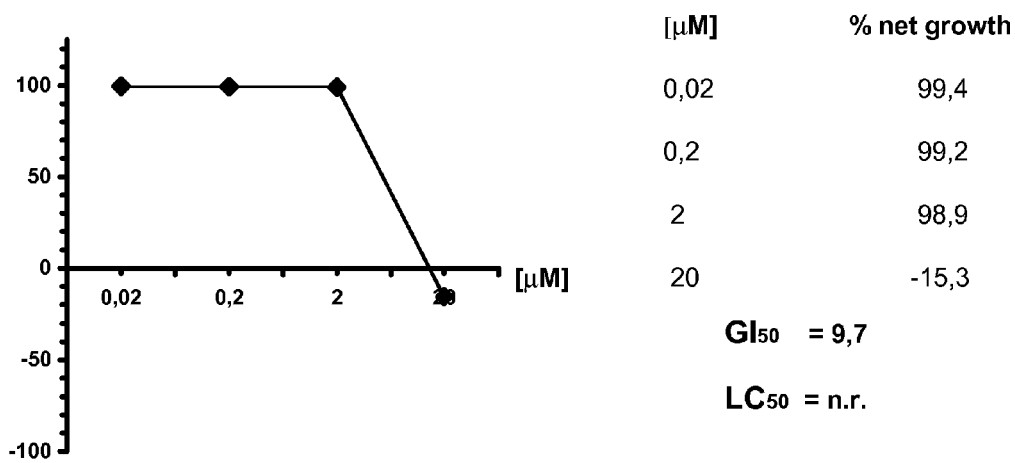
Figure 25:
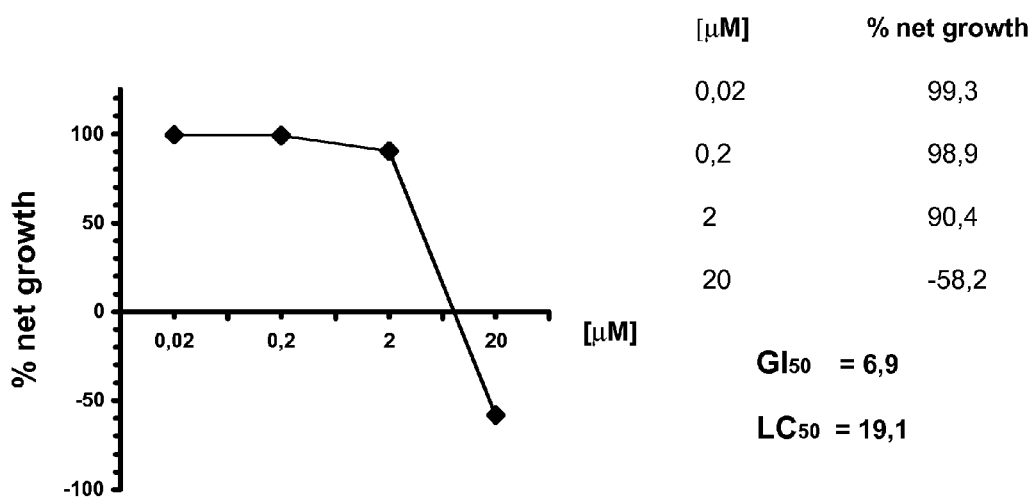

FIG. 15: apoptotic activity of the bicalutamide derivatives (R)-XXIII-7, (R)-XXIII-8, (R)-XXIII-9, (R)-XXIII-10, (R)-XXIV-9 on the LNCaP-AR cell line.

FIGS. 16-25: cytotoxic effect of compounds (R)-XXIII-2, (R)-XXIII-3, (R)-XXIII-4, (R)-XXIII-5, (R)-XXIII-6, (R)-XXIII-7, (R)-XXIII-8, (R)-XXIII-9, (R)-XXIII-10, (R)-XXIV-9 on PC-3 and DU-145 cell lines at different concentration (0.02, 0.2, 2, 20 µM) after 144 h exposure. On the x-axis is reported the concentration, while on the y-axis is reported the inhibition of the net growth (% net growth).

Figure 26:
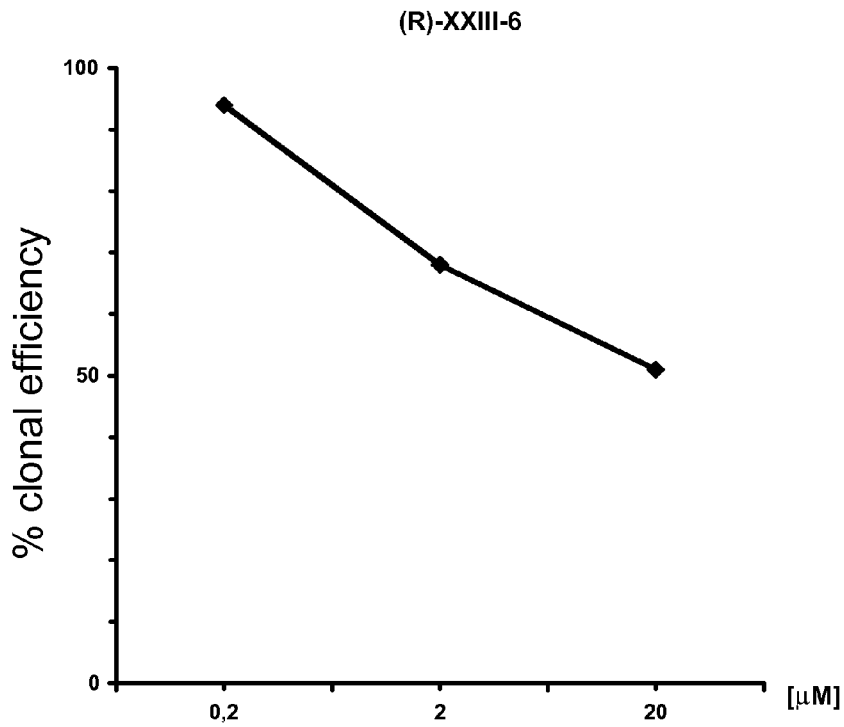
Figure 27:
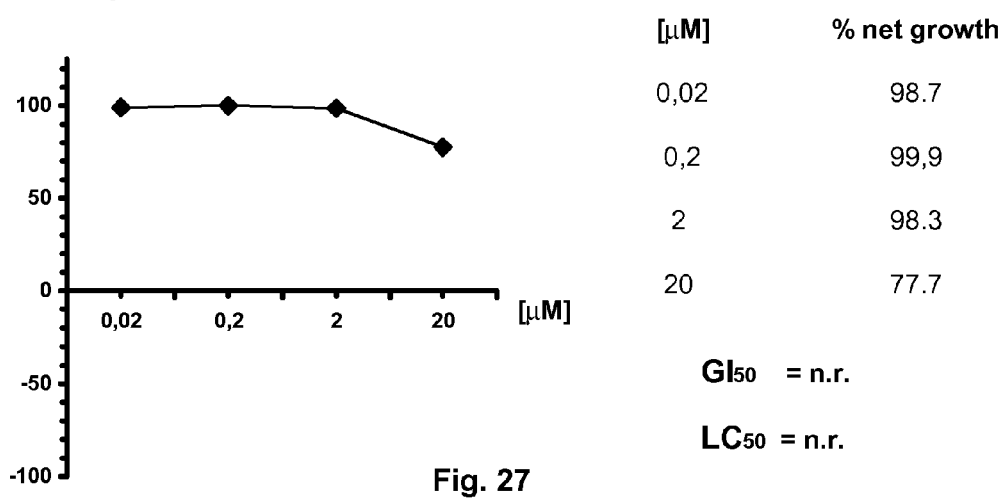
Figure 28:
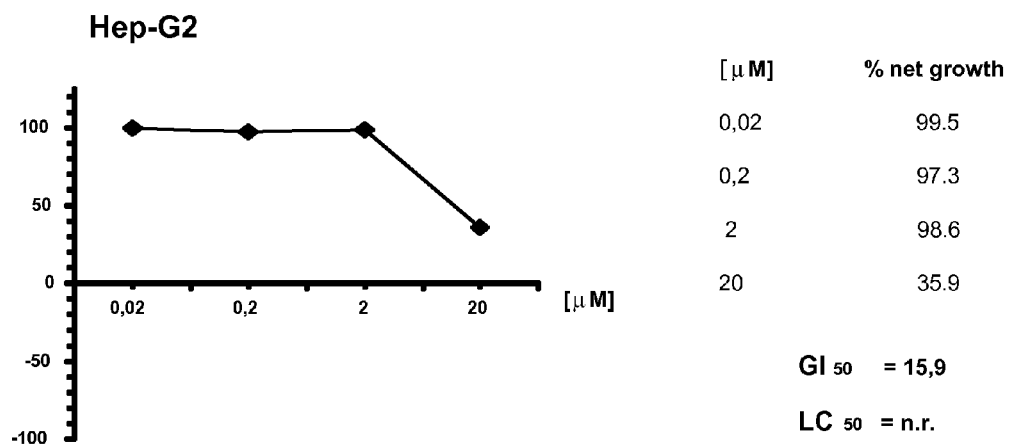
Figure 29:
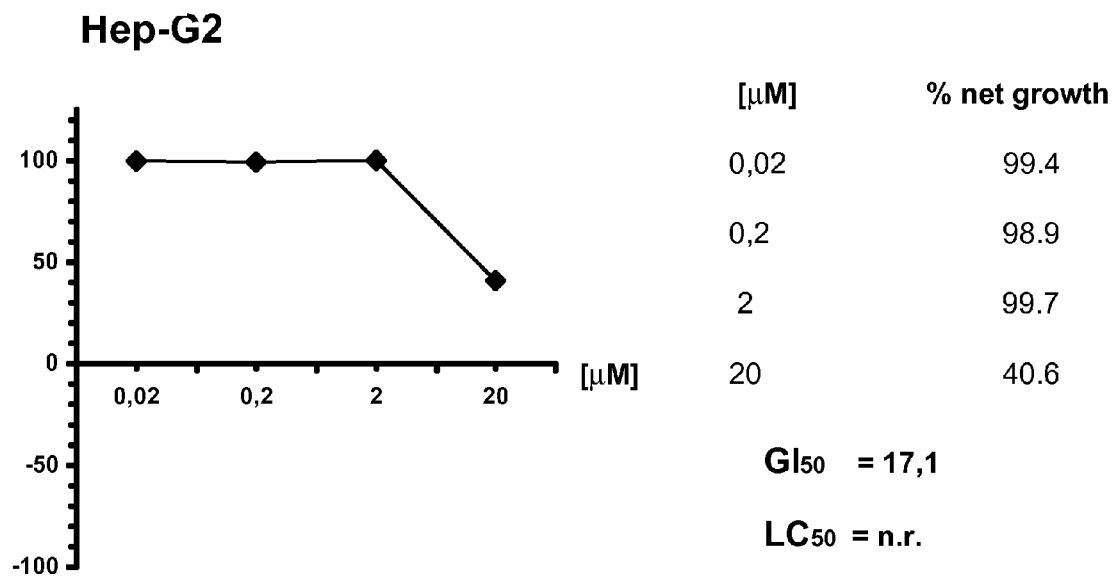
Figure 30:
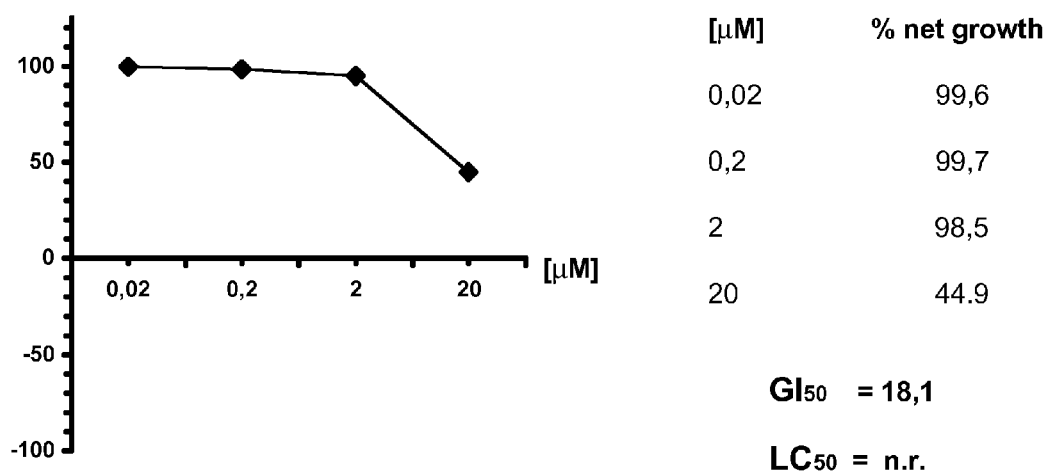
Figure 31:
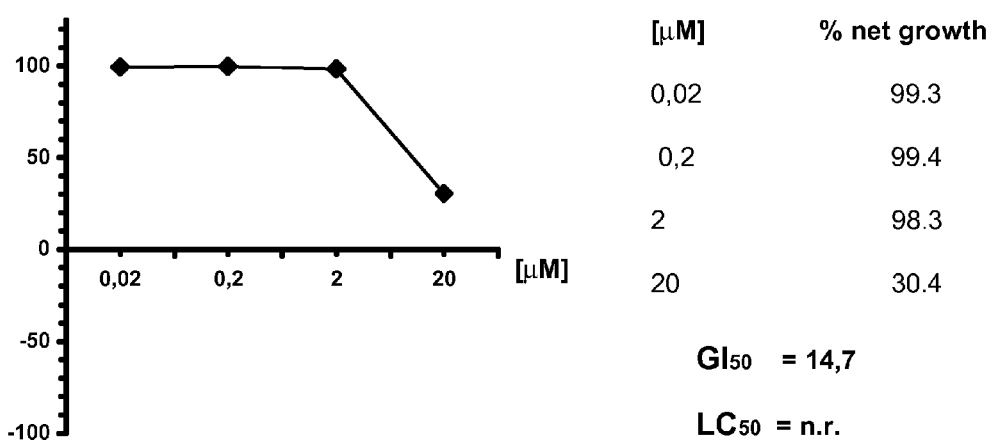
Figure 32:
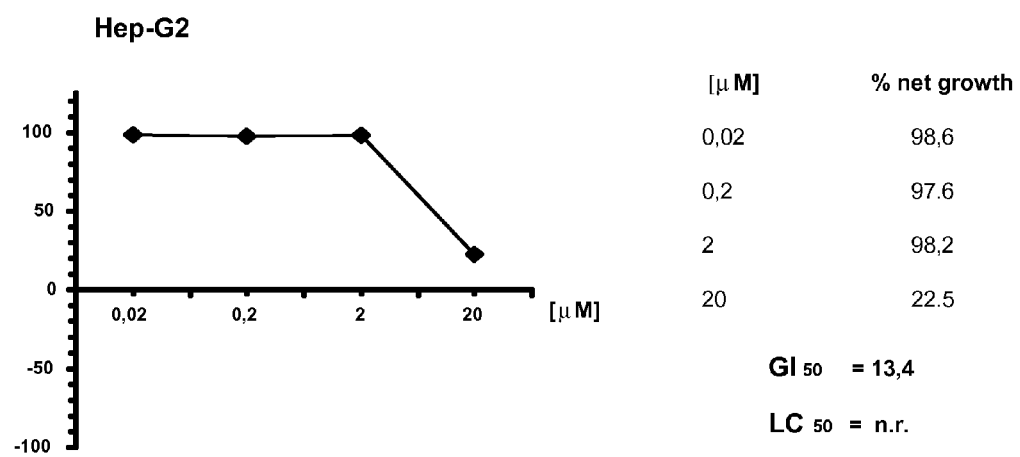
Figure 33:
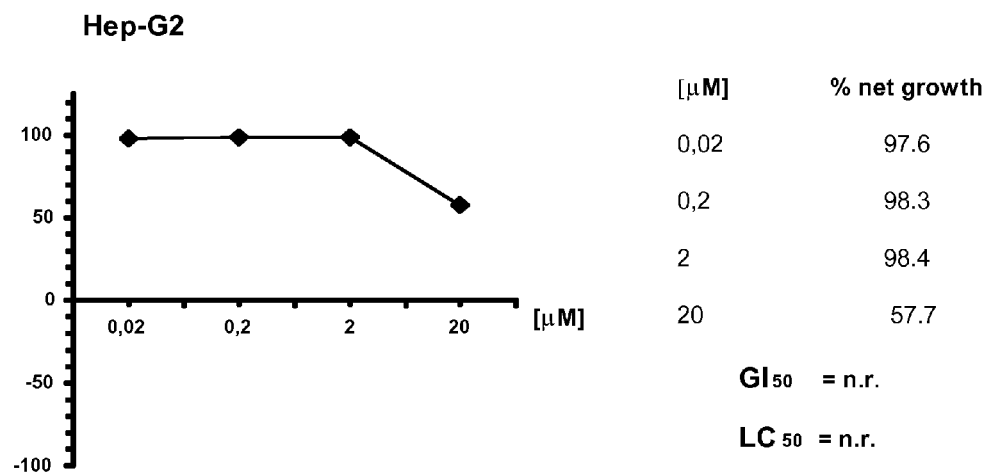
Figure 34:
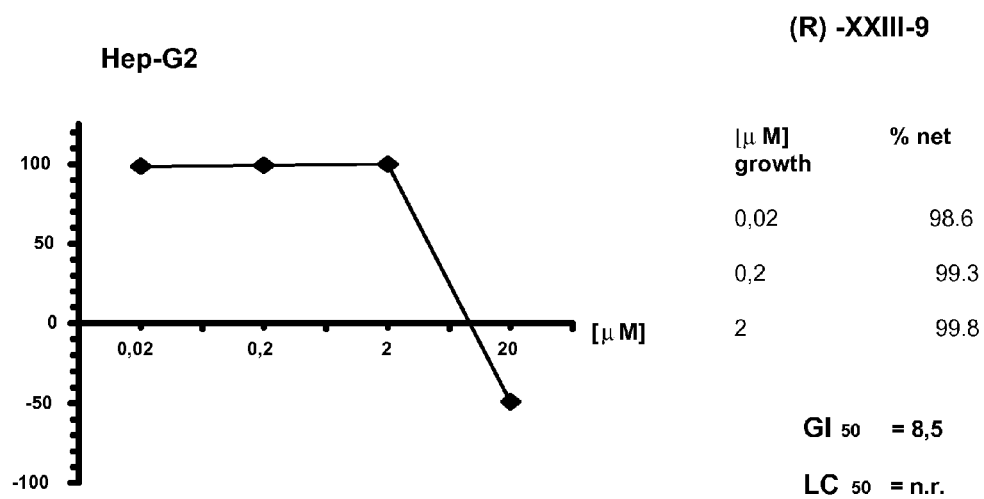
Figure 35:
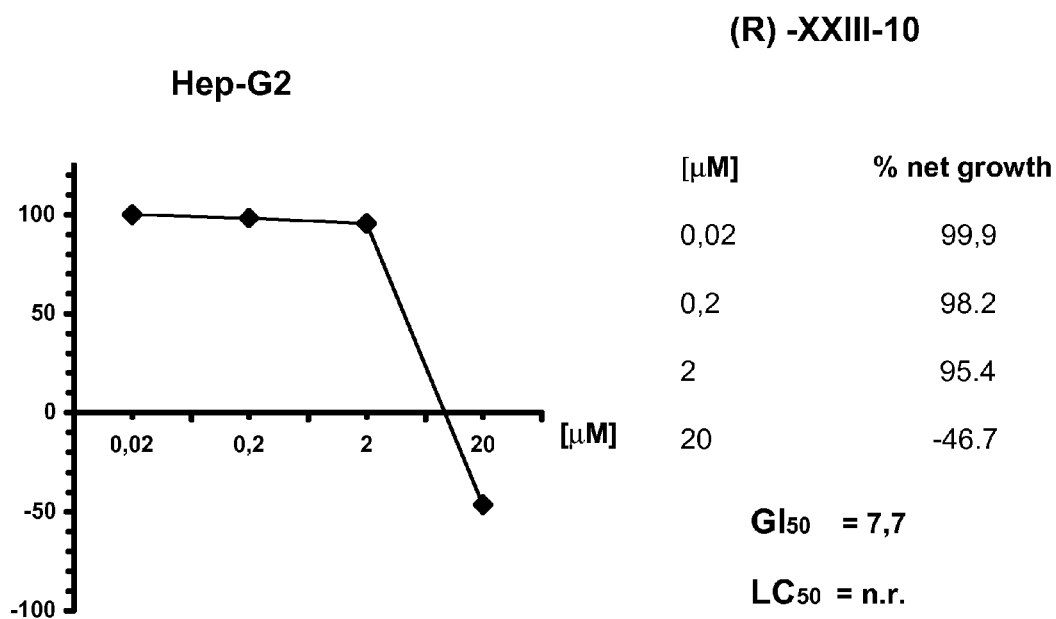

FIG. 26: Ability of compound (R)-XXIII-6 to inhibit clonogenic growth of normal stem cells derived from human peripheral blood stem cells.

FIGS. 27-35: cytotoxic activity of compounds (R)-XXIII-2, (R)-XXIII-3, (R)-XXIII-4, (R)-XXIII-5, (R)-XXIII-6, (R)-XXIII-7, (R)-XXIII-8, (R)-XXIII-9, (R)-XXIII-10, on the human hepatoblastoma cell line HepG2.

Figure 36:
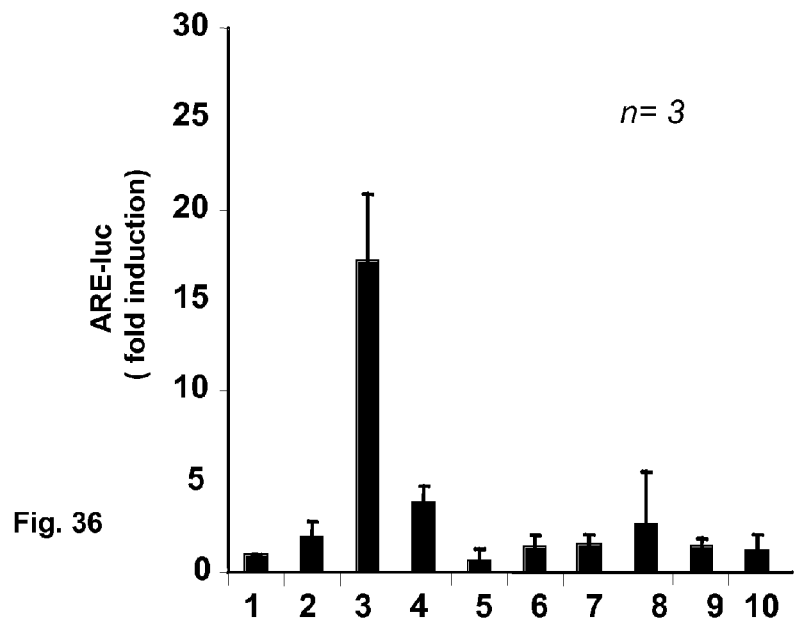
Figure 37:
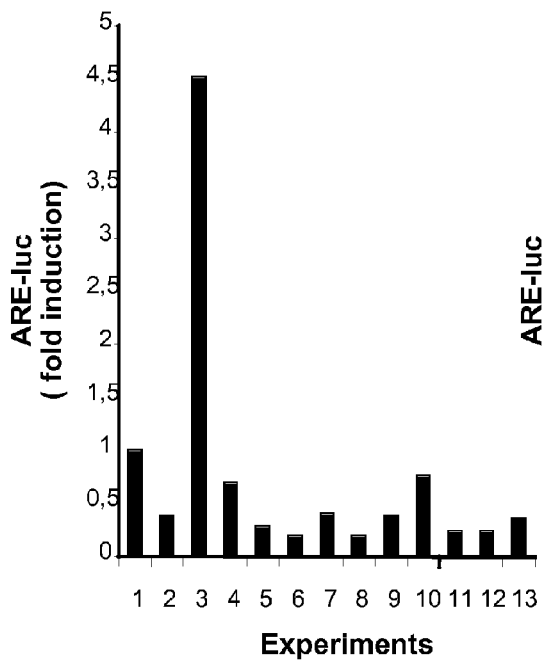
Figure 38:
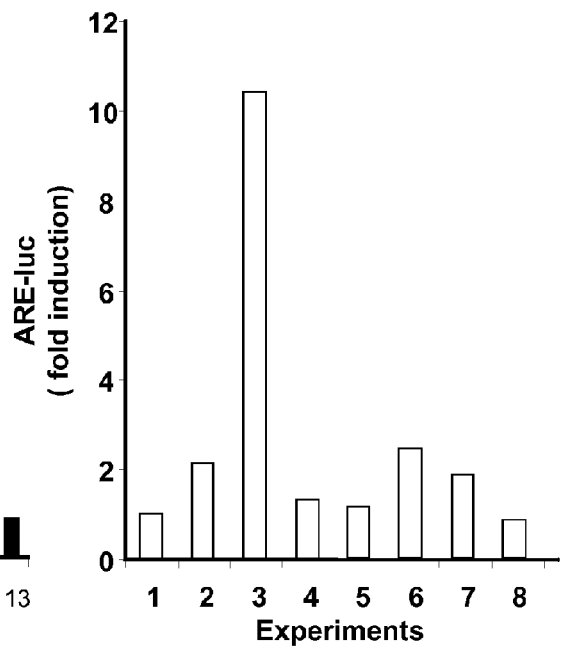

FIGS. 36-38: dosage of the human androgen receptor transcriptional activity in the presence of compounds: (R)-XXIII-3, (R)-XXIII-4, (R)-XXIII-5, (R)-XXIII-6, (R)-XXIII-8.

Conditions reported in the tables:

(1) Plasmid transfected cells+ARE-luc+β-galactosidase, without human AR;

(2) Plasmid transfected cells+ARE-luc+β-galactosidase+hAR;

(3) Plasmid transfected cells+ARE-luc+β-galactosidase+hAR+R1881 (10 nM) [androgen].

For FIG. 36:

| Experiment | Conditions | Compound (concentration) |
|---|---|---|
| 1 | Control(1) | none |
| 2 | (2) | none |
| 3 | (3) | none |
| 4 | (3) | Casodex (10 μM) |
| 5 | (3) | (R)-XXIII-4 (10 μM) |
| 6 | (3) | (R)-XXIII-6 (10 μM) |
| 7 | (2) | (R)-XXIII-6 (10 nM) |
| 8 | (2) | (R)-XXIII-6 (100 nM) |
| 9 | (2) | (R)-XXIII-6 (1 μM) |
| 10 | (2) | (R)-XXIII-6 (10 μM) |

For FIG. 37

| Experiment | Conditions | Compound (concentration) |
|---|---|---|
| 1 | Control (1) | none |
| 2 | (2) | none |
| 3 | (3) | none |
| 4 | (3) | Casodex (10 μM) |
| 5 | (3) | (R)-XXIII-3 (10 μM) |
| 6 | (3) | (R)-XXIII-5 (10 μM) |
| 7 | (2) | (R)-XXIII-3 (10 nM) |
| 8 | (2) | (R)-XXIII-3 (100 nM) |
| 9 | (2) | (R)-XXIII-3 (1 μM) |
| 10 | (2) | (R)-XXIII-3 (10 μM) |
| 11 | (2) | (R)-XXIII-5 (10 nM) |
| 12 | (2) | (R)-XXIII-5 (100 nM) |
| 13 | (2) | (R)-XXIII-5 (1 μM) |

For FIG. 38:

| Experiment | Conditions | Compound (concentration) |
|---|---|---|
| 1 | Control (1) | none |
| 2 | (2) | none |
| 3 | (3) | none |
| 4 | (3) | Casodex (10 μM) |
| 5 | (3) | R-XXIII-8 (10 μM) |
| 6 | (2) | R-XXIII-8 (10 nM) |
| 7 | (2) | R-XXIII-8 (100 nM) |
| 8 | (2) | R-XXIII-8 (1 μM) |

For each experiment, the ectopically expressed hAR was detected by Western blot, as described in the previous section. Similar amounts of hAR were expressed in each experiment.

Data in FIG. 36-38 have been obtained from two independent experiments. Mean is shown (SEM<1).

Figure 39:
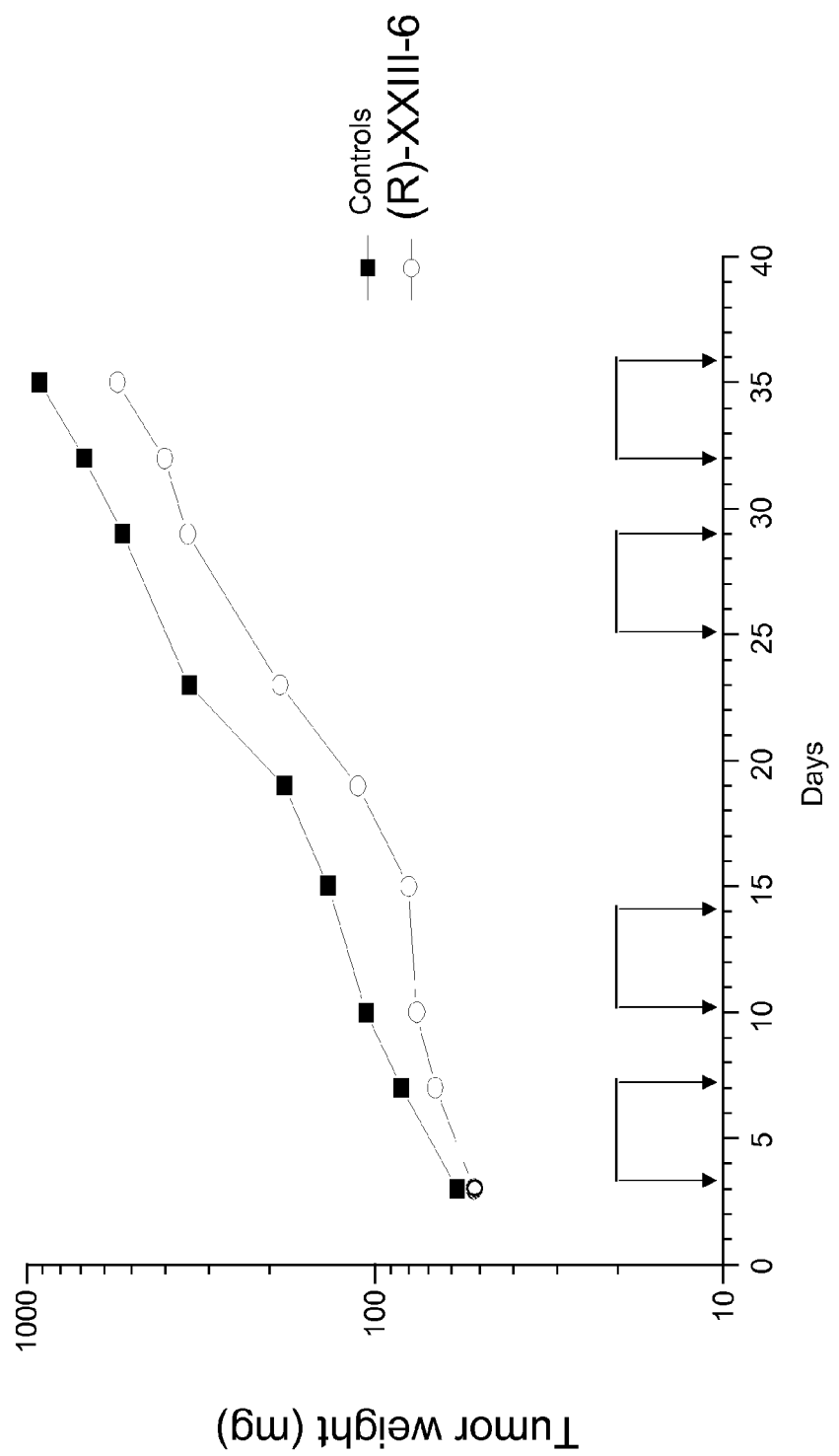

FIG. 39: In vivo antitumor activity of (R)-XXIII-6 against the human CW22-RV1 prostatic carcinoma xenograft. Drug treatment: p.o., 100 mg/kg, qdx5/wx4w. Drugs were dissolved in 10% DMSO in distilled water.

EXAMPLE 1

Synthesis of (2S,5R)-1,3-dioxolan-4-ones VIII-1 to VIII-8

Step (iii) of Scheme 2: (Representative Example)

To a suspension of (2S,5R)-XXVIII-1 [obtained according to Huang, Y.; et al. *Tetrahedron Asym.* 2006, 3152] (0.75 mmol, 1 eq) and 2-mercapto pyridine-N-oxide (1.05 mmol, 1.4 eq) in $CBrCl_3$, a solution of dicyclohexylarbodimide (DCC) in $CBrCl_3$ (1.8 mmol, 2.4 eq) under reflux. The addition was performed during 30 min and than the reaction mixture was further stirred at reflux for 2 h. After cooling, the solvent was removed under reduce pressure and the crude material was purified by silica gel column chromatography (eluent: cHex/$Et_2O$: 7/3). Y=88%.

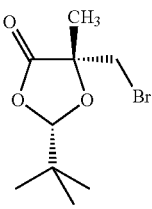

(2S,5R)-VIII-1: $^1$H NMR (400 MHz, $CDCl_3$): 5.18 (s, 1H), 3.57 (d, J=11.6 Hz, 1H), 3.55 (d, J=11.6 Hz, 1H) 1.51 (s, 3H), 1.03 (s, 9H). $^{13}$C NMR (100 MHz, $CDCl_3$): 172.7, 108.0, 79.3, 34.9, 24.0, 19.1.

The same procedure was applied for the synthesis of VIII-1÷VIII-7 starting from the corresponding carboxylic acids.

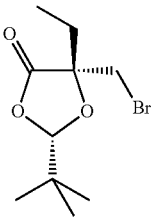

(2S,5R)-VIII-2: $^1$H NMR (400 MHz, $CDCl_3$): 5.22 (s, 1H), 3.61 (d, J=14 Hz, 1H), 3.59 (d, J=14 Hz, 1H), 1.94 (m, 2H), 1.02 (m, 3H), 1.01 (s, 9H).

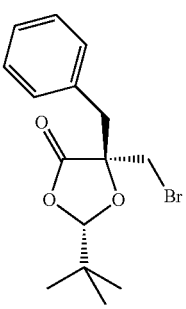 [SMILES: CC(C)(C)[C@@H]1OC(=O)[C@@](CBr)(Cc2ccccc2)O1]

(2S,5R)-VIII-3: $^1$H NMR (400 MHz, $CDCl_3$): 7.20-7.39 (m, 5H), 4.44 (s, 1H), 3.61 (d, J=11.2 Hz, 1H), 3.54 (d, J=11.2 Hz, 1H), 3.19 (d, J=14 Hz, 1H), 3.13 (d, J=14 Hz, 1H), 0.91 (s, 9H). $^{13}$C NMR (100 MHz, $CDCl_3$): 172.3, 133.7, 130.5, 129.0, 128.0, 109.3, 82.6, 40.3, 34.8, 34.7, 29.8.

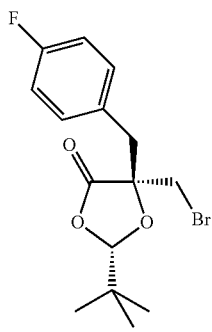

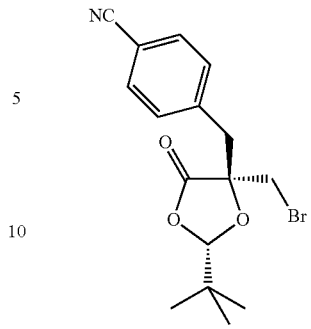

(2S,5R)-VIII-4: $^1$H NMR (400 MHz, CDCl$_3$): 7.26-7.21 (m, 2H, ArH), 7.01 (t, J=8.4 Hz, 2H, ArH), 4.47 (s, 1H, CH), 3.55 (q, J=11.2 Hz, 2H, CH$_2$), 3.15 (s, 2H, CH$_2$), 0.91 (s, 9H, $^t$Bu). $^{13}$C NMR (100 MHz, CDCl$_3$): 171.1, 163.9, 161.4, 132.1 (d), 129.4 (d), 115.9 (d), 190.4, 82.5, 39.5, 34.9, 34.6, 23.8.

(2S,5R)-VIII-7: $^1$H NMR (400 MHz, CDCl$_3$): 7.62 (d, J=8.4 Hz, 2H, ArH), 7.38 (d, J=8.4 Hz, 2H, ArH), 4.50 (s, 1H, CH), 3.54 (q, J=11.6 Hz, 2H, CH$_2$), 3.24 (q, J=14.0 Hz, 2H, CH$_2$), 0.92 (s, 9H, $^t$Bu). $^{13}$C NMR (100 MHz, CDCl$_3$): 171.5, 139.3, 132.7, 131.4, 118.6, 112.1, 109.5, 82.0, 40.2, 34.9, 34.4, 23.7.

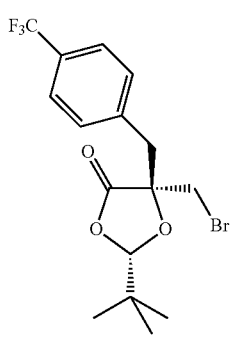 [SMILES: CC(C)(C)[C@@H]1OC(=O)[C@@](CBr)(Cc2ccc(C(F)(F)F)cc2)O1]

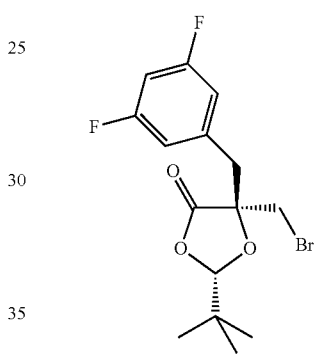

(2S,5R)-VIII-5: $^1$H NMR (400 MHz, CDCl$_3$): 7.58 (d, J=8.4 Hz, 2H, ArH), 7.38 (d, J=8.0 Hz, 2H, ArH), 4.54 (s, 1H, CH), 3.56 (q, J=11.2 Hz, 2H, CH$_2$), 3.23 (s, 2H, CH$_2$), 0.92 (s, 9H, $^t$Bu). $^{13}$C NMR (100 MHz, CDCl$_3$): 171.7, 137.8, 130.9, 130.2 (q), [128.3, 125.6, 122.8, 120.1] (q), 109.4, 82.1, 39.8, 34.9, 34.4, 23.7.

(2S,5R)-VIII-9: $^1$H NMR (400 MHz, CDCl$_3$): 6.82-6.79 (m, 3H, ArH), 4.63 (s, 1H, CH), 3.55 (q, J=11.6 Hz, 2H, CH$_2$), 3.15 (s, 2H, CH$_2$), 0.95 (s, 9H, $^t$Bu). $^{13}$C NMR (100 MHz, CDCl$_3$): 171.6, (164.5, 164.4, 162.0, 161.9; dd; J$^1$=248.3 Hz; J$^2$=12.7 Hz), 137.4, (113.7, 113.6, 113.5, 113.4; dd; J$^1$=18.3 Hz; J$^2$=6.8 Hz), 109.5, 103.7 (t, J=25.1 Hz), 82.0, 39.7, 34.9, 34.4, 23.7.

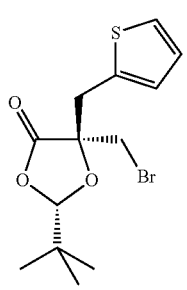 [SMILES: CC(C)(C)[C@@H]1OC(=O)[C@@](CBr)(Cc2cccs2)O1]

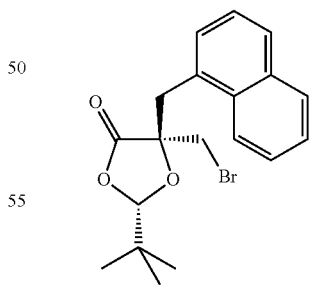

(2S,5R)-VIII-6: $^1$H NMR (400 MHz, CDCl$_3$): 7.26-7.24 (m, 1H, ArH), 6.98-6.94 (m, 2H, ArH), 4.71 (s, 1H, CH), 3.59 (dd, J$^1$=16.8 Hz, J$^2$=11.6 Hz, 2H, CH$_2$), 3.39 (dd, J$^1$=19.6 Hz, J$^2$=14.0 Hz, 2H, CH$_2$), 0.96 (s, 9H, $^t$Bu). $^{13}$C NMR (100 MHz, CDCl$_3$): 171.9, 134.6, 128.4, 127.5, 126.3, 109.5, 82.1, 34.9, 34.1 (d), 23.8.

(2S,5R)-VIII-10: $^1$H NMR (400 MHz, CDCl$_3$): 7.82-7.79 (m, 3H, ArH), 7.72 (s, 1H, ArH), 7.51-7.48 (m, 1H, ArH), 7.40-7.38 (m, 2H, ArH), 4.55 (s, 1H, CH), 3.65 (d, J=11.2 Hz, 1H, CH$_2$), 3.57 (d, J=11.6 Hz, 1H, CH$_2$), 3.34 (s, 2H, CH$_2$), 0.91 (s, 9H, $^t$Bu). $^{13}$C NMR (100 MHz, CDCl$_3$): 170.2, 131.1, 129.6, 128.6, 128.3, 128.0, 127.9, 126.6, 126.4, 109.4, 40.3, 34.4, 34.8, 23.8.

Synthesis of (2S,5R)-VIII-8

To a solution of (2R,5R)-2-tert-butyl-5-phenyl-1,3-dioxolan-4-one (1 eq.) in THF (0.6M), cooled at −78° C., LHMDS (1.5 eq.) was added drop wise. The reaction mixture was stirred at this temperature for 30 min and than a solution of HMPA/THF (0.4 mL: 1.8/1) was added via syringe, followed by a solution of CH$_2$I$_2$ (3.3 eq.) in THF (3 mL). The temperature was than allowed to rise till −30° C. in 2 h and the mixture was quenched with sat. NH$_4$Cl and extracted with Et$_2$O. Silica gel column chromatography of the crude material afforded the pure compound in 70% yield.

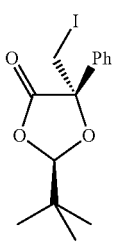 [SMILES: CC(C)(C)[C@H]1OC(=O)[C@@](CI)(c2ccccc2)O1]

(2S,5R)-VIII-8: $^1$H NMR (400 MHz, CDCl$_3$): 7.70-7.68 (m, 2H, ArH), 7.42-7.37 (m, 2H, ArH), 5.70 (s, 1H, CH), 3.71 (d, J=11.2 Hz, 1H, CH$_2$), 3.49 (d, J=11.2 Hz, 1H, CH$_2$), 0.93 (s, 9H, $^t$Bu).

EXAMPLE 2

Synthesis of XXIII-1 and XXIII-2

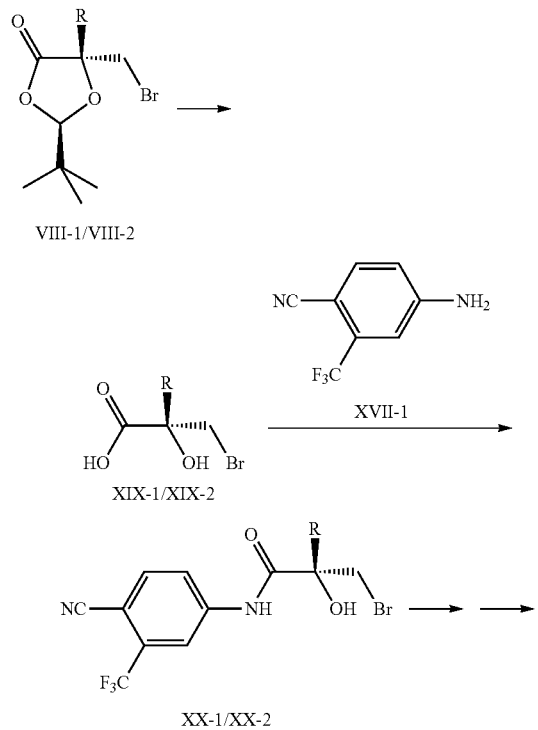

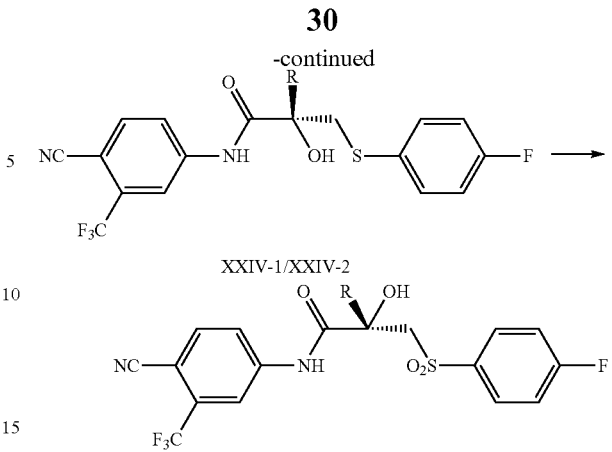

Synthesis of XIX (Representative Example)

Bromide (2S,5R)-VIII-1 was dissolved in a large excess of 6N HCl (6 eq.) and refluxed for 4 h. The reaction mixture was than cooled at room temperature, treated with brine and extracted (3 times) with ethyl acetate (EtOAc). The organic layer was than washed with a saturated solution of NaHCO$_3$ and the aqueous solution was than acidified with HCl (pH=2) and extracted with EtOAc. The compound could be processed to the next step without any further purification.

The same procedure was exploited for the synthesis of (R)-XIX-2 and can, in principle be applied to all other derivatives.

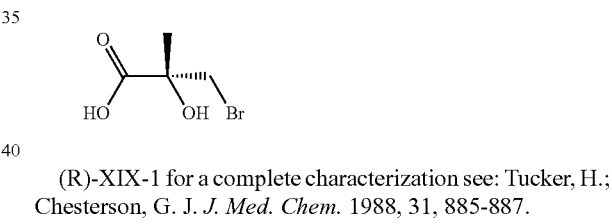

(R)-XIX-1 for a complete characterization see: Tucker, H.; Chesterson, G. J. *J. Med. Chem.* 1988, 31, 885-887.

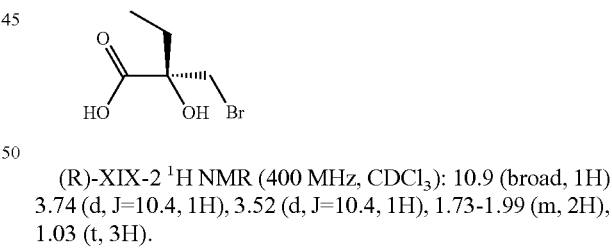

(R)-XIX-2 $^1$H NMR (400 MHz, CDCl$_3$): 10.9 (broad, 1H) 3.74 (d, J=10.4, 1H), 3.52 (d, J=10.4, 1H), 1.73-1.99 (m, 2H), 1.03 (t, 3H).

Synthesis of XX (Representative Example)

To a solution of (R)-XIX-1 in DMA (dimethylacetamide) (0.55M) cooled at −10° C., 1.3 eq. of SOCl$_2$ were added drop wise under nitrogen atmosphere. The solution was stirred at this temperature for 3 h, and a solution of 4-amino-2-(trifluoromethyl)benzonitrile (XVII-1, Scheme 1) in DMA (1.2 eq. of amine in 1.5 mL of DMA) was added drop wise. The reaction mixture was than allowed to react at room temperature for 16 h. The solvent was than removed under reduced pressure, and the crude material was treated with saturated NaHCO$_3$ and extracted with EtOAc. The reaction crude was purified by silica gel column chromatography. Yield: 84%.

The same procedure was applied to the synthesis of (R)-XX-2.

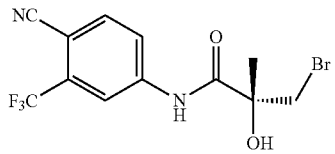 [SMILES: C[C@](O)(CBr)C(=O)Nc1ccc(C#N)c(C(F)(F)F)c1]

(R)-XX-1: known compound.

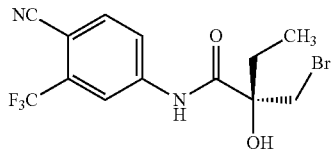 [SMILES: CC[C@](O)(CBr)C(=O)Nc1ccc(C#N)c(C(F)(F)F)c1]

(R)-XX-2 $^1$H NMR (400 MHz, CDCl$_3$): 9.03 (broad s, 1H) 8.10 (s, 1H), 7.96 (m, 1H), 7.80 (m, 1H), 3.99 (d, J=10.8, 1H), 3.58 (d, J=10.8, 1H), 3.07 (bs, 1H), 1.76-2.15 (m, 2H), 1.00 (t, 3H). $^{13}$C NMR (100 MHz, CDCl$_3$): 171.6, 141.4, 136.1, 134.6, 134.1 (q, J=32.5 Hz), 122.2, 117.5 (q, J=20 Hz), 115.7, 105.0, 78.7, 40.6, 31.3, 8.3.

Synthesis of XXIV (Representative Example)

To a suspension of NaH (60% mineral oil; 1.3 eq.) in dry THF cooled at 0-5° C., a solution of 4-fluorobenzenethiol (1.0 eq.) in THF was added drop wise. The reaction mixture was than stirred at room temperature for 30 min, after that, a solution of (R)-XX-1 (1 eq.) in THF was added drop wise at 0-5° C. The solution was than stirred at room temperature for 3-5 h and than quenched with dist. H$_2$O and saturated NH$_4$Cl. The organic phase was than extracted with EtOAc, and the crude material purified by silica gel column chromatography.

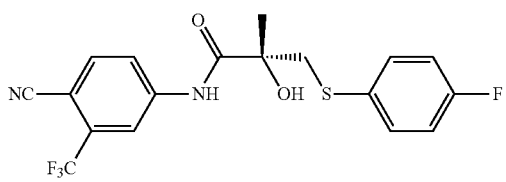 [SMILES: C[C@](O)(CSc1ccc(F)cc1)C(=O)Nc1ccc(C#N)c(C(F)(F)F)c1]

(R)-XXIV-1: Known compound. Yield: 88%.

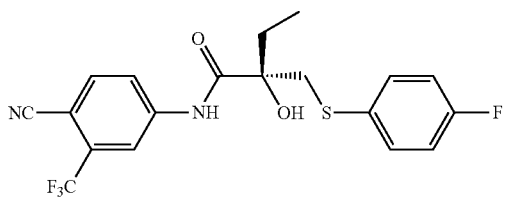 [SMILES: CC[C@](O)(CSc1ccc(F)cc1)C(=O)Nc1ccc(C#N)c(C(F)(F)F)c1]

(R)-XXIV-2: Yield: 85%; $^1$H NMR (400 MHz, CDCl$_3$): 8.97 (broad s, 1H) 7.90 (s, 1H), 7.74 (s, 2H), 7.37 (dd, J=8.4 2H), 6.85 (dd, J=8.4, 2H), 3.74 (d, J=14.0 Hz, 1H), 3.45 (b s, 1H), 3.08 (d, J=14.0 Hz, 1H) 1.86-2.00 (m, 1H), 1.63-1.76 (m, 1H), 0.93 (t, 3H). $^{13}$C NMR (100 MHz, CDCl$_3$) Relevant: 172.8, 161.5 (d, J=256 Hz), 141.3, 135.9, 134.8 (q, J=35 Hz) 134.0, 128.7, 121.8, 117.3 (q, J=5 Hz), 116.4 (d, J=22.1 Hz) 115.7, 104.7, 78.2, 45.1, 32.7, 8.0.

Synthesis of XXIII (Representative Example)

3 Equivalents of m-chloro perbenzoic acid (mCPBA) were added to a solution of (R)-XXIV-1 in CH$_2$Cl$_2$ (0.1 Mm). The reaction mixture was stirred at room temperature for 12 h. The solution was than diluted with EtOAc, and the organic layer was washed with aqueous Na$_2$SO$_3$ followed by saturated NaHCO$_3$. The crude compound was purified by silica gel column chromatography or by crystallization.

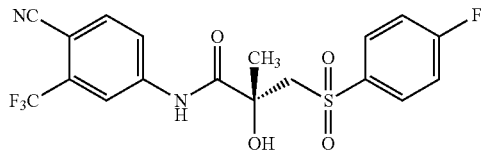 [SMILES: C[C@](O)(CS(=O)(=O)c1ccc(F)cc1)C(=O)Nc1ccc(C#N)c(C(F)(F)F)c1]

(R)-XXIII-1, (R)-Bicalutamide.

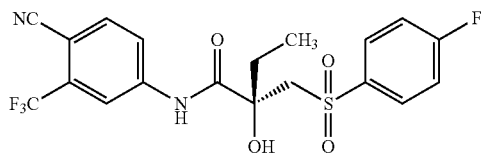 [SMILES: CC[C@](O)(CS(=O)(=O)c1ccc(F)cc1)C(=O)Nc1ccc(C#N)c(C(F)(F)F)c1]

(R)-XXIII-2: Yield=90%; $^1$H NMR (400 MHz, CDCl$_3$): 9.05 (broad s, 1H) 7.97 (s, 1H), 7.85-7.91 (m, 2H), 7.79-7.90 (m, 2H), 7.12-7.19 (m, 2H), 4.94 (s, 1H) 3.95 (d, J=14.4 Hz, 1H), 3.45 (d, J=14.4 Hz), 1.78-2.00 (m, 2H) 0.95 (t, 3H). $^{13}$C NMR (100 MHz, CDCl$_3$) Relevant: 171.2, 166.5 (d, J=257 Hz), 141.1, 136.1, 135.2, 134.8 (q, J=35 Hz) 131.1 (d, J=37.2 Hz), 122.0 (q), 121.9, 117.3 (q, J=5 Hz), 117.0 (d, J=22.1 Hz) 115.5, 104.8, 77.1, 60.8, 33.9, 7.5.

EXAMPLE 3

Synthesis of XXIII-3 to XXIII-6

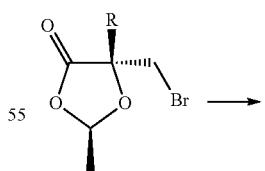

VIII-3/VIII-6

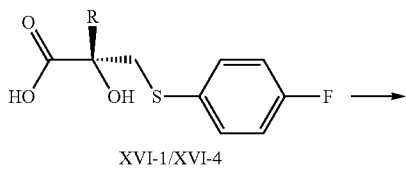

XVI-1/XVI-4

-continued

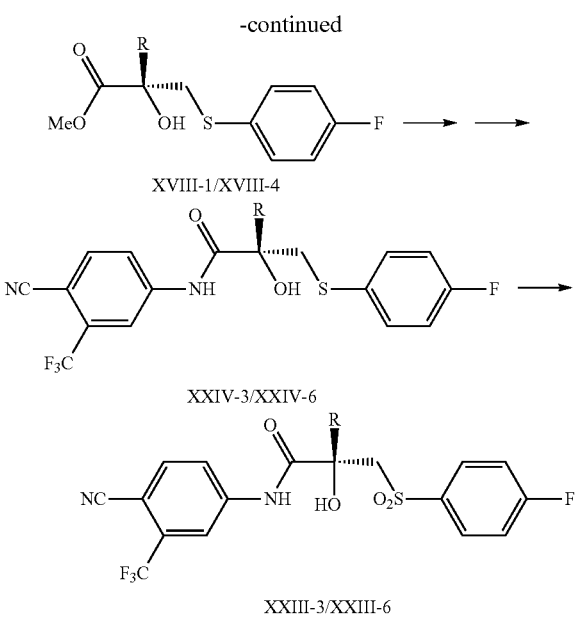

XVIII-1/XVIII-4

XXIV-3/XXIV-6

XXIII-3/XXIII-6

Synthesis of XVI (Representative Example)

A solution of (R)-VIII-3 (1 eq.) in a 1/1 $^i$PrOH/1N NaOH mixed solvent was stirred at room temperature for 3 h, than 4-fluorobenzenethiol (1.6 eq) was added drop wise. The reaction mixture was additionally stirred a to room temperature for 16 h. The solution was than treated with 1 M HCl (till pH=8) and extracted twice with $CH_2Cl_2$. The pure compound was obtained by crystallization ($CHCl_3$/petrol ether).

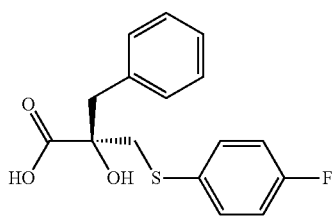 [SMILES: O=C(O)[C@@](O)(CSc1ccc(F)cc1)Cc1ccccc1]

(R)-XVI-1: $^1$H NMR (400 MHz, $CDCl_3$): 7.44-7.41 (m, 2H, ArH), 7.27-7.20 (m, 5H, ArH), 6.97 (t, J=8.8 Hz, 2H, ArH), 3.43 (d, J=13.6 Hz, 1H, $CH_2$), 3.26 (d, J=14.0 Hz, 1H, $CH_2$), 3.12 (d, J=13.6 Hz, 1H, $CH_2$), 3.01 (d, J=13.6 Hz, 1H, $CH_2$). $^{13}$C NMR (100 MHz, $CDCl_3$): 177.9, 134.7, (133.9, 133.8; d), 130.4, 128.6, 127.6, (116.4, 116.2; d), 78.6, 44.9, 44.8.

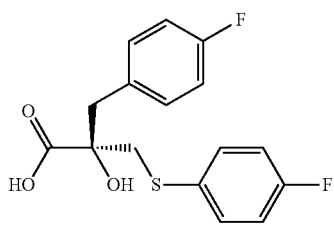 [SMILES: O=C(O)[C@@](O)(CSc1ccc(F)cc1)Cc1ccc(F)cc1]

(R)-XVI-2: Yield: 98%; $^1$H NMR (400 MHz, $CDCl_3$): 7.46-7.42 (m, 2H, ArH), 7.27-7.20 (m, 2H, ArH), 7.02-6.95 (m, 4H, ArH), 3.47 (d, J=18.0 Hz, 1H, $CH_2$), 3.25 (d, J=13.6 Hz, 1H, $CH_2$), 3.10 (d, J=13.6 Hz, 1H, $CH_2$), 2.99 (d, J=13.6 Hz, 1H, $CH_2$). $^{13}$C NMR (100 MHz, $CDCl_3$): 178.9, (163.7, 161.2, d), (161.3, 163.6, d), (134.0, 133.9, d), (132.0, 131.9, d), (130.5, 130.4, 130.3, t), (116.5, 116.3, d), (115.6, 115.3, d), 78.6, 44.9, 43.9.

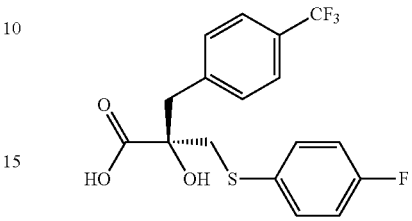

(R)-XVI-3: $^1$H NMR (400 MHz, $CDCl_3$): 7.51 (d, J=8.4 Hz, 2H, ArH), 7.45-7.41 (m, 2H, ArH), 7.34 (d, J=8.0 Hz, 2H, ArH), 6.97 (t, J=8.4 Hz, 2H, ArH), 3.43 (d, J=13.6 Hz, 1H, $CH_2$), 3.25 (d, J=14.0 Hz, 1H, $CH_2$), 3.10 (q, J=13.6 Hz, 1H, $CH_2$).

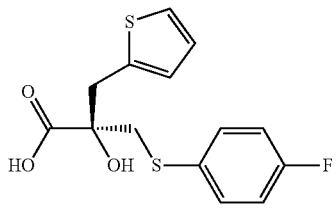 [SMILES: O=C(O)[C@@](O)(CSc1ccc(F)cc1)Cc1cccs1]

(R)-XVI-4: $^1$H NMR (400 MHz, $CDCl_3$): 7.45-7.42 (m, 2H, ArH), 7.20 (d, J=5.2 Hz, 1H, ArH), 7.0-6.93 (m, 3H, ArH), 6.86 (d, J=3.6 Hz, 1H, ArH), 3.40 (d, J=14.0 Hz, 1H, $CH_2$), 3.36 (d, J=14.8 Hz, 1H, $CH_2$), 3.27 (d, J=14.0 Hz, 1H, $CH_2$), 3.23 (d, J=14.4 Hz, 1H, $CH_2$). $^{13}$C NMR (100 MHz, $CDCl_3$): 177.7, (163.7, 161.3; d) 135.8, (134.0, 133.9; d), (130.5, 130.4; d), 127.9, 127.0, 125.7, (116.5, 116.3; d), 78.3, 44.5, 39.2.

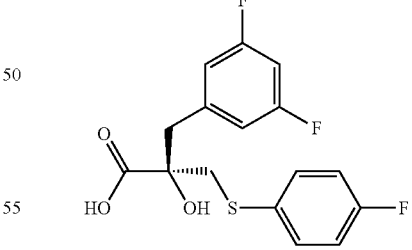

(R)-XVI-5: $^1$H NMR (400 MHz, $CDCl_3$): 7.44-7.41 (m, 2H, ArH), 6.98 (t, J=8.8 Hz, 2H, ArH), 6.78-6.68 (m, 4H, ArH), 3.40 (d, J=14.0 Hz, 1H, $CH_2$), 3.22 (d, J=14.0 Hz, 1H, $CH_2$), 3.06 (d, J=14.0 Hz, 1H, $CH_2$), 3.00 (d, J=14.0 Hz, 1H, $CH_2$). $^{13}$C NMR (100 MHz, $CDCl_3$): 177.7, (164.1, 161.6; dt; $J^1$=247.1 Hz, $J^2$=12.7 Hz), 138.4, (134.1, 134.0; d, J=8.0 Hz), (116.5, 116.3; d, J=21.7 Hz), (113.3; t, J=18.3 Hz), (103.1; t, J=25.1 Hz), 72.2, 45.1, 44.1.

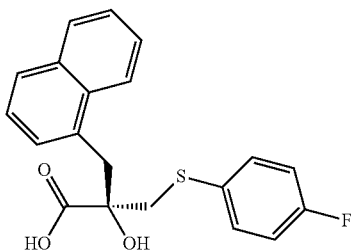 [SMILES: O=C(O)[C@@](O)(CSc1ccc(F)cc1)Cc1cccc2ccccc12]

(R)-XVI-6: $^1$H NMR (400 MHz, CDCl$_3$): 7.79-7.68 (m, 4H, ArH), 7.47-7.41 (m, 4H, ArH), 7.35 (d, J=8.4 Hz, 1H, ArH), 6.96 (t, J=9.6 Hz, 2H, ArH), 3.48 (d, J=13.6 Hz, 1H, CH$_2$), 3.29 (d, J=14.0 Hz, 2H, CH$_2$), 3.17 (d, J=13.2 Hz, 1H, CH$_2$). $^{13}$C NMR (100 MHz, CDCl$_3$): 177.1, (163.7, 161.3; d), (134.0, 133.9; d), 133.5, 132.8, 132.2, 129.3, 128.4, 128.2, (127.9, 127.8; d), 126.4, 126.1, (116.5, 116.2; d), 78.7, 44.9, 44.8.

Synthesis of XVIII (Representative Example)

To a solution of (R)-XVI-1 (1 eq.) in MeOH/Toluene mixed solvent (1/1, 1 mL per mmol), Me$_3$SiCH=N$_2$ (2M in Et$_2$O) (1.5 eq.) was added drop wise at room temperature. The reaction mixture was than stirred for 1 h and than carefully quenched with acetic acid and extracted with EtOAc. The crude material was purified by silice gel column chromatography.

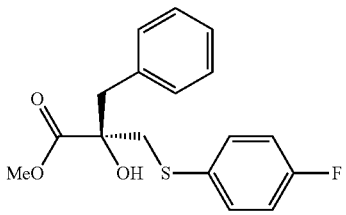 [SMILES: COC(=O)[C@@](O)(CSc1ccc(F)cc1)Cc1ccccc1]

(R)-XVIII-1: $^1$H NMR (400 MHz, CDCl$_3$): 7.43-7.39 (m, 2H, ArH), 7.26-7.24 (m, 3H, ArH), 7.17-7.16 (m, 2H, ArH), 6.97 (t, J=8.4 Hz, 2H, ArH), 3.52 (s, 3H, CH$_3$), 3.41 (d, J=14.0 Hz, 1H, CH$_2$), 3.23 (d, J=14.0 Hz, 1H, CH$_2$), 3.06 (d, J=13.2 Hz, 1H, CH$_2$), 2.99 (d, J=13.2 Hz, 1H, CH$_2$).

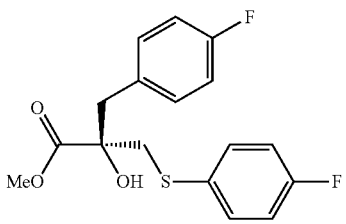 [SMILES: COC(=O)[C@@](O)(CSc1ccc(F)cc1)Cc1ccc(F)cc1]

(R)-XVIII-2: Yield: 98%; [α]$^{20}_D$ +15.3 (c 0.27, CHCl$_3$); $^1$H NMR (400 MHz, CDCl$_3$): 7.44-7.41 (m, 2H, ArH), 7.16-7.13 (m, 2H, ArH), 7.01-6.93 (m, 4H, ArH), 3.52 (s, 3H, CH$_3$), 3.39 (d, J=14.0 Hz, 1H, CH$_2$), 3.21 (d, J=14.0 Hz, 1H, CH$_2$), 3.03 (d, J=13.6 Hz, 1H, CH$_2$), 2.96 (d, J=13.6 Hz, 1H, CH$_2$). $^{13}$C NMR (100 MHz, CDCl$_3$): 167.9, (163.6, 163.5; d), 161.1, (133.9, 133.8; d), 132.7, (131.8, 131.7; d), 130.9, 130.8, (116.3, 116.1; d), 115.4, 115.2; d), 78.5, 52.8, 45.2, 44.1,

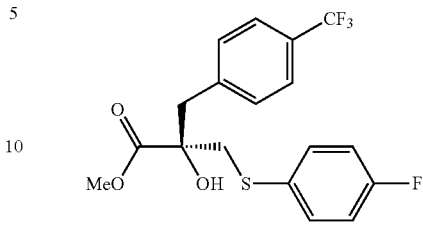

(R)-XVIII-3: $^1$H NMR (400 MHz, CDCl$_3$): 7.51 (d, J=7.6 Hz, 2H, ArH), 7.43-7.40 (m, 2H, ArH), 7.29 (d, J=8.0 Hz, 2H, ArH), 6.98 (t, J=8.8 Hz, 2H, ArH), 3.51 (s, 3H, CH$_3$), 3.40 (d, J=13.6 Hz, 1H, CH$_2$), 3.21 (d, J=13.6 Hz, 1H, CH$_2$), 3.10 (d, J=13.6 Hz, 1H, CH$_2$), 3.04 (d, J=13.6 Hz, 1H, CH$_2$). $^{13}$C NMR (100 MHz, CDCl$_3$): 173.9, (163.6, 161.2; d), 139.4, (134.0, 133.9; d), 130.6, (129.8, 129.5, d), (125.7, 125.4, 125.3, 125.2; q), (116.4, 116.1, d), 78.3, 52.9, 45.4, 44.5.

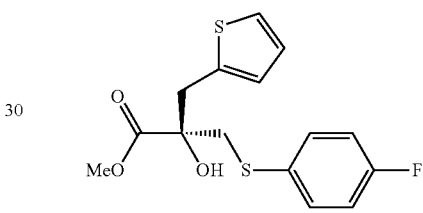

(R)-XVIII-4: Yield: 98%; [α]$^{20}_D$ +29.5 (c 0.21, CHCl$_3$); $^1$H NMR (400 MHz, CDCl$_3$): 7.44-7.41 (m, 2H, ArH), 7.15 (dd; J$^1$=5.2 Hz, J$^2$=1.2 Hz, 1H, ArH), 6.98 (t, J=8.4 Hz, 2H, ArH), 6.93-6.91 (m, 1H, ArH), 6.84 (dd; J$^1$=3.2 Hz, J$^2$=0.4 Hz, 1H, ArH), 3.61 (s, 1H, OH), 3.54 (s, 3H, CH$_3$), 3.37 (d, J=14.0 Hz, 1H, CH$_2$), 3.31 (d, J=14.4 Hz, 1H, CH$_2$), 3.24 (d, J=13.6 Hz, 1H, CH$_2$), 3.20 (d, J=14.4 Hz, 1H, CH$_2$).

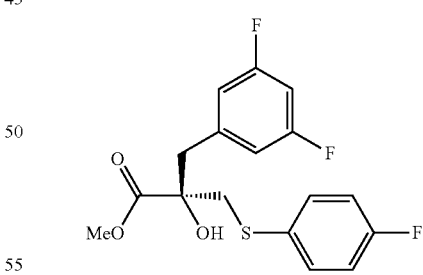

(R)-XVI-5: $^1$H NMR (400 MHz, CDCl$_3$): 7.84-7.78 (m, 2H, ArH), 6.98 (t, J=9.0 Hz, 2H, ArH), 6.62-6.73 (m, 4H, ArH), 3.52 (s, 3H, CH$_3$), 3.37 (d, J=14.0 Hz, 1H, CH$_2$), 3.20 (d, J=14.0 Hz, 1H, CH$_2$), 3.02 (d, J=11.2 Hz, 1H, CH$_2$), 2.96 (d, J=11.2 Hz, 1H, CH$_2$). $^{13}$C NMR (100 MHz, CDCl$_3$): 173.9, (164.1, 161.6; dt; J$^1$=246.6 Hz, J$^2$=12.7 Hz), 139.1, 134.0 (d, J=32.4 Hz), 130.6, 116.5 (d, J=22.5 Hz), 116.2 (d, J=21.7 Hz), (113.2, 113.0; dd; J$^1$=18.3 Hz, J$^2$=6.8 Hz), 102.9 (t, J=25.1 Hz) 78.2, 52.9, 45.4, 44.4.

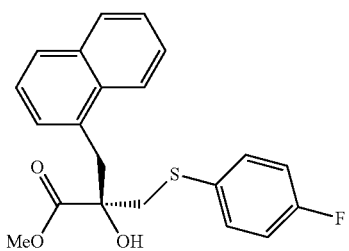 [SMILES: COC(=O)[C@@](O)(CSc1ccc(F)cc1)Cc1cccc2ccccc12]

(R)-XVIII-6: (98% yield) ¹H NMR (400 MHz, CDCl₃): 7.79-7.74 (m, 3H, ArH), 7.63 (s, 1H, ArH), 7.46-7.41 (m, 4H, ArH), 7.32 (d, J=8.4 Hz, 1H, ArH), 6.98 (t, J=8.8 Hz, 2H, ArH), 3.53 (s, 3H, CH₃), 3.45 (d, J=14.0 Hz, 1H, CH₂), 3.46 (s, 1H, OH), 3.28 (d, J=14.0 Hz, 1H, CH₂), 3.24 (d, J=14.0 Hz, 1H, CH₂), 3.16 (d, J=14.0 Hz, 1H, CH₂). ¹³C NMR (100 MHz, CDCl₃): 174.3, (163.6, 161.1; d), (133.9, 133.8; d), 133.5, (132.9, 132.7; d), 130.9, 129.1, 128.5, (128.0, 127.9, 127.8 t), (126.3, 126.0; d), (116.3, 116.1; d), 78.8, 52.8, 45.23, 45.21.

Synthesis of XXIV-1 (Representative Example)

To a solution of 4-amino-2-(trifluoromethyl)benzonitrile (XVII-1) (1.6 eq.) in THF (8.5 mL×mmol), cooled at −10° C., LHMDS (4.5 eq.) was added drop wise. The reaction mixture was than stirred at this temperature for 40 min and HMPA (10% of the total THF) was added to the solution. After 5 min stirring, a solution of the ester XVIII-1 (1 eq.) in THF (7 mL×mmol) was added to the reaction mixture. After 30 min at −10° C., the solution was stirred 12 h at room temperature. The reaction mixture was than quenched with 0.1N HCl and extracted with EtOAc. The crude material was purified by silica gel column chromatography. Yields range from 60 to 80%.

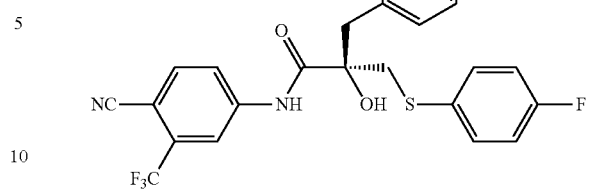

(R)-XXIV-4: ¹H NMR (400 MHz, CDCl₃): 8.53 (bs, 1H, NH), 7.72-7.68 (m, 2H, ArH), 7.51 (dd, J¹=8.4 Hz, J²=2.0 Hz, 1H, ArH), 7.39-7.36 (m, 2H, ArH), 7.17-7.14 (m, 2H, ArH), 6.94 (t, J=8.4 Hz, 2H, ArH), 6.87 (t, J=8.4 Hz, 2H, ArH), 3.89 (d, J=14.4 Hz, 1H, CH₂), 3.55 (bs, 1H, OH), 3.19 (d, J=14.0 Hz, 1H, CH₂), 3.07 (d, J=14.0 Hz, 1H, CH₂), 2.91 (d, J=13.6 Hz, 1H, CH₂). ¹³C NMR (100 MHz, CDCl₃): 172.1, (163.9, 163.7; d), (161.5, 161.2; d), 140.8, 135.9, (134.3, 134.2; d), (132.1, 132.0, d), (130.3, 130.2; d), (128.1, 128.0, d), (134.0, 123.6, 120.8, q), 121.8, (117.4, 117.3; d), (116.7, 116.4; d), (115.7, 115.6, 115.5, t), 105.1, 77.9, 44.7, 44.3

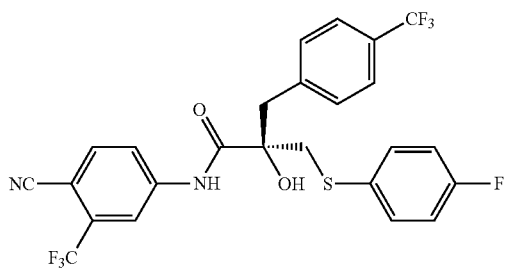

(R)-XXVI-5: ¹H NMR (400 MHz, CDCl₃): 8.47 (bs, 1H, NH), 7.69 (d, J=8.8 Hz, 2H, ArH), 7.61 (d, J=2.0 Hz, 1H, ArH), 7.49 (d, J=8.0 Hz, 1H, ArH), 7.45 (dd, J¹=8.4 Hz, J²=2.0 Hz, 1H, ArH), 7.39-7.36 (m, 2H, ArH), 7.29 (d, J=8.0 Hz, 2H, ArH), 6.86 (t, J=8.8 Hz, 2H, ArH), 3.92 (d, J=14.4 Hz, 1H, CH₂), 3.66 (bs, 1H, OH), 3.25 (d, J=9.6 Hz, 1H, CH₂), 3.07 (d, J=14.4 Hz, 1H, CH₂), 2.97 (d, J=13.2 Hz, 1H, CH₂).

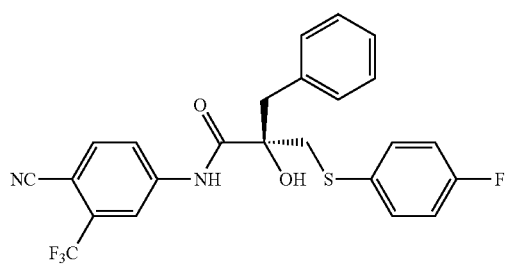 [SMILES: N#Cc1ccc(NC(=O)[C@@](O)(CSc2ccc(F)cc2)Cc2ccccc2)cc1C(F)(F)F]

(R)-XXVI-3: ¹H NMR (400 MHz, CDCl₃): 8.53 (broad s, 1H) 7.63-7.72 (m, 2H), 7.50-7.55 (m, 1H), 7.34-7.40 (m, 2H), 7.15-7.19 (m, 5H), 6.87 (dd, J=8.8 Hz, 1H) 3.87 (d, J=14.4 Hz, 1H), 3.45 (s, 1H). 3.22 (d, J=13.6 Hz, 1H), 3.11 (d, J=13.6 Hz, 1H), 2.95 (d, J=14.4 Hz, 1H, CH₂). ¹³C NMR (100 MHz, CDCl₃) Relevant: 172.1, 161.8 (d, J=248 Hz) 141.0, 135.8, 134.5, 134.2 (d, J=8.5 Hz), 130.5, 128.8, 127.7, 122.6 (q), 122.0, 117.6 (q, J=5 Hz), 116.5 (d, J=22.1 Hz) 115.6, 105.0.

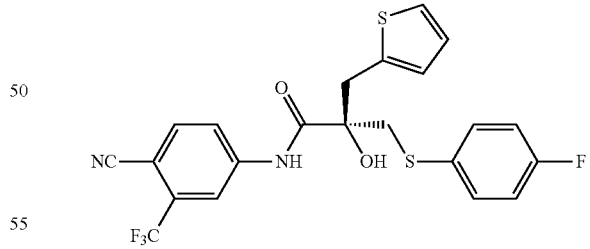

(R)-XXIV-6: ¹H NMR (400 MHz, CDCl₃): 8.69 (bs, 1H, NH), 7.73 (s, 1H, ArH), 7.71 (s, 1H, ArH), 7.61 (dd, J¹=8.8 Hz, J²=2.4 Hz, 1H, ArH), 7.39-7.36 (m, 2H, ArH), 7.18 (d, J=5.2 Hz, 1H, ArH), 6.93-6.85 (m, 4H, ArH), 3.80 (d, J=14.0 Hz, 1H, CH₂), 3.54 (bs, 1H, OH), 3.46 (d, J=14.8 Hz, 1H, CH₂), 3.20 (d, J=15.2 Hz, 1H, CH₂), 3.13 (d, J=14.4 Hz, 1H, CH₂). ¹³C NMR (100 MHz, CDCl₃): 172.0, 163.9, 161.4, 141.0, 135.9, 135.6, (134.3, 134.1, 134.0, 133.9; q), 128.4, 127.3, 126.1, 121.9, (117.5, 117.4; q), 116.6, 116.4, 77.7, 66.1, 44.2, 39.4, 29.9, 15.5.

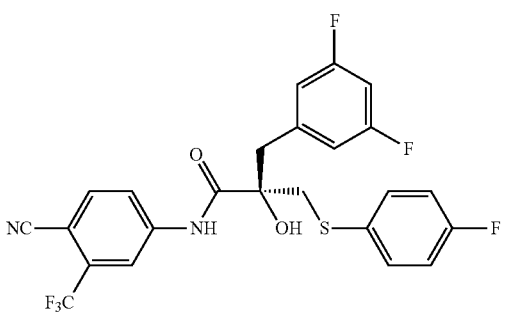 [SMILES: N#Cc1ccc(NC(=O)[C@@](O)(CSc2ccc(F)cc2)Cc2cc(F)cc(F)c2)cc1C(F)(F)F]

(R)-XXIV-7: $^1$H NMR (400 MHz, CDCl$_3$): 8.60 (s, 1H, NH), 7.72-7.67 (m, 2H, ArH), 7.55 (dd, J$^1$=8.4 Hz, J$^2$=2.0 Hz, 1H, ArH), 7.39-7.36 (m, 2H, ArH), 6.85 (t, J=8.4 Hz), 6.73 (dd, J$^1$=8.0 Hz, J$^2$=2.0 Hz, 2H, ArH), 6.62-6.65 (m, 1H, ArH), 3.89 (d, J=14.0 Hz, 1H, CH$_2$), 3.72 (s, 1H, OH), 3.17 (d, J=13.6 Hz, 1H, CH$_2$), 3.05 (d, J=14.0 Hz, 1H, CH$_2$), 2.90 (d, J=13.6 Hz, 1H, CH$_2$). $^{13}$C NMR (100 MHz, CDCl$_3$): 171.7, 163.0 (dt, J$^1$=247.9 Hz, J$^2$=12.7 Hz), 140.8, 138.4, 135.9, 138.4, 135.9, 134.3 (d, J=8.0 Hz), 121.9, 117.4 (q), 116.6 (d, J=21.7 Hz), 115.6, 113.4 (dd), 105.2, 103.2 (d, J=24.6 Hz), 77.6, 44.7, 44.6.

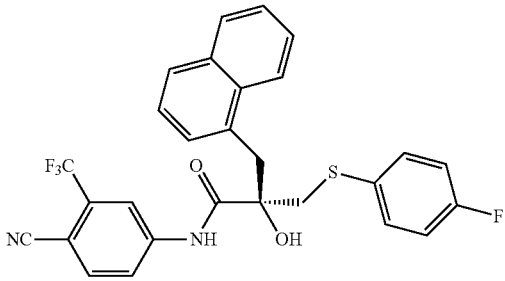 [SMILES: N#Cc1ccc(NC(=O)[C@@](O)(CSc2ccc(F)cc2)Cc2cccc3ccccc23)cc1C(F)(F)F]

(R)-XXVI-8: $^1$H NMR (400 MHz, Aceton): 9.62 (s, 1H, NH), 8.22 (s, 1H, ArH), 8.02 (d, J=7.3 Hz, 1H, ArH), 7.91 (d, J=7.3 Hz, 1H, ArH), 7.80-7.63 (m, 4H, ArH), 7.47-7.41 (m, 5H, ArH), 6.98 (t, J=8.3 Hz, 2H, ArH), 5.20 (s, 1H, OH), 3.80 (d, J=13.6 Hz, 1H, CH$_2$), 3.45 (d, J=13.6 Hz, 1H, CH$_2$), 3.40 (d, J=13.6 Hz, 1H, CH$_2$), 3.25 (d, J=13.6 Hz, 1H, CH$_2$). $^{13}$C NMR (100 MHz, Aceton): 173.0, (163.3, 160.8; d), 142.7, 136.1, (133.6, 133.4, 133.3; t), 132.7, 132.4, 31.6, 129.4, 128.9, (127.7, 127.6, 127.5; t), 126.1, 125.8, 124.2, 122.7, 121.5, 117.6 (q), (116.0, 115.8; d), 115.6, 103.5, 79.3, 45.3, 45.1.

Synthesis of XXIII-3

For this step it was followed the above reported procedure for the synthesis of compounds XXIII-1 and XXIII-2.
Eluant EtOAC/cHex=2/1; Yield 90%

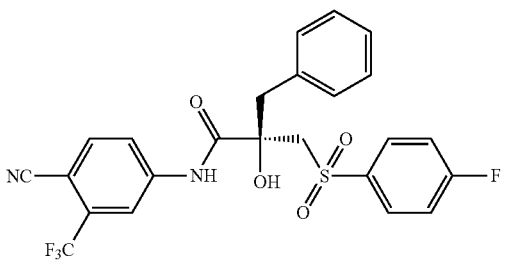 [SMILES: N#Cc1ccc(NC(=O)[C@](O)(Cc2ccccc2)CS(=O)(=O)c2ccc(F)cc2)cc1C(F)(F)F]

$[\alpha]^{20}_D$ +132 (c 0.4, CHCl$_3$);

(R)-XXIII-3: $^1$H NMR (400 MHz, CDCl$_3$): 8.65 (broad s, 1H) 8.1 (s, 1H), 7.97-8.01 (m, 1H), 7.84-7.91 (m, 2H), 7.70-7.75 (m, 2H), 7.51-7.63 (m, 2H), 7.40-7.46 (m, 1H) 7.12-7.26 (m, 3H), 5.0 (s, 1H). 4.12 (d, J=14.0 Hz, 1H), 3.44 (d, J=14.0 Hz, 1H), 3.11 (d, J=13.6 Hz, 1H), 3.03 (d, J=13.6 Hz, 1H). $^{13}$C NMR (100 MHz, CDCl$_3$) Relevant: 170.8, 166.4 (d, J=248 Hz), 140.0, 135.9, 135.1, 134.4 (q, J=35 Hz), 134.1, 133.3, 131.1 (d, J=37.2 Hz), 130.7, 130.5, 130.1, 128.8, 128.5, 128.1, 122.3, 117.6 (q, J=5 Hz), 117.0 (d, J=22.1 Hz) 115.5, 105.4, 77.0, 60.7, 46.5.

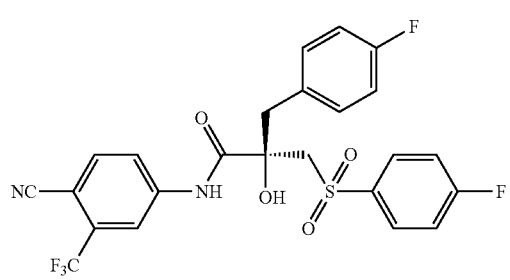 [SMILES: N#Cc1ccc(NC(=O)[C@](O)(Cc2ccc(F)cc2)CS(=O)(=O)c2ccc(F)cc2)cc1C(F)(F)F]

$[\alpha]^{20}_D$ +64.4 (c 0.29, CHCl$_3$);

(R)-XXIII-4: $^1$H NMR (400 MHz, CDCl$_3$): 8.64 (bs, 1H, NH), 7.89-7.86 (m, 2H, ArH), 7.74 (d, J=8.4 Hz, 2H, ArH), 7.54 (d, J=8.0 Hz, 2H, ArH), 7.17-7.13 (m, 4H, ArH), 6.94 (t, J=8.4 Hz, 2H, ArH), 5.11 (s, 1H, OH), 4.05 (d, J=14.4 Hz, 1H, CH$_2$), 3.40 (d, J=14.4 Hz, 1H, CH$_2$), 3.10 (d, J=13.6 Hz, 1H, CH$_2$) 3.01 (d, J=14.0 Hz, 1H, CH$_2$). $^{13}$C NMR (100 MHz, CDCl$_3$): 170.4, 140.6, 135.7, (132.1, 132.1; d), (131.0, 130.9; d), 128.9, 121.9, (117.4, 117.3; d), (116.9, 16.7; d), (115.4, 115.2; d), 77.4, 60.4, 45.5.

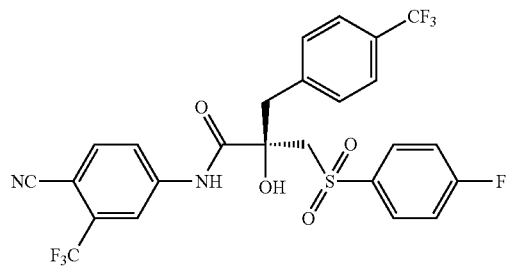 [SMILES: N#Cc1ccc(NC(=O)[C@](O)(Cc2ccc(C(F)(F)F)cc2)CS(=O)(=O)c2ccc(F)cc2)cc1C(F)(F)F]

(R)-XXIII-5: $^1$H NMR (400 MHz, CDCl$_3$): 8.00-7.97 (m, 2H, ArH), 7.9 (d, J=1.6 Hz, 1H, ArH), 7.81 (d, J=8.4 Hz, 1H, ArH), 7.73 (dd, J$_1$=8.4 Hz, J$_2$=2.0 Hz, 1H, ArH), 7.44 (d, J=8.4 Hz, 1H, ArH), 7.32 (d, J=8.4 Hz, 1H, ArH), 7.23 (t, J=8.8 Hz, 1H, ArH), 5.48 (s, 1H, OH), 4.24 (d, J=14.8 Hz, 1H, CH$_2$), 3.70 (d, J=14.4 Hz, 1H, CH$_2$), 3.14 (d, J=13.6 Hz, 1H, CH$_2$), 2.99 (d, J=13.6 Hz, 1H, CH$_2$). $^{13}$C NMR (100 MHz, CD$_3$OD): 171.2, 167.2, 164.7, 142.5, 139.5, (137.2, 137.1; d), 136.1, (131.9, 131.8; d), 131.4, (124.98, 124.94, 124.90, 124.86; q), 123.1, (117.8, 117.7; d), (116.4, 116.2; d), 115.6, 103.9, 76.8, 62.6, 45.8, 34.1, 22.3, 13.6.

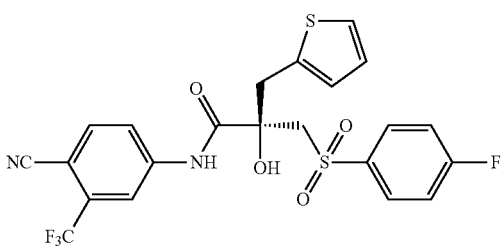 [SMILES: N#Cc1ccc(NC(=O)[C@](O)(Cc2cccs2)CS(=O)(=O)c2ccc(F)cc2)cc1C(F)(F)F]

[α]²⁰$_D$ +87.0 (c 0.28, CHCl₃);
(R)-XXIII-6: ¹H NMR (400 MHz, CDCl₃): 8.84 (bs, 1H, NH), 7.89-7.86 (m, 2H, ArH), 7.80 (d, J=1.6 Hz, 1H, ArH), 7.45 (d, J=8.4 Hz, 1H, ArH), 7.63 (dd, J₁=8.4 Hz, J₂=2.0 Hz, 1H, ArH), 7.21 (dd, J₁=5.2 Hz, J₂=1.2 Hz, 1H, ArH), 7.15 (t, J=8.4 Hz, 1H, ArH), 6.92 (t, J=5.2 Hz, 1H, ArH), 6.85 (d, J=3.2 Hz, 1H, ArH), 5.02 (s, 1H, OH), 4.04 (d, J=14.8 Hz, 1H, CH₂), 3.44 (d, J=14.4 Hz, 1H, CH₂), 3.34 (d, J=14.4 Hz, 1H, CH₂), 3.28 (d, J=14.8 Hz, 1H, CH₂). ¹³C NMR (100 MHz, CDCl₃): 170.3, 167.6, 164.9, 140.6, 135.7, (134.8, 134.7; d), (134.2, 134.0, d), 133.9, (131.0, 130.9; d), 128.6, 127.0, 126.3, 123.3, 121.9, 120.6, (117.4, 117.3; d), 117.2, (116.9, 116.7; d), 115.3, 105.2, 76.3, 59.7, 40.5.

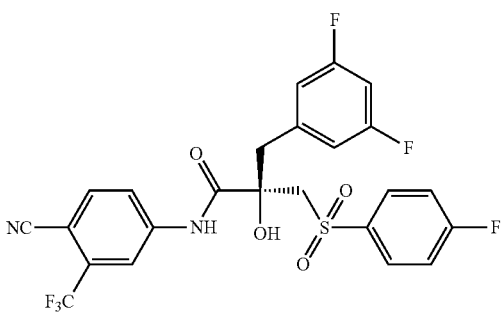 [SMILES: N#Cc1ccc(NC(=O)[C@](O)(Cc2cc(F)cc(F)c2)CS(=O)(=O)c2ccc(F)cc2)cc1C(F)(F)F]

[α]²⁰$_D$ +134 (c 0.30, CHCl₃);
(R)-XXIII-9: ¹H NMR (400 MHz, CDCl₃): 8.76 (s, 1H, NH), 7.90-7.87 (m, 2H, ArH), 7.78-7.62 (m, 2H, ArH), 7.64 (dd, J₁=8.4 Hz, J₂=2.0 Hz, 1H, ArH), 7.16 (t, J=8.0 Hz, 2H, ArH), 6.75-6.71 (m, 3H, ArH), 5.26 (1H, OH), 4.03 (d, J=14.4 Hz, 1H, CH₂), 3.40 (d, J=14.4 Hz, 1H, CH₂), 3.12 (d, J=13.6 Hz, 1H, CH₂), 3.03 (d, J=14.4 Hz, 1H, CH₂). ¹³C NMR (100 MHz, CDCl₃): 170.2, (167.9, 165.3, 164.3, 164.1, 161.8, 161.6; td), 140.6, 137.1, 136.0, 134.8, 131.1, (d, J=9.8 Hz), 122.2, 117.5 (q, J=5.1 Hz), 117.2 (d, J=22.5 Hz), 115.4, 113.8 (dd), 105.7, 103.6 (t, J=25.1 Hz), 76.9, 60.3, 45.7.

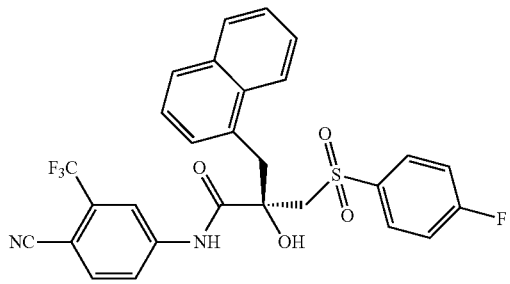 [SMILES: N#Cc1ccc(NC(=O)[C@](O)(Cc2cccc3ccccc23)CS(=O)(=O)c2ccc(F)cc2)cc1C(F)(F)F]

Yield 80%, [α]²⁰$_D$ +81 (c 0.30, Aceton);
(R)-XXIII-10: ¹H NMR (400 MHz, CDCl₃): 8.64 (s, 1H, NH), 7.87 (dd, J₁=8.8 Hz, J₂=4.8 Hz, 2H, ArH), 7.73-7.61 (m, 6H, ArH), 7.46-7.44 8m, 3H, ArH), 7.27 (d, J=8.4 Hz, 1H, ArH), 7.15 (t, J=8.8 Hz, 2H, ArH), 5.01 (s, 1H, OH), 4.15 (d, J=14.4 Hz, 1H, CH₂), 3.47 (d, J=14.8 Hz, 1H, CH₂), 3.28 (d, J=13.6 Hz, 1H, CH₂), 3.20 (d, J=14.0 Hz, 1H, CH₂). ¹³C NMR (100 MHz, CDCl₃): 170.9, (167.8, 165.2; d), 140.8, 135.8, 135.1, (133.4, 132.9; d), (131.3, 131.2; d), 130.8, 129.8, (128.4, 128.3, 127.8, 127.7; dd), (126.7, 126.5; d), 12.2, 117.6 (q), (117.2, 116.9; d), 115.5, 105.3, 77.2, 60.7, 46.6.

EXAMPLE 4

Synthesis of XXIII-7; XXIII-8 and XXIV-9

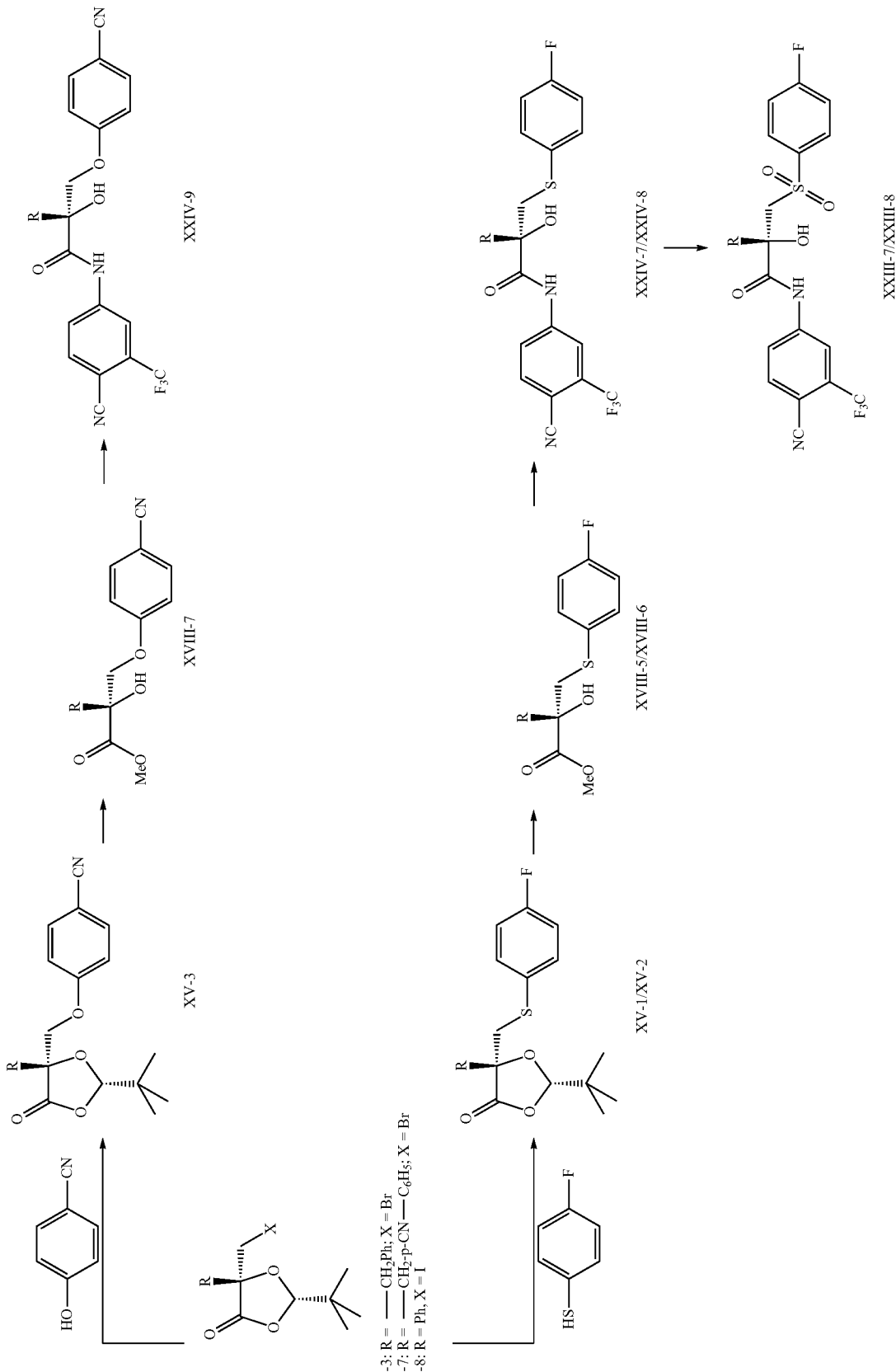

Synthesis of XV-1 (Representative Example)

To a solution of 4-[(2S,4R)-4-(bromomethyl)-2-tert-butyl-5-oxo-1,3-dioxolan-4-yl-methyl]benzonitrile [(2S,4R)-VIII-7, 1 eq.] in dry dimethylformamide [6.5 ml×mmol di(2S,4R)-VIII-7], K$_2$CO$_3$ (2.2 eq.) and 4-fluorobenzenethiol (2 eq.) were added at room temperature. The reaction mixture was than stirred for 3-4 h [NB: when p-CN-phenol is used instead of 4-fluorobenzenethiol, the temperature is raised to 100° C. for 10/12 hrs]. The reaction mixture was than treated with distilled water, extracted with EtOAc and purified by silica gel column chromatography.

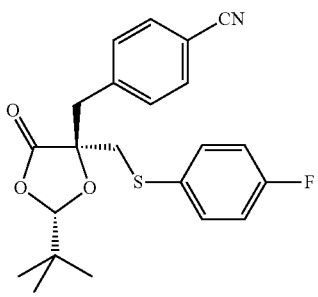

Y=88%; (R)-XV-1: $^1$H NMR (400 MHz, CDCl$_3$): 7.61 (d, J=8.0 Hz, 2H, ArH), 7.45-7.41 (m, 2H, ArH), 7.37 (d, J=8.0 Hz, 2H, ArH), 6.99 (t, J=8.4 Hz, 2H, ArH), 3.35 (d, J=13.6 Hz, 1H, CH$_2$), 3.28 (d, J=14.0 Hz, 1H, CH$_2$), 3.19 (d, J=14.0 Hz, 1H, CH$_2$), 3.16 (d, J=14.0 Hz, 1H, CH$_2$), 0.79 (s, 9H, $^t$Bu). $^{13}$C NMR (100 MHz, CDCl$_3$): 173.2, 163.8, 161.3, 139.9, (134.1, 134.0; d), (132.7, 132.6; d), 131.4, 130.9, 118.7, (116.5, 116.3; d), 111.9, 109.6, 83.6, 43.0, 40.4, 34.7, 23.5.

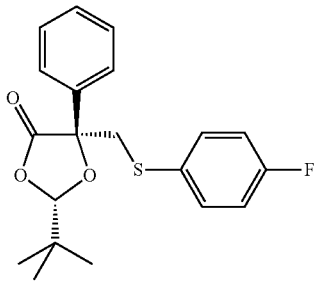

Y=85%; (R)-XV-2: $^1$H NMR (400 MHz, CDCl$_3$): 7.30 (d, J=8.4 Hz, 2H, ArH), 7.41-7.33 (m, 5H, ArH), 6.99 (t, J=8.4 Hz, 2H, ArH), 5.48 (s, 1H, CH), 3.51 (d, J=14.8 Hz, 1H, CH$_2$), 3.47 (d, J=14.8 Hz, 1H, CH$_2$), 0.89 (s, 9H, $^t$Bu). $^{13}$C NMR (100 MHz, CDCl$_3$): 172.5, 163.6, 161.2, 137.8, (133.3, 133.2; d), 130.8, (129.0, 128.9; d), (128.8, 128.72, 128.67, 128.6; q), (127.6, 1273; d), (125.8, 125.5; d), 125.1, (116.4, 116.2; d), (110.8, 110.6; d), 83.4, 46.2, 35.3, 23.7.

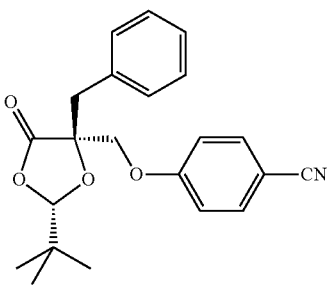

Y=45%; (S)-XV-3: $^1$H NMR (400 MHz, CDCl$_3$): 7.57 (d, J=8.8 Hz, 2H, ArH), 7.35-7.26 (m, 5H, ArH), 6.89 (t, J=8.8 Hz, 2H, ArH), 4.41 (s, 1H, CH), 4.25 (d, J=10.4 Hz, 1H, CH$_2$), 4.13 (d, J=10.4 Hz, 1H, CH$_2$), 3.20 (d, J=14.0 Hz, 1H, CH$_2$), 3.05 (d, J=14.0 Hz, 1H, CH$_2$), 0.89 (s, 9H, $^t$Bu). $^{13}$C NMR (100 MHz, CDCl$_3$): 172.7, 1661.5, 134.3, 133.6, 130.4, 129.0, 128.1, 115.5, 109.6, 105.1, 86.2, 70.0, 38.7, 34.8, 23.6.

Synthesis of XVIII-5 (Representative Example)

To a solution of (2S,4R)-XV-1 (1 eq.) in dry THF (7 mL×mmol of (2S,4R)-XV-1), 1.8 eq. of a 1M MeOH solution of sodium mathylate, were added dropwise at room temperature. After 2 h stirring, the reaction mixture was quenched with a 0.1 N solution of HCl, extracted with EtOAc and purified by silica gel column chromatography. Yields range from 85 to 95%.

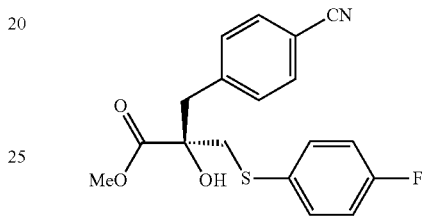

(R)-XVIII-5: $^1$H NMR (400 MHz, CDCl$_3$): 7.56 (d, J=8.4 Hz, 2H, ArH), 7.43-7.38 (m, 2H, ArH), 7.29 (d, J=4.4 Hz, 2H, ArH), 6.98 (t, J=8.4 Hz, 2H, ArH), 3.49 (s, 3H, CH$_3$), 3.39 (d, J=14.0 Hz, 1H, CH$_2$), 3.19 (d, J=13.6 Hz, 1H, CH$_2$), 3.09 (d, J=14.6 Hz, 1H, CH$_2$), 3.04 (d, J=13.6 Hz, 1H, CH$_2$). $^{13}$C NMR (100 MHz, CDCl$_3$): 173.8, 163.7, 161.2, 140.9, (134.1, 134.0; d), (132.2, 132.1; d), (131.3, 131.1; d), 119.0, (116.4, 116.2; d), 111.3, 78.2, 52.9, 45.5, 44.7.

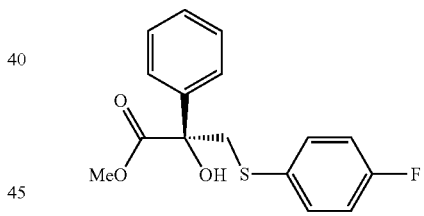

(R)-XVIII-6: $^1$H NMR (400 MHz, CDCl$_3$): 7.59 (d, J=8.0 Hz, 2H, ArH), 7.45-7.43 (m, 2H, ArH), 7.35-7.33 (m, 3H, ArH), 6.98 (t, J=8.4 Hz, 2H, ArH), 4.00 (bs, 1H, OH), 3.80 (d, J=13.6 Hz, 1H, CH$_2$), 3.74 (d, J=13.6 Hz, 1H, CH$_2$), 3.66 (s, 3H, CH$_3$), 3.41 (d, J=14.0 Hz, 1H, CH$_2$). $^{13}$C NMR (100 MHz, CDCl$_3$): 173.9, (163.6, 161.1, d); 140.4, (133.9, 133.8; d), (128.7, 128.6; d), (116.3, 116.1; d), 78.9, 53.4, 46.4.

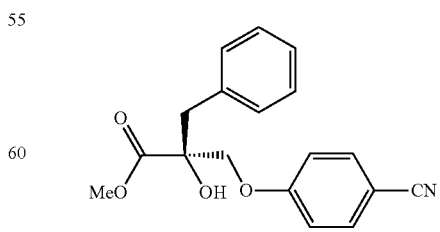

(S)-VIII-7: $^1$H NMR (400 MHz, CDCl$_3$): 7.57 (d, J=6.8 Hz, 2H, ArH), 7.30-7.21 (m, 5H, ArH), 6.94 (d, J=7.2 Hz, 2H, ArH), 4.33 (d, J=9.2 Hz, 1H, CH$_2$), 4.11 (d, J=9.2 Hz, 1H, CH$_2$), 3.76 (s, 3H, CH$_3$), 3.12 (d, J=13.6 Hz, 1H, CH$_2$), 3.05

(d, J=13.6 Hz, 1H, CH$_2$). $^{13}$C NMR (100 MHz, CDCl$_3$): 173.7, 161.9, (134.5, 134.2; d), 130.3, 128.6, 127.6, 115.7, 104.9, 78.0, 73.1, 53.3, 41.7.

Synthesis of XXIV-7 (Representative Example)

Lithium bis(trimethylsilyl)amide (LHMDS) (5 eq.) was added to a solution of 4-cyano-3-trifluoromethyl aniline (1.6 eq.) in dry THF (1 mL×mmol aniline) at −5° C. After stirring for 45 min., hexamethylphosphoric triamide (HMPA) (20% of the previously added, THF). After 5 min at −5° C. a solution of (R)-XVIII-5 in THF (1.5 mL×mmol of (R)-XVIII-5) was added drop wise. After 30 min at 0° C., the reaction mixture was allowed to warm up at the temperature value (25° C.) and than stirred for additional 6/7 h. The reaction was than quenched with an NH$_4$Cl saturated solution and extracted with ethyl acetate. Silica gel column chromatography or crystallization, afforded the pure compound.

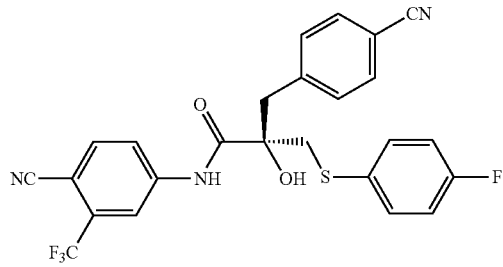 [SMILES: N#Cc1ccc(C[C@](O)(CSc2ccc(F)cc2)C(=O)Nc2ccc(C#N)c(C(F)(F)F)c2)cc1]

Y=60%; (R)-XXIV-7: $^1$H NMR (400 MHz, CDCl$_3$): 8.55 (bs, 1H, NH), 7.69 (d, J=8.8 Hz, 2H, ArH), 7.53-7.48 (m, 3H, ArH), 7.39-7.26 (m, 4H, ArH), 6.84 (t, J=8.2 Hz, 2H, ArH), 3.90 (d, J=14.4 Hz, 1H, CH$_2$), 3.78 (bs, 1H, OH), 3.26 (d, J=13.6 Hz, 1H, CH$_2$), 3.07 (d, J=14.4 Hz, 1H, CH$_2$), 2.95 (d, J=13.2 Hz, 1H, CH$_2$).
[α]$^{20}_D$ −123 (c 0.40, EtOH);

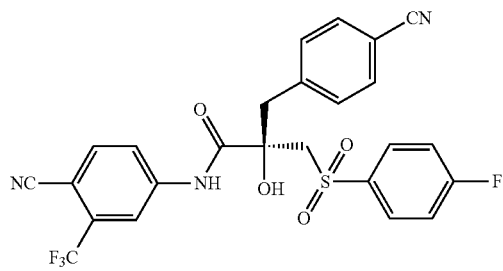 [SMILES: N#Cc1ccc(C[C@](O)(CS(=O)(=O)c2ccc(F)cc2)C(=O)Nc2ccc(C#N)c(C(F)(F)F)c2)cc1]

Y=58%; (R)-XXIV-8: $^1$H NMR (400 MHz, CDCl$_3$): 8.98 (bs, 1H, NH), 7.90 (s, 1H, ArH), 7.72 (d, J=1.2 Hz, 2H, ArH), 7.62 (dd, J$_1$=6.4 Hz, J$_2$=1.6 Hz, 2H, ArH), 7.39-7.31 (m, 4H, ArH), 6.88 (t, J=8.4 Hz). 4.22 (s, 1H, OH), 4.15 (d, J=14.4 Hz, 1H, CH$_2$), 3.38 (d, J=14.0 Hz, 1H, CH$_2$). $^{13}$C NMR (100 MHz, CDCl$_3$): 171.3, (164.0, 161.5; d), 141.5, 139.6, 135.9, (134.7, 134.6; d), (28.9, 128.8; d), 125.2, 121.9, (117.4, 116.6, 116.4, 115.6; q), 78.1, 47.1.

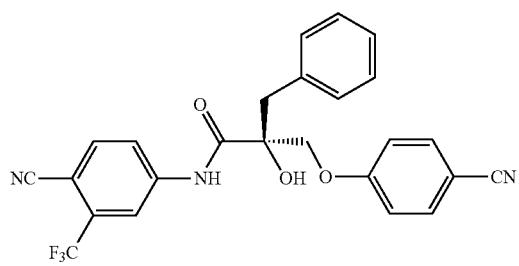 [SMILES: N#Cc1ccc(OC[C@@](O)(Cc2ccccc2)C(=O)Nc2ccc(C#N)c(C(F)(F)F)c2)cc1]

(R)-XXIV-9: $^1$H NMR (400 MHz, CDCl$_3$): 8.66 (bs, 1H, NH), 7.87 (s, 1H, ArH), 7.77 (d, J=4.0 Hz, 2H, ArH), 7.59 (d, J=8.8 Hz, 2H, ArH), 7.30-7.22 (m, 4H, ArH), 6.96 (d, J=9.2 Hz, 2H, ArH), 4.60 (d, J=9.2 Hz, 1H, CH$_2$), 4.10 (d, J=9.2 Hz, 1H, CH$_2$), 3.30 (d, J=13.6 Hz, 1H, CH$_2$), 3.10 (d, J=14.0 Hz, 1H, CH$_2$). $^{13}$C NMR (100 MHz, CDCl$_3$): 171.4, 161.0, 141.1, 136.1, 134.4, 133.8, 130.4, 129.0, 128.0, 122.2, 115.7, 105.8, 78.6, 72.1, 42.0.

For the synthesis of XXIII-7 and XXIII-8 it was followed the same procedure already reported for XXIII-1/XXIII-6
[α]$^{20}_D$ +142.5 (c 0.40, CHCl$_3$);

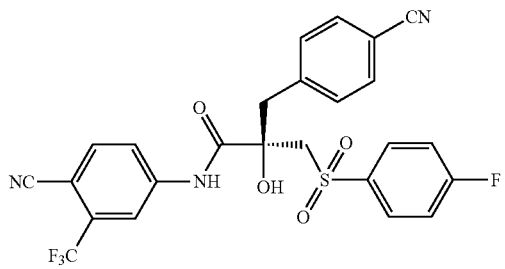 [SMILES: N#Cc1ccc(C[C@](O)(CS(=O)(=O)c2ccc(F)cc2)C(=O)Nc2ccc(C#N)c(C(F)(F)F)c2)cc1]

(R)-XXIII-7: $^1$H NMR (400 MHz, CDCl$_3$): 8.67 (bs, 1H, NH), 7.89-7.87 (m, 2H, ArH), 7.80 (s, 1H, ArH), 7.76 (d, J=8.4 Hz, 2H, ArH), 7.55 (d, J=8.0 Hz, 2H, ArH), 7.31 (d, J=8.0 Hz, 2H, ArH), 7.17 (t, J=8.0 Hz, 2H, ArH), 5.33 (s, 1H, OH), 4.02 (d, J=14.4 Hz, 1H, CH$_2$), 3.41 (d, J=14.4 Hz, 1H, CH$_2$), 3.22 (d, J=13.6 Hz, 1H, CH$_2$), 3.13 (d, J=14.0 Hz, 1H, CH$_2$). $^{13}$C NMR (100 MHz, CDCl$_3$) relevant: 170.1, (167.9, 165.3; d), 140.5, 139.0, 136.0, 134.8, 132.3, 131.6, (131.3, 131.2; d), 122.1, 118.6, (117.54, 117.5, 17.3, 117.2, q), 115.3, 112.1, 105.877.4, 60.4, 46.0.

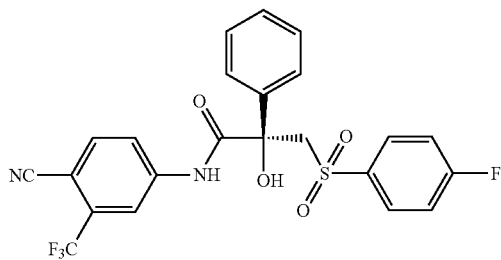 [SMILES: N#Cc1ccc(NC(=O)[C@@](O)(CS(=O)(=O)c2ccc(F)cc2)c2ccccc2)cc1C(F)(F)F]

(R)-XXIII-8: $^1$H NMR (400 MHz, CDCl$_3$): 9.02 (bs, 1H, NH), 7.96 (s, 1H, ArH), 7.76 (d, J=1.6 Hz, 2H, ArH), 7.71-7.67 (m, 2H, ArH), 7.53-7.51 (m, 2H, ArH), 7.28-7.26 (m, 3H, ArH), 7.07 (t, J=8.4 Hz, 2H, ArH), 5.78 (bs, 1H, OH), 4.24 (d, J=14.8 Hz, 1H, CH$_2$), 3.95 (d, J=14.8 Hz, 1H, CH$_2$). $^{13}$C NMR (100 MHz, CDCl$_3$): 169.9, (167.5, 164.9; d), 141.3, 137.9, 136.0, 135.2, (131.1, 131.0; d), (129.2, 129.0; d), 125.2, 122.1, (117.6, 117.5, 117.0, 116.7; q), 105.2, 77.0, 62.5.

EXAMPLE 5

Synthesis of XXIV-9 (Alternative Route)

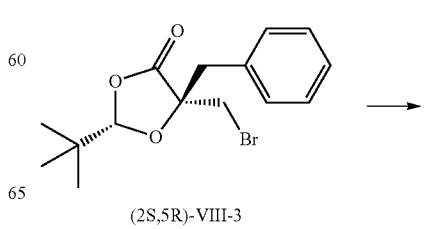

(2S,5R)-VIII-3

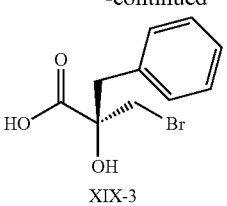

XIX-3

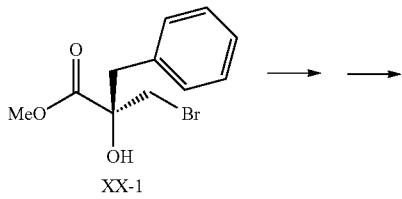

XX-1

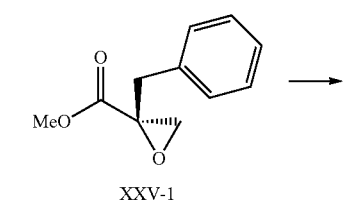

XXV-1

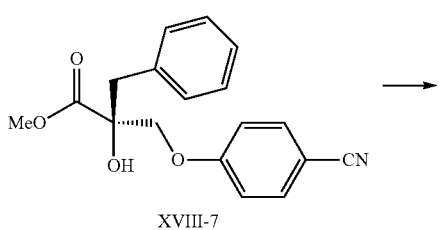

XVIII-7

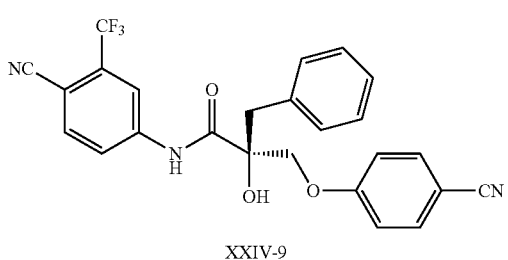

XXIV-9

Synthesis of (R)-XIX-3: bromide (2S,5R)-VIII-3 (1 eq.) was dissolved in a large excess of 6N HCl. The mixture was stirred under reflux for 4 h and than cooled at room temperature. Brine was than added to the solution and the organic layer extracted with EtOAc (3×). The organic phase was than washed with a saturated solution of NaHCO₃ and the aqueous layer acidified with concentrated HCl, and extracted with EtOAc. The pure carboxylic acid (R)-XIX-3 was obtained in quantitative yield without any further purification.

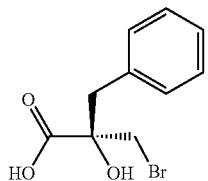 [SMILES: O=C(O)[C@@](O)(CBr)Cc1ccccc1]

(R)-XIX-3: $^1$H NMR (400 MHz, CDCl$_3$): 10.9 (broad, 1H) 7.38-7.20 (m, 3H, ArH), 7.20-7.17 (m, 2H, ArH), 3.83 (d, J=10.4, 1H), 3.54 (d, J=10.4, 1H), 3.18 (d, J=13.6, 1H), 3.06 (d, J=13.6, 1H).

$^{13}$C NMR (100 MHz, CDCl$_3$): 177.8, 134.3, 130.4, 128.7, 127.8, 77.9, 43.6, 38.6.

Synthesis of (R)-XX-1

To a solution of (R)-XIX-3 (1 eq.) in MeOH/Toluene mixed solvent (1/1, 1 mL per mmol), Me$_3$SiCH=N$_2$ (2M in Et$_2$O) (1.5 eq.) was added drop wise at room temperature. The reaction mixture was than stirred for 1 h and than carefully quenched with acetic acid and extracted with EtOAc. The crude material was purified by silica gel column chromatography. (Yield: 89%)

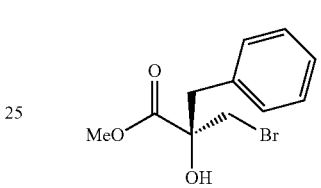

(R)-X-1: $^1$H NMR (400 MHz, CDCl$_3$): 7.38-7.20 (m, 3H, ArH), 7.20-7.17 (m, 2H, ArH), 3.78 (d, J=10.4 Hz, 1H, CH$_2$), 3.76 (s, 3H, CH$_3$), 3.52 (d, J=10.4 Hz, 1H, CH$_2$), 3.12 (d, J=10.4 Hz, 1H, CH$_2$), 3.02 (d, J=10.4 Hz, 1H, CH$_2$). $^{13}$C NMR (100 MHz, CDCl$_3$): 170.5, 133.4, 130.7, 128.7, 126.2, 79.5, 52.1, 42.6, 38.6.

To a suspension of NaH (3 eq.) in dry THF cooled at 0-5° C., a solution of (R)-XX-1 (1 eq.) in dry THF was added drop wise. The reaction mixture was than stirred for 30 min at room temperature and than 5 h at 60° C. The mixture as than carefully treated with H$_2$O and than extracted with Et$_2$O. the crude material was than purified by silica gel column chromatography (eluent: hexane/Et$_2$O=5/1). Yield=98%.

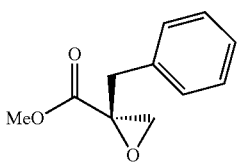 [SMILES: COC(=O)[C@]1(Cc2ccccc2)CO1]

(R)-XXV-1: $^1$H NMR (400 MHz, CDCl$_3$): 7.16-7.31 (m, 5H, ArH), 3.72 (s, 3H, CH$_3$), 3.38 (d, J=14.8 Hz, 1H, CH$_2$), 3.12 (d, J=14.4 Hz, 1H, CH$_2$), 3.04 (d, J=6.0 Hz, 1H, CH$_2$), 2.70 (d, J=5.6 Hz, 1H, CH$_2$). $^{13}$C NMR (100 MHz, CDCl$_3$): 170.9, 133.5, 131.0, 129.1, 125.6, 68.5, 53.2, 51.0, 38.9.

K$_2$CO$_3$ (2.5 eq.) was added to a solution of (R)-XXV-1 (1 eq.) in dry DMF (10 mL×mmol) at room temperature. After 10 min stirring p-CN-phenol (2.0 eq.) was added and the mixture was stirred at 100° C. for 5 h. After cooling at room temperature value water was added and extracted twice with Et$_2$O. The collected organic layers were than washed several times with distilled water and the crude material was than purified by silica gel column chromatography. Eluent (c-hex/Et₂O=6/1).
Yield=65%.

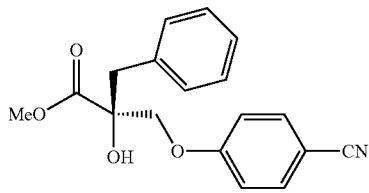 [SMILES: COC(=O)[C@@](O)(COc1ccc(C#N)cc1)Cc1ccccc1]

(R)-XVIII-7: Data analysis as reported above.

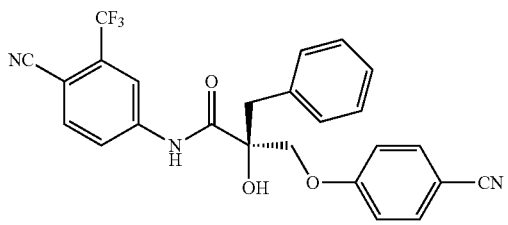 [SMILES: N#Cc1ccc(OC[C@@](O)(Cc2ccccc2)C(=O)Nc2ccc(C#N)c(C(F)(F)F)c2)cc1]

(R)-XXIV-9: Procedure and data analysis are reported above.

EXAMPLE 6

In vitro antitumor activity. Drug library screening was performed on LNCaP cells, a human prostate hormone sensible tumour cell line, and on LNCaP-AR line, derived from LNCaP, with hormone refractory prostate cancer (HRPC) features.
Materials and Methods
Cell Lines Evaluation of the cytotoxic effect of novel antiandrogens to select the most active compounds was performed in different in vitro human prostate cancer models: LNCaP cells, derived from a prostatic cancer lymph node lesion responsive to the antiandrogen treatment, obtained from the American Type Culture Collection (ATCC); LNCaP-AR line, derived from LNCaP with hormone resistant prostate cancer (HRPC) features, engineered to stably-express high levels of AR (a generous gift of Dr. Sawyers of the Memorial Sloan Kettering Institute, NY); PC3 and DU145, two hormone-refractory prostate cancer cell lines non expressing AR receptor, purchased from ATCC; HepG2, originally isolated from a primary hepatoblastoma of an 11-year-old boy, purchased from ATCC.

The cell lines were maintained as a monolayer at 37° C. and subcultured weekly. Culture medium was composed of RPMI 1640 supplemented with 10% fetal calf serum and 1% glutamine (Mascia Brunelli s.p.a., Milan, Italy). Cells were used in the exponential growth phase in all the experiments.
Compounds (R)-Bicalutamide and compounds (R)-XXIII-2, (R)-XXIII-3, (R)-XXIII-4, (R)-XXIII-5, (R)-XXIII-6, (R)-XXIII-7, (R)-XXIII-8, (R)-XXIII-9, (R)-XXIII-10, (R)-XXIV-9.

Compounds were dissolved in acetone or DMSO (AITES) (10 μM) and stored at −20° C. The cell culture containing acetone at the highest concentration was used as the control.
In Vitro Chemosensitivity Assay Sulforhodamine B (SRB) assay was used according to the method by Skehan et al. (JNCI, 1990). Briefly, cells were collected by trypsinization, counted and plated at a density of 5,000 cells/well in 96-well flat-bottomed microtiter plates (100 μl of cell suspension/well). In the chemosensitivity assay, experiments were run in octuplicate, and each experiment was repeated three times. The optical density (OD) of cells was determined at a wavelength of 490 nm by a colorimetric plate reader.
Data Analysis Growth inhibition and cytocidal effect of drugs were calculated according to the formula reported by Monks et al. (JNCI, 1991): $[(OD_{treated}-OD_{zero})/(OD_{control}-OD_{zero})]\times 100\%$, when $OD_{treated}$ is > to $OD_{zero}$. If $OD_{treated}$ is above $OD_{zero}$, treatment has induced a cytostatic effect, whereas if $OD_{treated}$ is below $OD_{zero}$, cell killing has occurred. The $OD_{zero}$ depicts the cell number at the moment of drug addition, the $OD_{control}$ reflects the cell number in untreated wells and the $OD_{treated}$ reflects the cell number in treated wells on the day of the assay.
TUNEL Assay Cells were fixed in 1% paraformaldehyde in PBS on ice for 15 min, suspended in ice cold ethanol (70%) and stored overnight at −20° C. Cells were then washed twice in PBS and resuspended in PBS containing 0.1% Triton X-100 for 5 min at 4° C. Thereafter, samples were incubated in 50 μl of solution containing TdT and FITC-conjugated dUTP deoxynucleotides 1:1 (Roche Diagnostic GmbH, Mannheim, Germany) in a humidified atmosphere for 90 min at 37° C. in the dark, washed in PBS, counterstained with propidium iodide (2.5 μg/ml, MP Biomedicals, Verona, Italy) and RNAse (10 Kunits/ml, Sigma Aldrich, Milan, Italy) for 30 min at 4° C. in the dark and analyzed by flow cytometry.
Flow Cytometric Analysis After the end of drug exposures, medium was removed and cells were detached from the flasks by trypsin treatment, washed twice with PBS and stained according to the different methods specified below. Flow cytometric analysis was performed using a FACS Canto flow cytometer (Becton Dickinson, San Diego, Calif.). Data acquisition and analysis were performed using FACSDiva software (Becton Dickinson). Samples were run in triplicate and 10,000 events were collected for each replica. Data were the average of three experiments, with errors under 5%.
Colony-Forming Cell Assay The colony-forming cell assay was used as previously described [Matta M R, Mangianti S, Rizzi S, Ratta M, Campanini E, Fortuna A, et al. Pharmacological purging of minimal residual disease from peripheral blood stem cell collections of acute myloblastic leukaemia patients: preclinical studies. Exp Hematol 1997; 25:1261-1269]. In brief, for each molecule, $5\times10^4$ cells were plated in duplicate in a complete culture medium (MethoCult H4434, StemCell Technologies, Vancouver, Canada) containing different concentrations (0.2, 2, and 20 μmol/l) of the compound. After 14 days of incubation in a humidified atmosphere of 5% $CO_2$ at the temperature of 37° C., granulocyte macrophage colony-forming unit (GM-CFU) aggregates of more than 50 cells were counted. Control cells were incubated under the same conditions but in drug-free medium.
Results and Comments FIG. 1 illustrates the cytotoxic effect and apoptotic activity of (R)-bicalutamide on LNCaP and LNCaP-AR cell lines.

FIGS. 2-11 show the cytotoxic activity of the derivative compounds of the invention on the LNCaP and LNCaP-AR cell lines. The authors examined the antitumour activity of the compounds for which the synthesis is described above, in the hormone-sensitive prostate cancer cell line LNCaP and in its derivative cell line LNCaP-AR, expressing high level of AR and with hormone refractory prostate cancer (HRPC) features. The novel compounds were tested at the increasing concentrations of 0.002, 0.2, 2.0, and 20.0 µM. The highest dose used was chosen on the basis of the clinically achievable peak plasma concentration reported in the literature for bicalutamide (Cockshott I D. Clin Pharmacokinet. 2004; 43(13): 855-78). After 144-hr exposure time the cytotoxic effect of the molecules was calculated according to the method of Monks et al. (Monks A, Scudiero D, Skehan P, et al. Feasibility of a high-flux anticancer drug screen using a diverse panel of cultured human tumor cell lines. J Natl Cancer Inst. 1991; 83: 757-66.)

Among the compounds with only cytostatic effect, (R)-XXIII-2 showed a weak cytostatic effect in both cell lines. In contrast, (R)-XXIII-3, (R)-XXIII-4, (R)-XXIII-6 and (R)-XXIII-8 showed to be able to suppress completely the cell growth in both cell lines at the highest concentration tested. (R)-XXIII-7 showed a cytocidal effect only on LNCaP cell. (R)-XXIII-5, (R)-XXIII-9, (R)-XXIII-10, (R)-XXIIV-9 showed cell killing activity in both cell lines.

FIGS. 12, 13, 14, 15 show the cytotoxic effect and apoptotic activity of the bicalutamide derivatives (R)-XXIII-2, (R)-XXIII-3, (R)-XXIII-4, (R)-XXIII-5, (R)-XXIII-6, R)-XXIII-7, (R)-XXIII-8, (R)-XXIII-9, (R)-XXIII-10, (R)-XXIV-9, on the LNCaP cell line or on the LNCaP-AR cell line.

The figures report the dose-effect curves, with the relative $GI_{50}$ and $LC_{50}$ values, and the dot plots showing the apoptotic fraction induced by the above compounds in LNCaP cells or LNCaP-AR cells.

The results of the figures are summarized in the following tables.

TABLE 1

Growth inhibition ($GI_{50}$) and cytocidal effects by 50% ($LC_{50}$) of bicalutamide and its derivative compounds observed in LNCaP and LNCaP-AR cells.[a]

| Compound | LNCaP µM $GI_{50}$ | LNCaP µM $LC_{50}$ | LNCaP-AR µM $GI_{50}$ | LNCaP-AR µM $LC_{50}$ |
|---|---|---|---|---|
| (R)-Bicalutamide | 1.8 | n.r.[a] | n.r. | n.r. |
| (R)-XXIII-2 | n.r. | n.r. | n.r. | n.r. |
| (R)-XXIII-3 | 1.8 | n.r. | 6.2 | n.r. |
| (R)-XXIII-4 | 7.0 | n.r. | 7.5 | n.r. |
| (R)-XXIII-5 | 2.0 | 16.2 | 1.9 | n.r. |
| (R)-XXIII-6 | 8.9 | n.r. | 9.8 | n.r. |
| (R)-XXIII-7 | 1.4 | 20 | 1.8 | n.r. |
| (R)-XXIII-8 | 11.8 | n.r. | 11.6 | n.r. |
| (R)-XXIII-9 | 5.7 | 19.7 | 8.2 | n.r. |
| (R)-XXIII-10 | 6.1 | 19.7 | 8.3 | n.r. |
| (R)-XXIV-9 | 6.4 | 17.4 | 7.1 | n.r. |

[a]n.r. = value not reached, i.e. when the drug is not able to induce the 50% of Growth Inibition ($GI_{50}$) or the 50% of cell killing ($LC_{50}$), also at the highest drug concentration tested.

The table lists the $GI_{50}$ and $LC_{50}$ values of Bicalutamide and of novel anti-androgen compounds observed in LNCaP and in LNCaP-AR cells. The control substance bicalutamide reaches $GI_{50}$ only in LNCaP cells (1.8 µM) whereas $LC_{50}$ values were not observed in the two cell lines used. The most effective compounds, (R)-XXIII-5, (R)-XXIII-7, (R)-XXIII-9, (R)-XXIII-10, (R)-XXIIV-9 showed to be able to reach $LC_{50}$ values only in LNCaP cells, ranging from 16.2 µM to 20.0 µM. Although a mitigation of their cytocidal effect was observed in LNCaP-AR (the hormone-resistant cell line derived from LNCaP and engineered to stably-express high levels of AR), the antitumor activity of the above compounds resulted even higher than that of the parental compound bicalutamide.

TABLE 2

Percentage of apoptotic cells, detected by TUNEL assay, in LNCaP and LNCaP-AR cells, induced by bicalutamide and its derivative compounds.

| Compound | Apoptotic cells (%) LNCaP | Apoptotic cells (%) LNCaP-AR |
|---|---|---|
| (R)-Bicalutamide | 2.1 | 5.7 |
| (R)-XXIII-2 | 10.8 | 7.9 |
| (R)-XXIII-3 | 9.0 | 6.5 |
| (R)-XXIII-4 | 8.5 | 9.7 |
| (R)-XXIII-5 | 99.8 | 91.9 |
| (R)-XXIII-6 | 8.4 | 9.9 |
| (R)-XXIII-7 | 19.8 | 16.4 |
| (R)-XXIII-8 | 10.8 | 8.1 |
| (R)-XXIII-9 | 97.7 | 98.1 |
| (R)-XXIII-10 | 96.5 | 97.6 |
| (R)-XXIV-9 | 92.1 | 92.4 |

The table compares the skill of (R)-bicalutamide and of its derivative compounds to induce apoptotis in LNCaP cells and the cell line LNCaP-AR, expressing high level of AR and with hormone refractory prostate cancer (HRPC) features. The cells, before TUNEL assay, were continuously exposed to the anti-androgen compounds for 144 hours at the concentration of 20.0 µM.

All the compounds showed to be able to induce higher cell death fraction in LNCaP cells than the control substance bicalutamide. (R)-XXIII-5, (R)-XXIII-9, (R)-XXIII-10 and (R)-XXIV-9 showed the highest pro-apoptotic activity (the percentage of apoptotic cells induced by such compounds was higher than 90%) and maintain this property also in LNCaP-AR cells.

FIG. 16-25 display the cytotoxic effect and apoptotic activity of bicalutamide derivatives on PC-3 and DU145 cell lines.

The authors tested the antitumour activity of the compounds also on PC-3 and DU145 cancer cell lines, representative of hormone-refractory prostate cancer due to AR receptor absence. As expected, (R)-XIII-2, (R)-XIII-3, (R)-XIII-4, (R)-XIII-5, (R)-XIII-6, (R)-XIII-7 and (R)-XIII-8 induced negligible cytotoxic activity on both cell lines. The presence of AR receptor seems to be essential for the antitumor proprieties of these compounds, which could mean they act through AR binding.

By contrast, the compounds (R)-XXIII-9, (R)-XXIII-10, and (R)-XXIV-9 maintain their cytostatic and cytocidal activity reaching $LC_{50}$ values in one ((R)-XXIV-9) or both ((R)-XXIII-9, (R)-XXIII-10) cell lines. The authors hypothesize that different mechanisms beyond the AR inhibition underlie the high antitumor activity observed. Notably, the compound (R)-XIII-5 exerted a reduced cytotoxic propriety in hormone-refractory cell lines respect to that observed in LNCaP and LNCaP-AR cells. For this reason, the activity of (R)-XIII-5 seems highly dependent from AR receptor presence.

FIG. 26 shows the ability of (R)-XXIII-6 to inhibit clonogenic growth of normal stem cells derived from human peripheral blood stem cells. The authors also evaluated in vitro the potential toxicity of (R)-XXIII-6 in normal cells as the ability of the drugs to inhibit clonogenic growth of normal stem cells derived from human peripheral blood stem cells. In this in vitro model, the compound does not seem to exert significant mielotoxicity, a recurring side effect observed in several chemotherapeutic regimens. In fact, the exposure of hematopoietic precursor to the compound caused a weak cytostatic activity, not being able to reach $GI_{50}$ value also at the highest concentration tested.

FIG. 27-36 show the cytotoxic activity of the drugs on the human hepatoblastoma cell line HepG2. The authors evaluated in vitro the potential hepato-toxicity of some of the novel compounds on HepG2 cell line, a human hepatoblastoma cell line that retains the specialized function of normal hepatocytes [Knowles B B, Howe C C, Aden D P. Human hepatocellular carcinoma cell lines secretes the major plasma proteins and hepatitis B surface antigen. Science 1980, 209:497-499; Aden D P, Vogel A, Plortkin S, Damjanov I, Knowles B B. Controlled synthesis of HBS Ag in a differentiated human liver carcinoma-derived cell line. Nature, 1979, 282:615-616]. Hepato-toxicity was observed only when this cell line was exposed to the compounds (R)-XIII-9 and (R)-XIII-10. However, both compounds are not able to reach $LC_{50}$ value (a parameter of high cytotoxic activity) also at the highest concentration tested. The other compounds, (R)-XIII-2, (R)-XIII-3, (R)-XIII-4, (R)-XIII-5, (R)-XIII-6, (R)-XIII-7, (R)-XIII-8 and (R)-XXIV-9, did not display toxicity also at the highest concentration tested.

EXAMPLE 7

Human Androgen Receptor (hAR) Transcriptional Activity

Constructs

The cDNA coding hAR was cloned into the pSG5 expression vector as reported previously [Chang, C. S., J. Kokontis, and S. T. Liao 1988 Molecular cloning of human and rat complementary DNA encoding androgen receptors Science 240:324-326].

The 3416 construct (ARE-Luc), containing four copies of the wild-type slp-HRE2 (5'-TGGTCAgccAGTTCT-3') was cloned in the NheI site in pTK-TATA-Luc [Verrijdt, G., E. Schoenmakers, A. Haelens, B. Peeters, G. Verhoeven, W. Rombauts, and F. Claessens 2000 Change of specificity mutations in androgen selective enhancers J. Biol. Chem. 275: 12298-12305].

Transactivation Assay

For androgen-stimulated transcriptional analysis, $32 \times 10^4$ Cos-7 cells were plated in phenol red-free DMEM containing 5% charcoal-stripped serum. After 48 h, the cells were transfected by Superfect (Qiagen) with 0.3 µg of 3416-pTK-TATA-Luc construct, together with 1.5 µg of either pSG5-empty plasmid or pSG5-hAR expressing plasmid. After 18 h, transfected cells were stimulated for 24 h with 10 nM of the synthetic androgen, R1881 (radiolabelled methyltrienolone 17 beta-hydroxy-17 alpha-methyl-estra-4,9,11-trien-3-one used in place of DHT, bought from Perkin Elmer, USA; dissolved in 0.001% ethanol, final concentration), in the absence or presence of the indicated concentrations of synthetic compounds. When indicated, the synthetic compounds were added alone to the cell medium. The antiandrogen Casodex (Astra-Zeneca) was used at 10 µM. It was dissolved in 0.001% (final concentration) ethanol. Control cells were treated with the vehicle alone. Lysates were prepared and the luciferase activity was measured using a luciferase assay system (Promega). The results were corrected using CH110-expressed beta-galactosidase activity (Amersham Biosciences) and luciferase activity was expressed as fold induction. Results were obtained from two or three different experiments, each performed in duplicate. Mean and SEM are shown.

AR Detection by Western Blot

For detection of ectopically expressed AR, lysates from Cos cells transfected with pSG5-hAR plasmid were prepared as described [Migliaccio, A., D. Piccolo, G. Castoria, M. Di Domenico, A. Bilancio, M. Lombardi, W. Gong, M. Beato, and F. Auricchio 1998 Activation of the Src/p21ras/Erk pathway by progesterone receptor via cross-talk with estrogen receptor. EMBO J. 17:2008-2018]. Lysates from cells transfected with the empty pSG5 plasmid were used in parallel, as a control. Protein concentrations were measured using a Bio-Rad protein assay kit (Bio-Rad Laboratories). Lysates (2 mg/ml protein concentration) were submitted to SDS-PAGE (12% acrylammide) and separated proteins were then transferred to nitrocellulose transfer membrane (Protran; Whatman GmbH) as previously described [Migliaccio, A., D. Piccolo, G. Castoria, M. Di Domenico, A. Bilancio, M. Lombardi, W. Gong, M. Beato, and F. Auricchio 1998 Activation of the Src/p21ras/Erk pathway by progesterone receptor via cross-talk with estrogen receptor. EMBO J. 17:2008-2018]. To reveal expression of AR, nitrocellulose membranes were finally submitted to Western blot using the rabbit polyclonal anti-AR antibodies (either C-19 or N-20; from Santa Cruz) as described [Castoria, G., M. Lombardi, M. V. Barone, A. Bilancio, M. Di Domenico, D. Bottero, F. Vitale, A. Migliaccio, and F. Auricchio 2003 Androgen-stimulated DNA synthesis and cytoskeletal changes in fi broblasts by a nontranscriptional receptor action J. Cell Biol. 161: 547-556].

FIG. 36 represents the dosage of the human androgen receptor transcriptional activity in the presence of compounds (R)-XXIII-4 and (R)-XXIII-6. FIG. 36 shows that 10 nM R1881 [radiolabelled methyltrienolone 17 beta-hydroxy-17 alpha-methyl-estra-4,9,11-trien-3-one used in place of DHT, bought from Perkin Elmer, USA] increases by about 20 fold the transcriptional activation mediated by AR ectopically expressed in Cos-7 cells and assayed using an ARE-reporter gene. The antiandrogen Casodex (at 10 µM) inhibits such an activation. A more pronounced inhibition is observed in cells treated with 10 nM R1881 in the presence of 10 µM (R)-XXIII-4 compound. The compound (R)-XXIII-6 does not seem to display agonistic activity. It shows antagonistic activity when used at 10 µM in cells challenged with 10 nM R1881, Data in Fig. have been obtained from 3 independent experiments. Mean and SEM is shown.

FIG. 37 represents an assay of the human androgen receptor transcriptional activity in the presence of compounds (R)-XXIII-3 and (R)-XXIII-5. FIG. 37 shows that 10 nM R1881 increases by 4.5 fold the transcriptional activation mediated by AR ectopically expressed in Cos-7 cells and assayed using an ARE-reporter gene. The antiandrogen Casodex (at 10 µM) inhibits such an activation. A more robust inhibition is observed in cells treated with 10 nM R1881 in the presence of 10 µM of (R)-XXIII-3 or (R)-XXIII-5. The compounds do not exhibit agonistic activity when used alone in the range between 10 nM-1 µM (for (R)-XXIII-5) or in the range between 10 nM-10 µM (for (R)-XXIII-3). FIG. 38 shows the assay of the human androgen receptor transcriptional activity in the presence of compounds (R)-XXIII-8. FIG. 38 shows that 10 nM R1881 increases by about 11 fold the transcriptional activation mediated by AR ectopically expressed in Cos-7 cells and assayed using an ARE-reporter gene. The antiandrogen Casodex (at 10 µM) inhibits such activation. Similar inhibition is observed in cells challenged with R-XXIII-8 compound. In addition, this compound does not increase the transcriptional activity of AR when used in the range between 10 nM-1 µM. This means that in a wide range of concentrations the compound does not exhibit any agonistic activity.

EXAMPLE 8

In Vivo Antitumor Activity

CW-22Rv1, a human prostate carcinoma epithelial cell line were purchased from ATCC.

In vivo antitumor activity experiments with the compound (R)-XXIII-6 were carried out using female athymic Swiss nude mice 8 to 10 weeks of age (Charles River, Calco, Italy). Mice were maintained in laminar flow rooms, keeping temperature and humidity constant. Mice had free access to food and water. Experiments were approved by the Ethics Committee for Animal Experimentation of the Istituto Nazionale Tumori (Milan, Italy).

Human CW22-RV1 cells, a human prostate carcinoma epithelial cell line, derived from a xenograft that was serially propagated in mice after castration-induced regression and relapse of the parental, androgen-dependent CWR22 xenograft, were used for in vivo experiments. The prostate carcinoma cell line were inoculated by subcutaneous injection (s.c.) in the right flank of nude mice, at day 0. Treatment started at day 3 when tumor weights were around 60 mg.

The efficacy of the drug treatment was assessed as: (a) TWI % in treated versus control mice, calculated as TWI=100−(mean TW treated/mean TW control×100).

The toxicity of the drug treatment was assessed as: (a) BWL calculated as BWL=100−(mean $BW_{day_x}$/mean $BW_{day_1}$×100), where day 1 is the first day of treatment and day x is any day after (mice were weighed twice/week throughout the experimental frame and in the table 3 the maximum BWL value was reported); and (b) lethal toxicity, i.e., any death in treated groups occurring before any control death (mice were inspected daily for mortality).

FIG. 39 shows the antitumor activity of (R)-XXIII-6 against the human CW22-RV1 prostatic carcinoma xenograft.

The figure shows a significant reduction in tumor weight in mice treated with (R)-XXIII-6 in respect to the untreated mice. Furthermore, the antitumor activity of (R)-XXIII-6 against CW22-RV1 cells was higher than that showed on the same cell line by the parental compound bicalutamide as reported by Zhou J et coworkers (Zhou J et al. Synthesis and in vitro characterization of ionone-based chalcones as novel antiandrogens effective against multiple clinically relevant androgen receptor mutants. Invest New Drugs 2009.

Results are summarized in the following table.

TABLE 3

Antitumor effects of (R)-XXIII-6 against the human CW22-RV1 prostate carcinoma xenograft inoculated s.c. in nude mice

| Drug[a] | Dose (mg/Kg) | Max TWI %[b] (day) | Max[d] BWL | Tox/Tot[e] (day) |
|---|---|---|---|---|
| (R)-XXIII-6 | 100 | 45 (23) | 2 | 0/6 |

[a]Drugs were dissolved in 10% DMSO in distilled water.
[b]Maximum TWI %, in parenthesis the day after tumor inoculum.
[d]Maximum body weight loss in percentage during drug treatment.
[e]Any death in treated mice occurring before any in control mice.
Tumor fragments were implanted s.c. in the right flank of nude mice, at day 0. Treatment started at day 3 when tumor weights were around 60 mg. Treatment schedule was (qdx5/wx2w) x 2 cycles, with a week of interval between the cycles.

The table reports the results of the antitumor activity studies with 2 cycles of the qdx5/wx2w schedule with a week of interval between the cycles. Treatment with the tested dose of (R)-XXIII-6 (100 mg/kg) was effective in slowing tumor growth, as evidenced by the TWI index. Furthermore, (R)-XIII-6, according to the in vitro toxicity experiments, was generally well tolerated, with no signs of acute or delayed toxicity. In particular, only a 2% reduction in body weight was observed at the end of the treatment, completely reversible upon cessation of treatment.

The invention claimed is:
1. A compound of formula I:

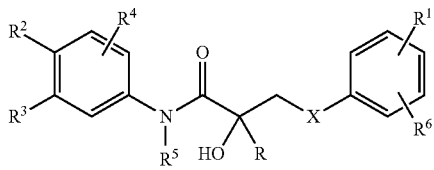

wherein R is selected from the group consisting of:
aryl, optionally substituted aryl, heteroaryl, optionally substituted heteroaryl, straight or branched $C_{2-10}$ heteroalkyl, substituted straight or branched $C_{2-10}$ heteroalkyl, $C_1$-$C_4$-arylalkyl, substituted $C_1$-$C_4$-arylalkyl, $C_{1-4}$ heteroarylalkyl, and substituted $C_{1-4}$ heteroarylalkyl;
X is oxygen, sulfur, sulfinyl (—SO—), sulfonyl (—SO$_2$—), —NR″—, —PR″—, or —Se—, where R″ is H, or $C_1$-$C_4$ alkyl;
$R^1$ and $R^6$ are the same or different and each is independently selected from the group consisting of H, $C_{1-4}$ alkyl, halogen, —NO$_2$, —CN, —SiR$^i_3$, —NHCOCF$_3$, —NHCOR$^i$, —NHCONHR$^i$, —NHCOOR$^i$, —OCONHR$^i$, —CONHR$^i$, —NHCSCF$_3$, —NHCSR$^i$, —NHSO$_2$R$^i$, —NCS—OR$^i$, —COR$^i$, —COOR$^i$, —OSO$_2$R$^i$, —SO$_2$R$^i$, —S—R$^i$, —R$^{ii}$, and —R$^{iii}$,
wherein R$^i$ is H, $C_{1-4}$ alkyl, $C_{1-4}$ haloalkyl, $C_{1-4}$ di-haloalkyl, $C_{1-4}$ tri-haloalkyl, $C_{1-4}$ perfluoro-alkyl, aryl, halogen, or $C_{2-4}$ alkenyl;
R$^{ii}$ is a fused ring with the phenyl residue, formed as $R_1$ and $R_6$ are joined together, selected from the group consisting of:

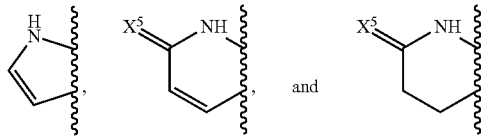

$X^5$ is S, SO$_2$, SO, or O;
R$^{iii}$ is $(C_1$-$C_4)$-halo alkyl, $C_{1-4}$ di-haloalkyl, $(C_1$-$C_4)$-tri-haloalkyl, $(C_1$-$C_4)$-perfluoro-alkyl, or CF$_2$CF$_3$;
$R^5$ is H, or $C_1$-$C_4$-alkyl;
$R^4$ is H, F, Cl, I or Br; and
$R^2$ and $R^3$ are the same or different and each is independently selected from the group consisting of H, $C_{1-4}$ alkyl, —CN, carbamoyl methyl, —NO$_2$, halogen, $C_{1-4}$ alkoxy, $C_{1-4}$ alkanoyl, $C_{1-4}$ thio-alkyl, $C_{1-4}$ alkyl-sulphinyl, $C_{1-4}$ alkyl-sulphonyl, $C_{1-4}$ perfluoro-alkyl, $C_{1-4}$ perfluoro-thio-alkyl, $C_{1-4}$ perfluoro-alkyl-sulphinyl, and $C_{1-4}$ perfluoro-alkyl-sulphonyl,
with the condition that the $C_{1-4}$ alkyl, the $C_{1-4}$ alkoxy, the $C_{1-4}$ alkanoyl, the $C_{1-4}$ thio-alkyl, the $C_{1-4}$ alkyl-sulphinyl, the $C_{1-4}$ alkyl-sulphonyl, the $C_{1-4}$ perfluoro-alkyl, the $C_{1-4}$ perfluoro-thio-alkyl, the $C_{1-4}$ perfluoro-alkyl-sulphinyl, the $C_{1-4}$ perfluoro-alkyl-sulphonyl are each optionally bound to a $C_{1-4}$ alkyl, a phenyl, a thio-phenyl, a sulphinyl-phenyl, or a sulphonyl-phenyl.

2. A compound according to claim 1, wherein R is selected from the group consisting of:
aryl, optionally substituted aryl, heteroaryl, optionally substituted heteroaryl, straight or branched $C_{2-10}$ heteroalkyl, substituted straight or branched $C_{2-10}$ heteroalkyl, $C_1$-$C_4$-arylalkyl, substituted $C_1$-$C_4$-arylalkyl, $C_{1-4}$ heteroarylalkyl, and substituted $C_{1-4}$ heteroarylalkyl;
X is oxygen (—O—), sulfur (—S—), sulfinyl (—SO—), or sulfonyl (—SO$_2$—); and
$R^1$ and $R^6$ are the same or different and each is independently selected from the group consisting of H, $C_{1-4}$ alkyl, halogen, —NO$_2$, —CN, SiR$^i_3$, —NHCOCF$_3$, —NHCOR$^i$, —NHCONHR$^i$, —NHCOOR$^i$, —OCONHR$^i$, —CONHR$^i$, —NHCSCF$_3$, —NHCSR$^i$, —NHSO$_2$R$^i$, —NCS—OR$^i$, —COR$^i$, —COOR$^i$, —OSO$_2$R$^i$, —SO$_2$R$^i$, —R$^{ii}$, and —R$^{iii}$,
wherein R$^i$ is H, $C_{1-4}$ alkyl, $C_{1-4}$ haloalkyl, $C_{1-4}$ di-haloalkyl, $C_{1-4}$ tri-haloalkyl, $C_{1-4}$ perfluoro-alkyl, aryl, halogen, or $C_{2-4}$ alkenyl;
R$^{ii}$ is a fused ring with the phenyl residue, formed as $R_1$ and $R_6$ are joined together, selected from the group consisting of:

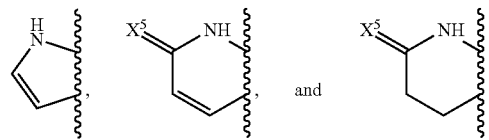

$X^5$ is S, SO$_2$, SO, or O; and
R$^{iii}$ is $(C_1$-$C_4)$-halo alkyl, $C_{1-4}$ di-haloalkyl, $(C_1$-$C_4)$-tri-haloalkyl, $(C_1$-$C_4)$-perfluoro-alkyl, or CF$_2$CF$_3$.

3. A compound according to claim 1, wherein R is selected from the group consisting of:
aryl, optionally substituted aryl, heteroaryl, optionally substituted heteroaryl, straight or branched $C_{2-10}$ heteroalkyl, substituted straight or branched $C_{2-10}$ heteroalkyl, $C_1$-$C_4$-arylalkyl, substituted $C_1$-$C_4$-arylalkyl, $C_{1-4}$ heteroarylalkyl, and substituted $C_{1-4}$ heteroarylalkyl;
$R^5$ is H, or $C_1$-$C_4$-alkyl;
$R^4$ is H, F, Cl, I or Br; and
$R^2$ and $R^3$ are the same or different and each is independently selected from the group consisting of —CN, —NO$_2$, halogen, $C_{1-4}$ alkoxy, $C_{1-4}$ thio-alkyl, or $C_{1-4}$ perfluoro-alkyl.

4. A compound according to claims 1, wherein R is selected from the group consisting of:
aryl, $C_1$-$C_4$-arylalkyl, substituted $C_1$-$C_4$-arylalkyl, $C_{1-4}$ heteroarylalkyl, and substituted $C_{1-4}$ heteroarylalkyl; and
$R^1$ and $R^6$ are the same or different and each are independently halogen, —NO$_2$, —CN, or —R$^{iii}$, wherein R$^{iii}$ is $(C_1$-$C_4)$-halo alkyl, $C_{1-4}$ di-haloalkyl, $(C_1$-$C_4)$-tri-haloalkyl, or CF$_2$CF$_3$.

5. A compound according to claim 1, wherein R is selected from the group consisting of:
aryl, $C_1$-$C_4$-arylalkyl, substituted $C_1$-$C_4$-arylalkyl, $C_{1-4}$ heteroarylalkyl, and substituted $C_{1-4}$ heteroarylalkyl;
$R^1$ is halogen, —NO$_2$, —CN, or —R$^{iii}$, wherein R$^{iii}$ is $(C_1$-$C_4)$-halo alkyl, $C_{1-4}$ di-haloalkyl, $(C_1$-$C_4)$-tri-haloalkyl, or CF$_2$CF$_3$; and
$R^6$ is H.

6. A compound according to claim 1, wherein R is selected from the group consisting of:
aryl, $C_1$-$C_4$-arylalkyl, substituted $C_1$-$C_4$-arylalkyl, and $C_{1-4}$ heteroarylalkyl;
$R^1$ is halogen, —NO$_2$, or —CN;

R⁵ is H, or $C_1$-$C_4$-alkyl;
R² is —CN, —NO₂, halogen, or $C_{1-2}$ perfluoro-alkyl; and
R³ is —CN, —NO₂, halogen, or $C_{1-2}$ perfluoro-alkyl.

7. A compound according claim 6, wherein R is selected from the group consisting of:
phenyl, $C_1$-$C_2$-arylalkyl, substituted $C_1$-$C_2$-arylalkyl, and $C_{1-2}$ heteroarylalkyl;
X is —S—, —SO₂—, or —O—;
R¹ is halogen, or —CN;
R⁵ is H;
R⁴ is H;
R² is —CN, —NO₂, halogen, or $C_{1-2}$ perfluoro-alkyl; and
R³ is —CN, —NO₂, halogen, or $C_{1-2}$ perfluoro-alkyl.

8. A compound according to claim 1, wherein R is selected from the group consisting of:
phenyl, $C_1$-$C_2$-arylalkyl, substituted $C_1$-$C_2$-arylalkyl, and $C_{1-2}$ heteroarylalkyl;
R¹ is in para position with respect to X;
R² is —CN, or —NO₂; and
R³ is halogen, or $C_{1-2}$ perfluoro-alkyl.

9. A compound according to claim 1 having the following stereoisomer structure:

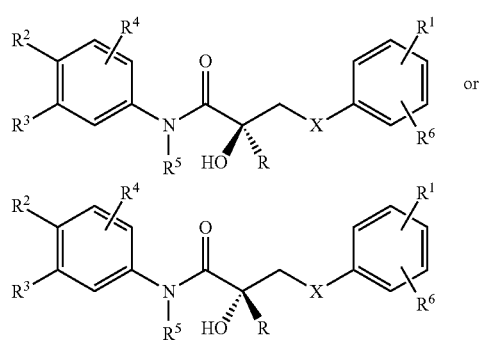

wherein the substituents are defined as in claim 1.

10. A compound according to claim 1 having the formula III or IV:

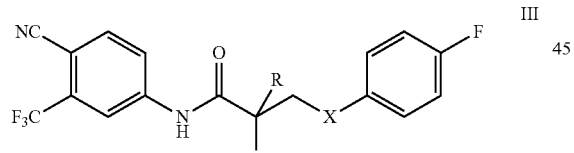

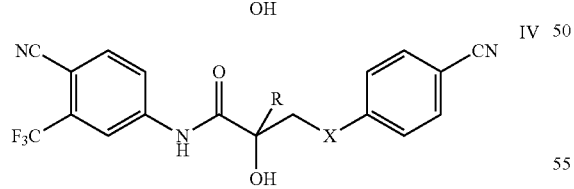

wherein R is selected from the group consisting of aryl, optionally substituted aryl, heteroaryl, optionally substituted heteroaryl, straight or branched $C_{2-10}$ heteroalkyl, substituted straight or branched $C_{2-10}$ heteroalkyl, $C_1$-$C_4$-arylalkyl, substituted $C_1$-$C_4$-arylalkyl, $C_{1-4}$ heteroarylalkyl, and substituted $C_{1-4}$ heteroarylalkyl; and
X is selected from the group consisting of oxygen, sulfur, sulfinyl (—SO—), sulfonyl (—SO₂—), —NR″—, —PR″—, and —Se—, where R″ is H, or $C_1$-$C_4$ alkyl.

11. A compound according to claim 1 selected from the group consisting of:

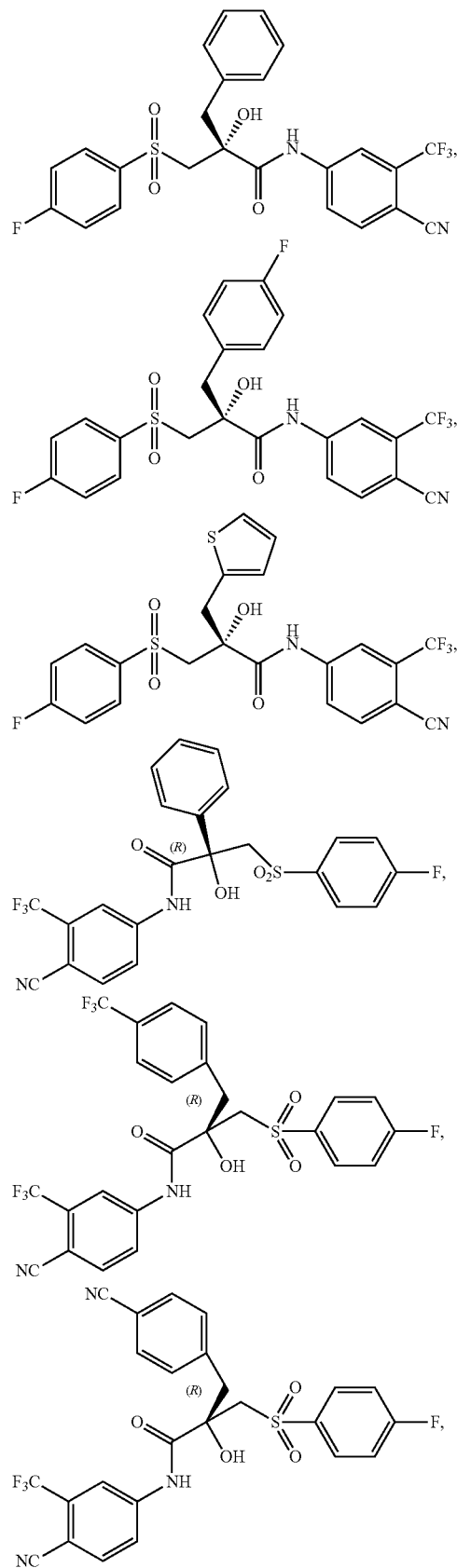

-continued

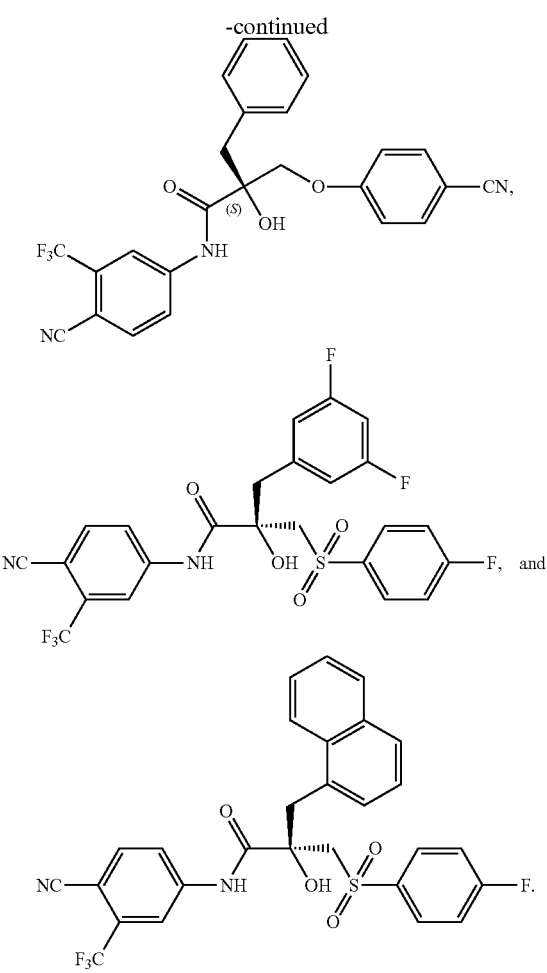

12. A pharmaceutical composition comprising the compound according to claim 1 and/or its isomer, pharmaceutically acceptable salts, crystal or N-oxide, hydrate or any combination thereof.

13. A method of treating an androgen receptor dependent prostate tumor in a subject, comprising administering an effective amount of the composition of claim 12 to a subject in need thereof.

14. A method for the preparation of a compound according to claim 1, comprising:

a protecting step comprising reacting a compound of general formula XXXV (XXXV)

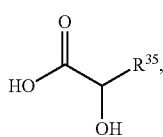

wherein $R^{35}$ is R or $CH_2COOH$, with a compound of general formula XXXVI (XXXVI)

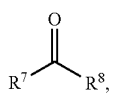

wherein $R^7$ and $R^8$ can be the same or different and each is H, or $C_1$-$C_6$ alkyl, in order to obtain a compound of general formula XXXVII (XXXVII)

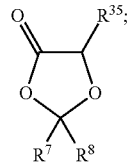

an electrophilic substitution step, comprising reacting where the compound of general formula XXXVII, under basic conditions, with a reactant of formula $R^{36}$-LG wherein $R^{36}$ is R, $CH_2$—$X^3$, wherein $X^3$ is halogen, —OH, or —$OR^{iv}$, wherein $R^{iv}$ is $SO_2CH_3$, $SO_2$-p-$CH_3$—$C_6H_5$, $C_1$-$C_4$-alkyl, $C_1$-$C_4$-arylalkyl, —$COR^v$, or —$COOR^v$, wherein $R^v$ is $C_1$-$C_4$-alkyl; and LG is a leaving group to provide an intermediate of general formula IXC (IXC)

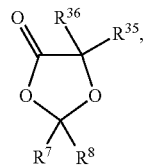

a deprotection step, comprising removing residue XXXVI;

a nucleophilic substitution step, comprising substituting —$X^3$ with the residue

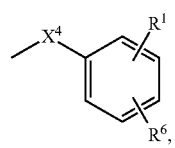

wherein $X^4$ is —S—, —$SO_2$—, —SO—, —O—, —$NR''$, —Se—, or —$PR^a$; and a coupling step with an amine of general formula XC which is reacted with the free carboxylic acid or its ester of the compound resulting from the nucleophilic substitution step (XC)

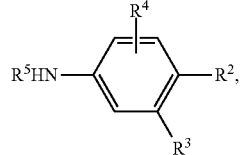

wherein when $X^4$ is —S—, the process further comprises an oxidation step so that X will be —SO— or —$SO_2$—.

15. The method of claim 14 wherein when $R^{35}$ is $CH_2COOH$, $R^{36}$ is R and the intermediate of formula IXC is reacted under halogen-decarboxilative conditions, and the compound of formula VIII obtained

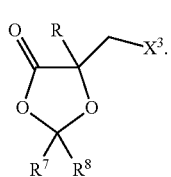
(VIII)
* * * * *

SEQUENCE LISTING

<160> NUMBER OF SEQ ID NOS: 1

<210> SEQ ID NO 1
<211> LENGTH: 15
<212> TYPE: DNA
<213> ORGANISM: Artificial Sequence
<220> FEATURE:
<223> OTHER INFORMATION: synthetic construct

<400> SEQUENCE: 1
tggtcagcca gttct                                                                15